(12) United States Patent
Behan et al.

(10) Patent No.: US 12,377,067 B2
(45) Date of Patent: Aug. 5, 2025

(54) METHODS OF TREATING PAH WITH COMBINATIONS OF RALINEPAG AND OTHER AGENTS

(71) Applicants: Arena Pharmaceuticals, Inc., San Diego, CA (US); Lucie H. Clapp, London (GB)

(72) Inventors: Dominic P. Behan, San Diego, CA (US); John W. Adams, San Diego, CA (US); Lucie H. Clapp, London (GB)

(73) Assignees: ARENA PHARMACEUTICALS, INC., San Diego, CA (US); Lucie H. Clapp, London (GB)

( * ) Notice: Subject to any disclaimer, the term of this patent is extended or adjusted under 35 U.S.C. 154(b) by 0 days.

(21) Appl. No.: 16/348,665

(22) PCT Filed: Nov. 10, 2017

(86) PCT No.: PCT/US2017/061116
§ 371 (c)(1),
(2) Date: May 9, 2019

(87) PCT Pub. No.: WO2018/089804
PCT Pub. Date: May 17, 2018

(65) Prior Publication Data
US 2019/0321328 A1 Oct. 24, 2019

Related U.S. Application Data

(60) Provisional application No. 62/420,515, filed on Nov. 10, 2016, provisional application No. 62/530,533, filed on Jul. 10, 2017.

(51) Int. Cl.
| | | |
|---|---|---|
| A61K 31/32 | (2006.01) |
| A61K 31/192 | (2006.01) |
| A61K 31/325 | (2006.01) |
| A61K 31/506 | (2006.01) |
| A61K 31/513 | (2006.01) |
| A61K 31/519 | (2006.01) |
| A61K 45/06 | (2006.01) |
| A61P 9/12 | (2006.01) |
| A61P 35/00 | (2006.01) |

(52) U.S. Cl.
CPC .......... *A61K 31/325* (2013.01); *A61K 31/192* (2013.01); *A61K 31/506* (2013.01); *A61K 31/513* (2013.01); *A61K 31/519* (2013.01); *A61K 45/06* (2013.01); *A61P 9/12* (2018.01); *A61P 35/00* (2018.01)

(58) Field of Classification Search
CPC .................................................. A61K 31/325
See application file for complete search history.

(56) References Cited

U.S. PATENT DOCUMENTS

| | | |
|---|---|---|
| 5,849,919 A | 12/1998 | Hamanaka et al. |
| 6,746,729 B1 | 6/2004 | Cherkaoui et al. |
| 7,115,746 B2 | 10/2006 | Snoonian et al. |
| 7,202,253 B2 | 4/2007 | Lloyd et al. |
| 7,226,550 B2 | 6/2007 | Hou et al. |
| 8,895,776 B2 | 11/2014 | Tran et al. |
| 2003/0144350 A1 | 7/2003 | Stevenson et al. |
| 2004/0048844 A1 | 3/2004 | Nugiel et al. |
| 2006/0063930 A1 | 3/2006 | Agoston et al. |
| 2006/0258728 A1 | 11/2006 | Tani et al. |
| 2011/0053958 A1 | 3/2011 | Tran et al. |
| 2011/0224262 A1 | 9/2011 | Tran et al. |
| 2011/0245251 A1 | 10/2011 | Tran et al. |
| 2013/0217706 A1 | 8/2013 | Tran et al. |
| 2015/0025255 A1 | 1/2015 | Yiannikouros et al. |
| 2015/0126527 A1 | 5/2015 | Tran et al. |
| 2017/0360730 A1 | 12/2017 | Tran et al. |

FOREIGN PATENT DOCUMENTS

| | | |
|---|---|---|
| CN | 102036659 A | 4/2011 |
| WO | WO-02055484 A1 | 7/2002 |
| WO | WO-2005042022 A2 | 5/2005 |
| WO | WO-2007051255 A1 | 5/2007 |
| WO | WO-2007133653 A2 | 11/2007 |
| WO | WO-2009117095 A1 | 9/2009 |
| WO | WO-2010077275 A1 | 7/2010 |
| WO | WO-2011037613 A1 | 3/2011 |
| WO | WO-2016065103 A1 | 4/2016 |
| WO | WO-2018089804 A1 | 5/2018 |

OTHER PUBLICATIONS

Type 1 diabetes [online] retrieved from the internet on Jan. 29, 2021. URL: https://www.mayoclinic.org/diseases-conditions/type-1-diabetes/diagnosis-treatment/drc-2.*
Type 1 diabetes [online] retrieved from the internet on Jan. 11, 2022. URL https:www/mayoclinic.org/diseases-conditions/type-1-diabetes/symptoms-causes/syc-203.*
Stasch, et al. Pharmacotherapy of Pulmonary Hypertension, pp. 279-313; Jan. 1, 2013.*
Meis, et al. Expert Opinion on Pharmacotherapy, 15:16, (2014), 2419-2427.*
ADEMPAS® product information. Available at https://www.adempas-us.com/ (2 pgs.) (2019).

(Continued)

*Primary Examiner* — Shawquia Jackson
(74) *Attorney, Agent, or Firm* — WILSON SONSINI GOODRICH & ROSATI

(57) ABSTRACT

The present disclosure encompasses combinations of ralinepag with a cGMP-elevating agent or prostanoid such as riociguat, treprostinil, or iloprost for treating PAH. The disclosed combination therapy provides for advantages such as improved efficacy, improved safety, reduced doses and/or frequency of ralinepag and/or riociguat, reduced doses and/or frequency of ralinepag and/or treprostinil, and reduced doses and/or frequency of ralinepag and/or iloprost. In some embodiments, the clinical effectiveness of a reduced dose combination is additive or synergistic compared to that provided by the corresponding ralinepag, riociguat, treprostinil, and/or iloprost monotherapies.

32 Claims, 41 Drawing Sheets

(56) References Cited

OTHER PUBLICATIONS

ATS statement: guidelines for the six-minute walk test. ATS Committee on Proficiency Standards for Clinical Pulmonary Function Laboratories. Am J Respir 166(1):111-117 (2002).
Ballard et al., Effects of sildenafil on the relaxation of human corpus cavernosum tissue in vitro and on the activities of cyclic nucleotide phosphodiesterase isozymes. J Urol 159:2164-2171 (1998).
Barst et al., Beraprost therapy for pulmonary arterial hypertension. J Am Coll Cardiol 41:2119-2125 (2003).
Benyahia et al., A comparative study of PGI2 mimetics used clinically on the vasorelaxation of human pulmonary arteries and veins, role of the DP-receptor. Prostaglandins & Other Lipid Mediators 107:48-55 (2013).
Berge et al. Pharmaceutical Salts. Journal of Pharmaceutical Sciences 66(1):1-19 (Jan. 1977).
Bischoff. Potency, selectivity, and consequences of nonselectivity of PDE inhibition. Int J Impot Res 16 Suppl 1:S11-S14 (2004).
Bley KR et al., RO1138452 and RO3244794: characterization of structurally distinct, potent and selective IP (prostacyclin) receptor antagonists. Br J Pharmacol 147:335-345 (2006).
Bubb et al., Inhibition of phosphodiesterase 2 augments cGMP and cAMP signaling to ameliorate pulmonary hypertension. Circulation 130:496-507 (2014).
Burgess et al., Mutual pharmacokinetic interactions between steady-state bosentan and sildenafil. Eur J Clin Pharmacol 64:43-50 (2008).
Clapp et al. The mechanistic basis of prostacyclin and its stable analogues in pulmonary arterial hypertension: Role of membrane versus nuclear receptors. Prostaglandins Other Lipid Mediat 120:56-71 (2015).
Clapp et al., Differential effects of stable prostacyclin analogues on smooth muscle proliferation and cyclic AMP generation in human pulmonary artery. Am J Respir Cell Molec Biol 26:194-201 (2002).
Davie et al., ETA and ETB receptors modulate the proliferation of human pulmonary artery smooth muscle cells. Am J Respir Crit Care Med 165:398-405 (2002).
Davie et al., The science of endothelin-1 and endothelin receptor antagonists in the management of pulmonary arterial hypertension: current understanding and future studies. Eur J Clin Invest 39 Suppl 2:38-49 (2009).
Drogalis-Kim et al., Right sided heart failure and pulmonary hypertension: New insights into disease mechanisms and treatment modalities. Progress in Pediatric Cardiology 43:71-80 (2016).
Falcetti et al., Smooth muscle proliferation and role of the prostacyclin (IP) receptor in idiopathic pulmonary arterial hypertension. Am J Respir Crit Care Med 182:1161-1170 (2010).
Galie et al., Initial use of Ambrisentan plus Tadalafil in pulmonary arterial hypertension. New England Journal of Medicine 373:834-844 (2015).
Grimminger et al., First acute haemodynamic study of soluble guanylate cyclase stimulator riociguat in pulmonary hypertension. Eur Respir Journal 33:785-792 (2009).
Hoeper et al., Combining inhaled iloprost with bosentan in patients with idiopathic pulmonary arterial hypertension. Eur Respir Journal 28:691-694 (2006).
Humbert et al., Combination of bosentan with epoprostenol in pulmonary arterial hypertension: Breathe-2. Eur Respir J 24:353-359 (2004).
Iglarz et al., Comparison of pharmacological activity of macitentan and bosentan in preclinical models of systemic and pulmonary hypertension. Life Sci 118:333-339 (2014).
Jabr et al., Nuclear translocation of calcineurin AP but not calcineurin Aa by platelet-derived growth factor in rat aortic smooth muscle. American Journal of Physiology 292:C2213-C2225 (2007).
Kam et al., Factors affecting prostacyclin receptor agonist efficacy in different cell types. Cell Signal 13:841-847 (2001).
Knebel et al., Synergistic effects of prostacyclin analogs and phosphodiesterase inhibitors on cyclic adenosine 3',5' monophosphate accumulation and adenosine 3'5' triphosphate release from human erythrocytes. Experimental Biology and Medicine (Maywood) 238:1069-1074 (2013).
Kuwano et al., 2-[4-[(5,6-diphenylpyrazin-2-yl)(isopropyl)amino]butoxy]-N-(methylsulfonyl)acetamide (NS-304), an orally available and long-acting prostacyclin receptor agonist prodrug. J Pharmacol Exp Ther 322:1181-1188 (2007).
Lai et al., Role of the prostanoid EP4 receptor in iloprost mediated vasodilatation in pulmonary hypertension. Am J Respir Crit Care Med 178:188-196 (2008).
Lang et al., The soluble guanylate cyclase stimulator riociguat ameliorates pulmonary hypertension induced by hypoxia and SU5416 in rats. PLoS One 7:e43433 (2012).
Langleben et al., Use of clinically relevant responder threshold criteria to evaluate the response to treatment in the phase III Patent-1 study. J Heart Lung Transplant 34:338-347 (2015).
Lu et al., Calcineurin/NFAT signaling pathway mediates endothelin-I-induced pulmonary artery smooth muscle cell proliferation by regulating phosphodiesterase-5. Nan Fang Yi Ke Da Xue Xue Bao 33:26-29 (2013) (English Abstract).
McLaughlin et al., ACCF/AHA 2009 expert consensus document on pulmonary hypertension a report of the American College of Cardiology Foundation Task Force on Expert Consensus Documents and the American Heart Association developed in collaboration with the American College of Chest Physicians; American Thoracic Society, Inc.; and the Pulmonary Hypertension Association. J Am Coll Cardiol 53:1573-1619 (2009).
McLaughlin et al., Bosentan added to sildenafil therapy in patients with pulmonary arterial hypertension. Eur Respir J 46:405-413 (2015).
Murray et al.,Expression and activity of cAMP phosphodiesterase isoforms in pulmonary artery smooth muscle cells from patients with pulmonary hypertension: role for PDE1. Am J Physiol Lung Cell Mol Physiol 292:L294-L303 (2007).
Orie et al., Differential actions of the prostacyclin analogues treprostinil and iloprost and the selexipag metabolite, MRE-269 (ACT-333679) in rat small pulmonary arteries and veins. Prostaglandins & Other Lipid Mediators 106:1-7 (2013).
Patel et al., Comparison of current therapies to inhibit endothelin-induced growth of pulmonary artery smooth muscle cells (PASMCs) derived from patients with pulmonary arterial hypertension. Eur. Respir. J. 44[Suppl. 58]:P2355 (2014).
Patel et al., EP2 receptors play a key role in meditating the anti-proliferative activity of treprostinil in smooth muscle cells derived from the lungs of pulmonary hypertensive patients. Am. J. Respir. Crit Care Med. 191:A5954 (2015).
PCT/US2017/061116 International Search Report and Written Opinion dated Jan. 9, 2018.
PCT/US2018/020519 International Preliminary Report on Patentability dated Sep. 12, 2019.
Pugliese et al., Clinical use of extended-release oral treprostinil in the treatment of pulmonary arterial hypertension. Integrated Blood Pressure Control 9:1-7 (2016).
Schermuly et al., Expression and function of soluble guanylate cyclase in pulmonary arterial hypertension. Eur Respir J 32:881-891 (2008).
Schermuly et al., Iloprost-induced desensitization of the prostacyclin receptor in isolated rabbit lungs. Respir Res 8:4 (2007).
Simonneau et al., Addition of sildenafil to long-term intravenous epoprostenol therapy in patients with pulmonary arterial hypertension: a randomized trial. Ann Intern Med 149:521-530 (2008).
Sitbon et al., Selexipag for the treatment of pulmonary arterial hypertension. New England Journal of Medicine 373:2522-2533 (2015).
Skoro-Sajer et al. Selexipag for the treatment of pulmonary arterial hypertension. Expert Opin Pharmacother 15:429-436 (2014).
Syed et al. Assessing the agonist profiles of the prostacyclin analogues treprostinil and naxaprostene, particularly their DP1 activity. Prostaglandins Leukot Essent Fatty Acids 95:19-29 (2015).
Tapson et al., Oral treprostinil for the treatment of pulmonary arterial hypertension in patients receiving background endothelin

(56) References Cited

OTHER PUBLICATIONS receptor antagonist and phosphodiesterase type 5 inhibitor therapy (the Freedom-C2 study): a randomized controlled trial. Chest 144:952-958 (2013).
Turcato et al. Evidence that vasorelaxation induced by Gs coupled receptors is largely independent of cAMP in guinea-pig aorta. Journal of Molecular and Cellular Cardiology 30:A190 (1998).
TYVASO® product information. Available at https://www.tyvaso.com (3 pgs.) (2018).
UPTRAVI® product information. Available at https://www.uptravi.com/ (3 pgs.) (2018).
Vachiery. Prostacyclins in pulmonary arterial hypertension: the need for earlier therapy. Adv Ther 28:251-269 (2011).
Wang et al., Sildenafil inhibits hypoxia-induced transient receptor potential canonical protein expression in pulmonary arterial smooth muscle via cGMP-PKG-PPARγ axis. Am J Respir Cell Mol Biol 49:231-240 (2013).
Wharton et al., Prostacyclin analogues differentially inhibit growth of distal and proximal human pulmonary artery smooth muscle cells. Circulation 102:3130-3136 (2000).
Whittle et al., Binding and activity of the prostacyclin receptor (IP) agonists, treprostinil and iloprost, at human prostanoid receptors: treprostinil is a potent DP1 and EP2 agonist. Biochem Pharmacol 84:68-75 (2012).
Wort et al., Endogenously released endothelin-1 from human pulmonary artery smooth muscle promotes cellular proliferation: relevance to pathogenesis of pulmonary hypertension and vascular remodeling. Am J Respir Cell Mol Biol 25:104-110 (2001).
Zamora et al., BQ123, an ETA receptor antagonist, inhibits endothelin-1-mediated proliferation of human pulmonary artery smooth muscle cells. Am J Respir Cell Mol Biol 9:429-433 (1993).
Zhang et al., Pulmonary artery smooth muscle cells from normal subjects and IPAH patients show divergent cAMP-mediated effects on TRPC expression and capacitative Ca2+ entry. Am J Physiol Lung Cell Mol Physiol 292:L1202-L1210 (2007).
Clapp et al. Phosphodiesterase-type 3 inhibitor potentiates cAMP generation and antiproliferative effects of treprostinil in pulmonary arterial smooth muscle cells from patients with pulmonary hypertension. Presented at: ERS Annual Congress 2010.
Ghofrani et al. Riociguat for the Treatment of Pulmonary Arterial Hypertension. N Engl J Med 369(4):330-40 (Jul. 25, 2013).
Shen et al. Abstract 16601: APD811, a Novel and Highly Selective Non-prostanoid IP Receptor Agonist in Smooth Muscle Cells From Patients With Pulmonary Hypertension. Circulation 134:A16601 (2016).
Baliga et al. New perspectives for the treatment of pulmonary hypertension. Br J Pharmacol 163(1):125-140 (2011).
Galie et al. The use of combination therapy in pulmonary arterial hypertension: new developments. Eur Respir Rev 18(113):148-153 (2009).
Simonneau et al. Selexipag: an oral, selective prostacyclin receptor agonist for the treatment of pulmonary arterial hypertension. Eur Respir J 40(4):874-880 (2012).
Ventetuolo et al. WHO Group 1 pulmonary arterial hypertension: Current and investigative therapies. Prog Cardiovasc Dis 55(2):89-103 (2012).
Aguilar et al. Epoprostenol (prostacyclin) therapy in HIV-associated pulmonary hypertension. Am. J. Respir. Crit. Care Med. 162:1846-1850 (2000).
Archer et al., Nitric oxide deficiency in fenfluramine- and dexfenfluramine-induced pulmonary hypertension. Am. J. Respir. Crit. Care Med. 158:1061-1067 (1998).
Arehart et al., Acceleration of cardiovascular disease by a dysfunctional prostacyclin receptor mutation: potential implications for cyclooxygenase-2 inhibition. Circ. Res. 102(8):986-993 (2008).
Arehart et al., Prostacyclin, atherothrombosis, and cardiovascular disease. Curr. Med. Chem. 14:2161-2169 (2007).

Asada et al., Discovery of a series of acrylic acids and their derivatives as chemical leads for selective EP3 receptor antagonists, Bioorganic & Medicinal Chemistry, Pergamon, GB 17(18):6567-6582 (2009).
Badesch et al., Continuous intravenous epoprostenol for pulmonary hypertension due to the scleroderma spectrum of disease. A randomized, controlled trial. Ann. Intern. Med. 132:425-434 (2000).
Badesch et al., Prostanoid therapy for pulmonary arterial hypertension. Journal of the American College of Cardiology 43(12 Suppl. S):56S-61S (2004).
Baradia et al., Inhalation therapy to treat pulmonary arterial hypertension. Pharm. Pat. Analyst 1(5):577-588 (2012).
Cameron et al., The effects of 5-hydroxytryptamine 5-HT2 receptor antagonists on nerve conduction velocity and endoneurial perfusion in diabetic rats. Naunyn Schmiedebergs Arch. Pharmacol. 367:607-614 (2003).
Cameron. Vascular factors and metabolic interactions in the pathogenesis of diabetic neuropathy. Diabetologia 44:1973-1988 (2001).
Caojin et al, Comparison of acute hemodynamic effects of aerosolized iloprost and inhaled nitric oxide in adult congenital heart disease with severe pulmonary arterial hypertension. Department of Cardiology, Guangdong General Hospital & Guangdong Cardiovascular Institute, China, Intern Med. 51:2857-2862 (2012).
Chan. Vitamin E and atherosclerosis. J. Nutr. 128:1593-1596 (1998).
Cheng et al., Role of prostacyclin in the cardiovascular response to thromboxane A2. Science 296:539-541 (2002).
Clinical Trials—Cancer. Genetic Engineering and Biotechnology News 32(20):54 (Nov. 15, 2012).
Collier et al, Radiosynthesis and in vivo evaluation of the pseudopeptide σ-opioid antagonist [125I]-ITIPP(ψ) J. Labelled Compd. Radiopharm 42:S264-S266 (1999).
Cote et al., Disruption of the nonneuronal tph1 gene demonstrates the importance of peripheral serotonin in cardiac function. PNAS 100(23):13525-13530 (2003).
Cotter et al., Prevention and reversal of motor and sensory peripheral nerve conduction abnormalities in streptozotocin-diabetic rats by the prostacyclin analogue iloprost. Naunyn Schmiedebergs Arch. Pharmacol. 347:534-540 (1993).
Czeslick et al., Inhibition of intracellular tumour necrosis factor (TNF)-alpha and interleukin (IL)-6 production in human monocytes by iloprost. Eur. J. Clin. Invest. 33:1013-1017 (2003).
Davi et al, Platelet activation and atherothrombosis. N. Eng. J. Med. 357:2482-2494 (2007).
Di Renzo et al., Iloprost treatment reduces TNF-alpha production and TNF-RII expression in critical limb ischemia patients without affecting IL6. Prostaglandin Leukot. Essent. Fatty Acids 73:405-410 (2005).
Dogan et al., Effect of the prostacyclin analogue, iloprost, on infarct size after permanent focal cerebral ischemia. Gen. Pharmacol. 27:1163-1166 (1996).
Driscoll et al., Medical therapy for pulmonary arterial hypertension. Expert Opin. Pharmacother. 9:65-81 (2008).
Fang et al, Induction of prostacyclin/PGI2 synthase expression after cerebral ischemia-reperfusion. J. Cereb. Blood Flow Metab. 26:491-501 (2006).
Fetalvero et al., Cardioprotective prostacyclin signaling in vascular smooth muscle. Prostaglandins Other Lipid Mediat. 82:109-118 (2007).
Fetalvero et al., The prostacyclin receptor induces human vascular smooth muscle cell differentiation via the protein kinase A pathway. Am. J. Physiol. Heart. Circ. Physiol. 290:H1337-H1346 (2006).
Fries et al., The cardiovascular pharmacology of COX-2 inhibition. Hematology Am. Soc. Hematol. Educ. Program, 2005:445-451 (2005).
Fujiwara et al., A stable prostacyclin analogue reduces high serum TNF-alpha levels in diabetic patients. Exp. Clin. Endocrinol. Diabetes 112:390-394 (2004).
Gabriel et al., High throughput screening technologies for direct cyclic AMP measurement. Assay and Drug Development Technologies, 1:291-303 (2003).
Gainza et al., Role of prostacyclin (epoprostenol) as anticoagulant in continuous renal replacement therapies: efficacy, security and cost analysis. J. Nephrol. 19:648-655 (2006).

(56) References Cited

OTHER PUBLICATIONS

Gao et al., A 7-day oral treatment of patients with active rheumatoid arthritis using the prostacyclin analog iloprost: cytokine modulation, safety, and clinical effects. Rheumatol. Int. 22:45-51 (2002).
Goya et al., Effects of the prostaglandin I2 analogue, beraprost sodium, on vascular cell adhesion molecule-1 expression in human vascular endothelial cells and circulating vascular cell adhesion molecule-1 level in patients with type 2 diabetes mellitus. Metabolism Clinical and Experimental 52:192-198 (2003).
Harada et al., Role of neutrophil elastase in development of pulmonary vascular injury and septic shock in rats. Shock 30(4):379-387 (2008).
Higuchi et al. Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).
Hoeper et al., Bosentan therapy for portopulmonary hypertension. Eur. Respir. J. 25:502-508 (2005).
Hoeper et al., Pulmonary hypertension after splenectomy? Ann. Intern. Med. 130(6):506-509 (1999).
Hotta et al, Effects of beraprost sodium and insulin on the electroretinogram, nerve conduction, and nerve blood flow in rats with streptozotocin-induced diabetes. Diabetes 45:361-366 (1996).
Hotta et al. Prevention of abnormalities in motor nerve conduction and nerve blood-flow by a prostacyclin analog, beraprost sodium, in streptozotocin-induced diabetic rats. Prostaglandins 49:339-349 (1995).
Hoyng et al., Iloprost, a stable prostacyclin analog, reduces intraocular pressure. Invest. Ophthalmol Vis. Sci. 28:470-476 (1987).
Humbert et al., Cellular and molecular pathobiology of pulmonary arterial hypertension. J. Am. Coll. Cardiol. 43:13S-24S (2004).
Humbert et al, Short-term and long-term epoprostenol (prostacyclin) therapy in pulmonary hypertension secondary to connective tissue diseases: results of a pilot study Eur. Respir. J. 13:1351-1356 (1999).
Idzko et al, Inhaled iloprost suppresses the cardinal features of asthma via inhibition of airway dendritic cell function. J. Clin. Invest. 117:464-472 (2007).
Jaffar et al., Prostaglandin I2-IP signaling blocks allergic pulmonary inflammation by preventing recruitment of CD4+ Th2 cells into the airways in a mouse model of asthma. J. Immunol 179:6193-6203 (2007).
Jozefowski et al., Exogenous but not endogenous prostanoids regulate cytokine secretion from murine bone marrow dendritic cells: EP2, DP, and IP but not EP1, EP3, and FP prostanoid receptors are involved. Int. Immunopharmcol. 3:865-878 (2003).
Kobayashi et al., Roles of thromboxane A(2) and prostacyclin in the development of atherosclerosis in apoE-deficient mice. J. Clin. Invest. 114:784-794 (2004).
Koike et al., Enhanced angiogenesis and improvement of neuropathy by cotransfection of human hepatocyte growth factor and prostacyclin synthase gene. FASEB J. 17:779-781 (2003).
Le Bas et al., Radioiodinated analogs of EP 00652218 for the exploration of the tachykinin NK1 receptor by spect. J Labelled Compd. Radiopharm 44:S280-S282 (2001).
Liu et al., Treatments for pulmonary arterial hypertension. Respiratory Medicine, Baillier Tindall, London, GB 100(5):765-774 (2006).
Lundblad et al., Increased cortical cell loss and prolonged hemodynamic depression after traumatic brain injury in mice lacking the IP receptor for prostacyclin. Journal of Cerebral Blood Flow & Metabolism 28:367-376 (2008).
Mardla et al., Potentiation of antiaggregating effect of prostaglandins by alpha-tocopherol and quercetin. Platelets 15:319-324 (2004).
McCormick et al., Prostacyclin analogues: the next drug-eluting stent? Biochem. Soc. Trans. 35:910-911 (2007).
McGoon et al., Screening, early detection, and diagnosis of pulmonary arterial hypertension: ACCP evidence-based clinical practice guidelines. Chest 126:14S-34S (2004).
McLaughlin et al, Pulmonary arterial hypertension. Pulmonary arterial hypertension. Circulation 114(13):1417-1431 (2006).
Miwa et al., Combination therapy with oral sildenafil and beraprost for pulmonary arterial hypertension associated with CREST syndrome. Int. Heart J. 48:417-422 (2007).
Moncada et al., Human arterial and venous tissues generate prostacyclin (prostaglandin x), a potent inhibitor of platelet aggregation. Lancet 1:18-20 (1977).
Morecroft et al., Effect of tryptophan hydroxylase 1 deficiency on the development of hypoxia-induced pulmonary hypertension. Hypertension 49:232-236 (2007).
Moss. Basic terminology of stereochemistry (IUPAC Recommendations 1996). Pure & Appl. Chem. 68(12):2193-2222 (1996).
Muller et al, Iloprost has potent anti-inflammatory properties on human monocyte-derived dendritic cells. Clinical & Experimental Allergy, Department of Pneumology, University of Freiburg, Germany 40:1214-1221 (2010).
Murata et al., Altered pain perception and inflammatory response in mice lacking prostacyclin receptor. Nature 388:678-682 (1997).
Naeije et al., Expert opinion on available options treating pulmonary arterial hypertension. Expert Opin. Pharmacother. 8:2247-2265 (2007).
Nagao et al., Role of prostaglandin I2 in airway remodeling induced by repeated allergen challenge in mice. Am. J. Respir. Cell Mol. Biol. 29:314-320 (2003).
Okuda et al., Acute effect of beraprost sodium on lower limb circulation in patients with non-insulin-dependent diabetes mellitus-evaluation by color Doppler ultrasonography and laser cutaneous blood flowmetry. Prostaglandins 52:375-384 (1996).
Rabinovitch. Pathobiology of pulmonary hypertension. Annu. Rev. Pathol. Mech. Dis. 2:369-399 (2007).
Raychaudhuri et al., The prostacyclin analogue treprostinil blocks NFkappaB nuclear translocation in human alveolar macrophages. J. Biol. Chem. 277:33344-33348 (2002).
Robbins et al., Epoprostenol for treatment of pulmonary hypertension in patients with systemic lupus erythematosus. Chest 117:14-18 (2000).
Rosenkranz. Pulmonary hypertension: Current diagnosis and treatment. Clin. Res. Cardiol. 96(8):527-541 (2007).
Rosenzweig. Emerging treatments for pulmonary arterial hypertension. Expert Opin. Emerging Drugs 11(4):609-619 (2006).
Schermuly et al., Antiremodeling effects of iloprost and the dual-selective phosphodiesterase 3/4 inhibitor tolafentrine in chronic experimental pulmonary hypertension. Circ. Res. 94:1101-1108 (2004).
Seiler et al., 2-[3-[2-(4,5-Diphenyl-2-oxazolyl) ethyl] phenoxy] acetic acid (BMY 42393): a new, structurally-novel prostacyclin partial agonist: 1). Inhibition of platelet aggregation and mechanism of action. Thrombosis Research 74(2):115-123 (1994).
Semple. Discovery of APDS811: an orally available prostacylcin receptor agonist for the treatment of Pulmonary Arterial Hypertension (PAH). Presentation for 4th RSC/SCI GPCRS in Medicinal Chemistry, Sep. 17-19, 2012 Surrey UK (39 pgs).
Shindo et al., Clinical efficacy of a stable prostacyclin analog, iloprost, in diabetic neuropathy. Prostaglandins 41:85-96 (1991).
Shinomiya et al., Regulation of TNFalpha and interleukin-10 production by prostaglandins I(2) and E(2): studies with prostaglandin receptor-deficient mice and prostaglandin E-receptor subtype-selective synthetic agonists. Biochem. Pharmacol. 61:1153-1160 (2001).
Simonneau et al., Clinical classification of pulmonary hypertension. J. Am. Coll. Cardiol. 43:5S-12S (2004).
Stitham et al., Human prostacyclin receptor structure and function from naturally-occurring and synthetic mutations. Prostaglandins Other Lipid Mediat. 82:95-108 (2007).
Strauss et al., Prostanoid therapy for pulmonary arterial hypertension. Clin. Chest. Med. 28:127-142 (2007).
Szekeres et al., Delayed antiischemic effect of PgI2 and of a new stable PgI2 analogue 7-oxo-prostacyclin-Na in experimental model angina in dogs. Journal of Molecular and Cellular Cardiology, Academic Press, GB 15:132 (1983).
Taichman et al., Epidemiology of pulmonary arterial hypertension. Clin. Chest. Med., 28:1-22 (2007).
Takahashi et al., Augmentation of allergic inflammation in prostanoid IP receptor deficient mice. Br. J. Pharmacol, 137:315-322 (2002).

(56) References Cited

OTHER PUBLICATIONS

Tawara et al., Effects of combined therapy with a Rho-kinase inhibitor and prostacyclin on monocrotaline-induced pulmonary hypertension in rats. Journal of Cardiovascular Pharmacology 50(2):195-200 (2007).

Tennis et al, The role of prostacyclin in lung cancer. Translation Research, Division of Pulmonary Sciences and Critical Care Medicine, Department of Medicine, University of Colorado Denver Health Sciences, Denver, Colorado 155(2):57-61 (2010).

Tuder et al., Prostacyclin synthase expression is decreased in lungs from patients with severe pulmonary hypertension. Am. J. Respir. Crit. Care Med. 159:1925-1932 (1999).

Ueno et al., Effects of beraprost sodium, a prostacyclin analogue, on diabetic neuropathy in streptozotocin-induced diabetic rats. Jpn. J. Pharmacol, 70:177-182 (1996).

Ueno et al., Effects of beraprost sodium, a prostacyclin analogue, on tail flick response in two models of diabetic-neuropathy in rats and its mechanism. Life Sci. 59:PL105-PL110 (1996).

Van Rijt et al., In vivo depletion of lung CD11c+ dendritic cells during allergen challenge abrogates the characteristic features of asthma. J. Exp. Med., 201:981-991 (2005).

Zhang et al, Characterization of the molecular mechanisms of the coupling between intracellular loops of prostacyclin receptor with the C-terminal domain of the Galphas protein in human coronary artery smooth muscle cells. Arch. Biochem. Biophys. 454:80-88 (2006).

Zhou et al., Prostaglandin I2 analogs inhibit proinflammatory cytokine production and T cell stimulatory function of dendritic cells. J. Immunol. 178:702-710 (2007).

Zhu et al, Synthesis and mode of action of (125)I- and (3)H-labeled thieno[2,3-c]pyridine antagonists of cell adhesion molecule expression. J. Org. Chem. 67:943-948 (2002).

Patel et al. Comparison of current therapies to inhibit endothelin-induced growth of pulmonary artery smooth muscle cells (PASMCs) derived from patients with pulmonary arterial hypertension. Poster 22nd Annual Congress, Munich, Germany Sep. 6-10, 2014.

Shen et al. APD811, a Novel and Highly Selective Non-prostanoid IP Receptor Agonist in Smooth Muscle Cells From Patients With Pulmonary Hypertension. AHA meeting of Nov. 12-16, 2016.

Chen et al. Uncovering Stimulator Binding Mechanism to Soluble Guanylyl Cyclase by Solution NMR. Protein Science 25:151-152 (2016).

Mittendorf. Discovery of Riociguat: A Potent, Oral Stimulator of Soluble Guanylate Cyclase for the Treatment of Pulmonary Hypertension. Drugs of the Future 35(Supp A):9 (LO6) (2010).

Smith et al. Calcium-Sensing Receptor Regulates Cytosolic [Ca 2+ ] and Plays a Major Role in the Development of Pulmonary Hypertension. Front Physiol 7:517 (2016).

Stasch et al. Soluble guanylate cyclase as an emerging therapeutic target in cardiopulmonary disease. Circulation 123(20):2263-2273 (2011).

Das Gupta et al. Soluble guanylate cyclase: a new therapeutic target for pulmonary arterial hypertension and chronic thromboembolic pulmonary hypertension. Clin Pharmacol Ther 97(1):88-102 (2015).

Demir, Rengin et al. Six-minute walk test in pulmonary arterial hypertension. Anatol J. Cardiol 15(3):249-254 (2015).

Matos Casano, Harold A. et al. Six-Minute Walk Test. In: StatPearls [Internet]. Treasure Island (FL): StatPearls Publishing; Jan. 2024. Available from: https://www.ncbi.nlm.nih.gov/books/NBK576420/ [Updated Aug. 14, 2023] (pp. 1-7).

\* cited by examiner

METHODS OF TREATING PAH WITH COMBINATIONS OF RALINEPAG AND OTHER AGENTS

CROSS-REFERENCE TO RELATED APPLICATIONS

This application is a U.S. National Stage entry of International Application No. PCT/US2017/061116, filed Nov. 10, 2017, which claims the benefit of priority from U.S. Provisional Application No. 62/420,515, filed Nov. 10, 2016 and U.S. Provisional Application No. 62/530,533, filed Jul. 10, 2017, all of which are hereby incorporated by reference in their entirety.

FIELD OF THE INVENTION

The present invention relates to methods of treatment and combinations of ralinepag (also known as APD811) and cAMP-elevating agents or cGMP-elevating agents (e.g., soluble guanylate cyclase (sGC) stimulators such as riociguat), combinations of ralinepag and prostanoids (e.g., treprostinil), or combinations of ralinepag and prostacyclin receptor agonists which are useful for the treatment of pulmonary arterial hypertension (PAH); idiopathic PAH; familial PAH; PAH associated with: a collagen vascular disease, a congenital heart disease, portal hypertension, HIV infection, ingestion of a drug or toxin, hereditary hemorrhagic telangiectasia, splenectomy, pulmonary veno-occlusive disease (PVOD) or pulmonary capillary hemangiomatosis (PCH); PAH with significant venous or capillary involvement; platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherothrombosis; asthma or a symptom thereof; a diabetic-related disorder such as diabetic peripheral neuropathy, diabetic nephropathy or diabetic retinopathy; glaucoma or another disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; atherosclerosis; acne; type 1 diabetes; type 2 diabetes; sepsis; and chronic obstructive pulmonary disorder (COPD).

BACKGROUND

Pulmonary arterial hypertension (PAH) is a highly proliferative, inflammatory vascular remodeling disease leading to right heart failure and death. The pulmonary pharmacology of prostacyclin (epoprostenol) remains an area of considerable interest because of the use of epoprostenol and its stable mimetics in the treatment of PAH. Prostanoid compounds iloprost (i.v., inhaled) and treprostinil (subcutaneous, i.v, inhaled) are extensively used in the treatment of this disease. Given the complications posed by the above delivery routes, successful oral therapies are being sought for use earlier in the disease process with improved efficacy and/or outcome with this class of compounds (McLaughlin et al., 2009; Clapp & Gurung, 2015).

Oral beraprost (which contains several isomers of beraprost), is only licensed in Japan and Korea (Vachiery, 2011) and appears to have limited efficacy clinically (Barst et al., 2003). Oral treprostinil has only recently received FDA approval, though it is not clear at present whether the oral formulation will approach the clinical efficacy seen with either subcutaneous or i.v. administration methods (Tapson et al., 2013). Selexipag (NS-304), is an oral, non-prostanoid IP receptor agonist (Skoro-Sajer & Lang, 2014; Sitbon et al., 2015). It is a non-prostanoid, diphenylpyrazine derivative whose active metabolite, MRE-269 (also known as ACT-333679) is reported to be a highly selective IP receptor agonist (Kuwano et al., 2007). MRE-269 potently binds to the human IP receptor ($K_i$=20 nM), while selexipag has much less affinity at this receptor ($K_i$=260 nM); both however have little binding affinity for other prostanoid receptors ($K_i$≥2.6 µM).

In normal human pulmonary arterial smooth muscle cells (PASMCs), the IP receptor, through the generation of cyclic AMP (cAMP) appears to be the main mediator of the antiproliferative responses to treprostinil and iloprost (Wharton et al., 2000; Clapp et al., 2002; Falcetti et al., 2010). In contrast, in human PASMCs isolated from IPAH patients, neither the IP receptor nor cAMP appeared to be the main mediator underpinning the antiproliferative effects of treprostinil and iloprost, at least at the concentrations studied (Falcetti et al., 2010). Thus, there is no clear indication in the scientific literature as to how efficacious drugs that are selective for the IP receptors will be in a disease where the IP receptor expression is lower, as it is in patients with PAH (Lai et al., 2008; Falcetti et al., 2010).

Ralinepag (2-(((1r,4r)-4-(((4-chlorophenyl)(phenyl)carbamoyloxy)methyl)cyclohexyl) methoxy)acetic acid, also known as APD811) is an orally available, non-prostanoid prostacyclin (IP) receptor agonist for treating various conditions as described herein, for example vasospastic diseases such as PAH. Ralinepag is disclosed in US Patent Publication No. 2011/0053958, herein incorporated by reference in its entirety for all purposes.

Ralinepag is currently being evaluated as an oral monotherapy for treating conditions such as PAH. In a recent clinical trial, patients underwent titration of ralinepag in order to establish the tolerable dose. Potential methods for administering ralinepag comprise dosing at an initially low dose, once or twice daily, then escalating the dose over a period of, typically, weeks, by stepwise increase of the ralinepag dose and/or dosing frequency until the highest tolerable daily dose is achieved.

The need for dose escalation can delay delivery of the desired highest tolerable therapeutic dose to the patient, thereby delaying potential clinical benefits. In addition, the need to administer multiple daily doses is inconvenient and can reduce patient compliance. It would therefore be desirable to provide methods of administration of ralinepag in which dose titration is reduced or eliminated, and/or the need for multiple daily doses is reduced or eliminated. In addition, it would be desirable to provide methods of enhancing the therapeutic effects of ralinepag and/or a coadministered compound while minimizing side effects, for example by achieving clinical efficacy at a lower dose of one or more compound. Such a method would provide clear clinical benefits, as well as enhance patient compliance. The present disclosure provides improved treatments and methods of administering ralinepag, particularly for treating PAH and related conditions.

SUMMARY OF THE INVENTION

In its various embodiments, the present invention is directed to a method of decreasing cell proliferation (e.g., of pulmonary arterial smooth muscle cells (PASMCs)), in a patient in need thereof, comprising administering a therapeutically effective amount of ralinepag, or a pharmaceutically acceptable salt, hydrate, or solvate thereof, in combination with a therapeutically effective amount of one or more of a cGMP elevating agent, a cAMP elevating agent, a prostanoid, or a prostacyclin receptor agonist.

In various embodiments, the one or more cGMP or cAMP elevating agents is a soluble guanylate cyclase modulator.

In various embodiments, ralinepag is administered in combination with one or more cGMP elevating agents, for example any of the cGMP elevating agents disclosed herein.

In various embodiments, ralinepag is administered in combination with one or more cAMP elevating agents, for example any of the cAMP elevating agents disclosed herein.

In various embodiments, ralinepag is administered in combination with a prostanoid, for example any of the prostanoids disclosed herein.

In various embodiments, coadministration of ralinepag with one or more cGMP elevating agents, cAMP elevating agents, prostanoids, or prostacyclin receptor agonists does not require titration, e.g., of ralinepag upon initiating said coadministration method. In various embodiments, coadministration of ralinepag with one or more cGMP elevating agents, cAMP elevating agents, prostanoids, or prostacyclin receptor agonists does not require titration, e.g., of the one or more cGMP elevating agents, cAMP elevating agents, prostanoids, or prostacyclin receptor agonists. For example, in some embodiments, coadministration of ralinepag with riociguat does not require titration of ralinepag. In some embodiments, coadministration of ralinepag with riociguat does not require titration of riociguat.

In various embodiments, coadministration of ralinepag with one or more cGMP elevating agent, cAMP elevating agent, prostanoid, or prostacyclin receptor agonist does not require as many steps as a standard titration scheme (for example, the titration scheme provided on a product label for the monotherapy) for one or both of the coadministered agents. In various embodiments, coadministration of ralinepag with one or more cGMP elevating agent, cAMP elevating agent, prostanoid, or prostacyclin receptor agonist allows for a higher initial dose that a standard titration scheme (for example, the titration scheme provided on a product label for the monotherapy) for one or both of the coadministered agents.

In various embodiments, the daily dose of ralinepag in combination with the one or more of the cGMP elevating agent, cAMP elevating agent, or prostanoid is at least about 0.01 mg, 0.02 mg, 0.03 mg, 0.04 mg, 0.05 mg, 0.06 mg, 0.07 mg, 0.08 mg, 0.09 mg, 0.1 mg, 0.11 mg, 0.12 mg, 0.13 mg, 0.14 mg, 0.15 mg, 0.16 mg, 0.17 mg, 0.18 mg, 0.19 mg, 0.2 mg, 0.21 mg, 0.22 mg, 0.23 mg, 0.24 mg, 0.25 mg, 0.26 mg, 0.27 mg, 0.28 mg, 0.29 mg, or 0.3 mg (dose equivalent) less than the equivalent therapeutic amount of ralinepag in the absence of coadministration of one or more cGMP elevating agent, cAMP elevating agent, or prostanoid.

In various embodiments, coadministration of ralinepag with one or more cGMP elevating agents, cAMP elevating agents, prostanoids, or prostacyclin receptor agonists provides a reduced daily dose of ralinepag and/or cGMP elevating agent, cAMP elevating agent, prostanoid, or prostacyclin receptor agonist relative to daily doses of ralinepag and/or cGMP elevating agent, cAMP elevating agent, prostanoid, or prostacyclin receptor agonist that provides an equivalent clinical effect.

In various embodiments, ralinepag is coadministered with one or more of riociguat, vericiguat, ataciguat, nelociguat, lificiguat, IW-1701, IW-1973, IWP-051, IWP-121, IWP-427, IWP-953, BAY-60-2770, A-344905; A-350619, A-778935, BI-684067, BI-703704, BAY-41-2272, and BAY-41-8543.

In various embodiments, the amount of ralinepag is, or is about, 0.02, 0.025 0.04, 0.05, 0.06, 0.075, 0.08, 0.1, 0.12, 0.125, 0.14, 0.15, 0.16, 0.175, 0.18, 0.2, 0.22, 0.24, 0.25, 0.26, 0.275, 0.28, 0.3, 0.32, 0.325, 0.34, 0.35, 0.36, 0.375, 0.38, 0.4, 0.42, 0.44, 0.45, 0.46, 0.48, 0.5, 0.52, 0.54, 0.56, 0.58, 0.6, 0.625, 0.65, 0.675, 0.7, 0.725, 0.75, 0.775, 0.8, 0.825, 0.85, 0.875, 0.9, 0.925, 0.95, 0.975, or 1.0 mg, or a range of any two such amounts. For example, in various embodiments, the amount of ralinepag is, or is about, 0.05-0.6 mg. In various embodiments, the amount of ralinepag is, or is about, 0.05-0.75 mg.

In various embodiments, the amount of ralinepag is, or is about, 0.02, 0.025, 0.04, 0.05, 0.06, 0.075, 0.08, 0.1, 0.12, 0.125, 0.14, 0.15, 0.16, 0.175, 0.18, 0.2, 0.22, 0.24, 0.25, 0.26, 0.275, 0.28, 0.3, 0.32, 0.325, 0.34, 0.35, 0.36, 0.375, 0.38, 0.4, 0.42, 0.44, 0.45, 0.46, 0.48, 0.5, 0.52, 0.54, 0.56, 0.58, 0.6, 0.625, 0.65, 0.675, 0.7, 0.725, 0.75, 0.775, 0.8, 0.825, 0.85, 0.875, 0.9, 0.925, 0.95, 0.975, or 1.0 mg daily, or a range of any two such amounts. For example, in various embodiments, the amount of ralinepag is, or is about, 0.05-0.6 mg daily.

In various embodiments, the amount of ralinepag is, or is about, 0.02, 0.025, 0.04, 0.05, 0.06, 0.075, 0.08, 0.1, 0.12, 0.125, 0.14, 0.15, 0.16, 0.175, 0.18, 0.2, 0.22, 0.24, 0.25, 0.26, 0.275, 0.28, 0.3, 0.32, 0.325, 0.34, 0.35, 0.36, 0.375, 0.38, 0.4, 0.42, 0.44, 0.45, 0.46, 0.48, 0.5, 0.52, 0.54, 0.56, 0.58, 0.6 mg, 06.25, 0.65, 0.675, 0.7, 0.725, 0.75, 0.775, 0.8, 0.825, 0.85, 0.875, 0.9, 0.925, 0.95, 0.975, or 1.0 mg once daily (QD), or a range of any two such amounts. For example, in various embodiments, the amount of ralinepag is, or is about, 0.05-0.6 mg QD.

In various embodiments, the amount of ralinepag is, or is about, 0.01, 0.02, 0.025, 0.03, 0.04, 0.05, 0.06, 0.07, 0.075, 0.08, 0.09, 0.1, 0.11, 0.12, 0.125, 0.13, 0.14, 0.15, 0.16, 0.17, 0.175, 0.18, 0.19, 0.2, 0.21, 0.22, 0.23, 0.24, 0.25, 0.26, 0.27, 0.275, 0.28, 0.29, 0.3, 0.325, 0.35, 0.375, 0.4, 0.425, 0.45, 0.475, or 0.5 mg twice daily (BID), or a range of any two such amounts. For example, in various embodiments, the amount of ralinepag is, or is about, 0.05-0.3 mg BID.

In various embodiments, the amount of ralinepag is, or is about, 0.01, 0.02, 0.025, 0.03, 0.04, 0.05, 0.06, 0.07, 0.075, 0.08, 0.09, or 0.1 mg every other day.

In various embodiments, the amount of riociguat is, or is about, 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5 mg, or a range of any two such amounts. For example, in various embodiments, the amount of riociguat is, or is about, 0.5 to 2.5 mg.

In various embodiments, the amount of riociguat is, or is about, 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5 mg daily, or a range of any two such amounts. For example, in various embodiments, the amount of riociguat is, or is about, 0.5 to 2.5 mg daily.

In various embodiments, the amount of riociguat is, or is about, 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5 mg once daily (QD), or a range of any two such amounts. For example, in various embodiments, the amount of riociguat is, or is about, 0.5 to 2.5 mg once daily. In various embodiments, the riociguat is administered twice daily. In various embodiments, the riociguat is administered three times daily.

In various embodiments, the amount of riociguat is, or is about, 0.25, 0.5, 0.75, 1, 1.25, 1.5, 1.75, 2, 2.25, or 2.5 mg twice daily (BID), or a range of any two such amounts.

In various embodiments, the amount of riociguat is 0.5, 1, 1.5, 2, or 2.5 mg three times daily (TID), or a range of any two such amounts.

In various embodiments, the amount of riociguat is less than or equal to 0.25, 0.5, 0.75, 1, 1.25, 1.5, 1.75, 2, 2.25, 2.5, 2.75, 3, 3.25, 3.5, 3.75, 4, 4.25, 4.5, 4.75, or 5 mg.

In various embodiments, the riociguat is in an inhaled form. In various embodiments, the riociguat is in an intravenous form. In various embodiments, the riociguat is in an oral form.

In various embodiments, the amount of treprostinil is, or is about, 0.1, 0.125, 0.2, 0.25, 0.3, 0.35, 0.4, 0.45, 0.5, 0.6, 0.65, 0.7, 0.75, 0.8, 0.85, 0.9, 0.95, 1, 0.25, 0.5, 1.75, 2, 2.25, 2.5, 2.75, 3, 3.25, 3.5, 3.75, 4, 4.25, 4.5, 4.75, 5, 6, 7, 8, 9, or 10 mg, or a range of any two such amounts. For example, in various embodiments, the amount of treprostinil is, or is about, 0.125-5 mg.

In various embodiments, the amount of treprostinil is, or is about, 1, 2.5, 3, 4, 5, 6, 7, 7.5, 8, 9, 10, 11, 12, 12.5, 13, 14, 15, 16, 17, 17.5, 18, 19, 20, or 25 mg/ml, or a range of any two such amounts. In various embodiments, the amount of treprostinil is 1-10 mg/ml in an IV subcutaneous form.

In various embodiments, the amount of treprostinil is, or is about, 0.1, 0.2, 0.25, 0.3, 0.4, 0.5, 0.6, 0.7, 0.75, 0.8, 0.9, or 1 mg/ml, or a range of any two such amounts. In various embodiments, the amount of treprostinil is 0.6 mg/ml in an inhaled form.

In various embodiments, the amount of treprostinil is less than or equal to 0.1, 0.125, 0.2, 0.25, 0.3, 0.35, 0.4, 0.45, 0.5, 0.6, 0.65, 0.7, 0.75, 0.8, 0.85, 0.9, 0.95, 1, 0.25, 0.5, 1.75, 2, 2.25, 2.5, 2.75, 3, 3.25, 3.5, 3.75, 4, 4.25, 4.5, 4.75, or 5 mg. In various embodiments, the amount of treprostinil is less than or equal to 1, 2.5, 3, 4, 5, 6, 7, 7.5, 8, 9, or 10 mg/ml. In various embodiments, the amount of treprostinil is less than or equal to 0.1, 0.2, 0.25, 0.3, 0.4, 0.5, or 0.6 mg/ml.

In various embodiments, the treprostinil is in an inhaled form. In some embodiments, the treprostinil is in an injectable form. In various embodiments, the treprostinil is in an intravenous form. In various embodiments, the treprostinil is in an IV subcutaneous form. In various embodiments, the treprostinil is in an oral form. In various embodiments, the treprostinil is in a transdermal form. In various embodiments, the treprostinil is in a transdermal patch. In various embodiments, the treprostinil is administered once daily. In various embodiments, the treprostinil is administered twice daily. In various embodiments, the treprostinil is administered three times daily.

In some embodiments, the therapeutically effective amount of ralinepag is a starting dose. In some embodiments, the therapeutically effective amount of ralinepag is a highest tolerated dose. In some embodiments, the therapeutically effective amount of ralinepag is a maximum dose. In some embodiments, the therapeutically effective amount of ralinepag is a maximum tolerated dose. In some embodiments, the therapeutically effective amount of ralinepag is a maintenance dose.

In some embodiments, the starting dose is for a patient. In some embodiments, the starting dose is for a patient population. In some embodiments, the highest tolerated dose is for a patient. In some embodiments, the highest tolerated dose is for a patient population. In some embodiments, the maximum dose is for a patient. In some embodiments, the maximum dose is for a patient population. In some embodiments, the maximum tolerated dose is for a patient. In some embodiments, the maximum tolerated dose is for a patient population. In some embodiments, the maintenance dose is for a patient. In some embodiments, the maintenance dose is for a patient population.

In some embodiments, the starting dose of ralinepag is selected from, or from about, 0.01, 0.02, 0.025, 0.03, 0.04, 0.05, 0.06, 0.07, 0.075, 0.08, 0.09, or 0.1 mg daily. In some embodiments, the starting dose of ralinepag is 0.01 mg daily. In some embodiments, the starting dose of ralinepag is 0.02 mg daily. In some embodiments, the starting dose of ralinepag is 0.05 mg daily.

In some embodiments, the dose of ralinepag is increased at weekly intervals by 0.05 mg daily to the highest tolerated dose up to 0.8 mg daily.

In some embodiments, the dose of ralinepag is increased at weekly intervals. In some embodiments, the dose of ralinepag is increased at bimonthly intervals.

In some embodiments, the dose of ralinepag is increased by an amount selected from 0.02 mg, 0.05 mg, and 0.75 mg and 0.1 mg daily.

In some embodiments, the dose of ralinepag is increased at weekly intervals by an amount selected from 0.02 mg, 0.05 mg, and 0.75 mg, and 0.1 mg daily.

In some embodiments, the highest tolerated dose of ralinepag is selected from, or from about, 0.4 mg, 0.45 mg, 0.5 mg, 0.6 mg, 0.65 mg, 0.7 mg, 0.75 mg, 0.8 mg, 0.85 mg, 0.9 mg, 0.95 mg, and 1.0 mg daily. In some embodiments, the highest tolerated dose of ralinepag is 0.6 mg daily. In some embodiments, the highest tolerated dose of ralinepag is 0.75 mg daily. In some embodiments, the highest tolerated dose of ralinepag is 0.8 mg daily. In some embodiments, the highest tolerated dose of ralinepag is from 0.4 to 1.0 mg daily. In some embodiments, the highest tolerated dose of ralinepag is from 0.6 to 1.0 mg daily. In some embodiments, the highest tolerated dose of ralinepag is from 0.6 to 0.8 mg daily. In some embodiments, the highest tolerated dose of ralinepag is from 0.65 to 1.0 mg daily. In some embodiments, the highest tolerated dose of ralinepag is from 0.65 to 0.8 mg daily. In some embodiments, the highest tolerated dose of ralinepag is greater than 0.4 mg daily. In some embodiments, the highest tolerated dose of ralinepag is greater than 0.6 mg daily.

In some embodiments, the maximum dose of ralinepag is selected from, or from about, 0.4 mg, 0.45 mg, 0.5 mg, 0.6 mg, 0.65 mg, 0.7 mg, 0.75 mg, 0.8 mg, 0.85 mg, 0.9 mg, 0.95 mg, and 1.0 mg daily. In some embodiments, the maximum dose of ralinepag is 0.6 mg daily. In some embodiments, the maximum dose of ralinepag is 0.75 mg daily. In some embodiments, the maximum dose of ralinepag is 0.8 mg daily. In some embodiments, the maximum dose of ralinepag is from 0.4 to 1.0 mg daily. In some embodiments, the maximum dose of ralinepag is from 0.6 to 1.0 mg daily. In some embodiments, the maximum dose of ralinepag is from 0.6 to 0.8 mg daily. In some embodiments, the maximum dose of ralinepag is from 0.65 to 1.0 mg daily. In some embodiments, the maximum dose of ralinepag is from 0.65 to 0.8 mg daily. In some embodiments, the maximum dose of ralinepag is greater than 0.4 mg daily. In some embodiments, the maximum dose of ralinepag is greater than 0.6 mg daily.

In some embodiments, the maximum tolerated dose of ralinepag is selected from, or from about, 0.4 mg, 0.45 mg, 0.5 mg, 0.6 mg, 0.65 mg, 0.7 mg, 0.75 mg, 0.8 mg, 0.85 mg, 0.9 mg, 0.95 mg, and 1.0 mg daily. In some embodiments, the maximum tolerated dose of ralinepag is 0.6 mg daily. In some embodiments, the maximum tolerated dose of ralinepag is 0.75 mg daily. In some embodiments, the maximum tolerated dose of ralinepag is 0.8 mg daily. In some embodiments, the maximum tolerated dose of ralinepag is 0.75 mg daily. In some embodiments, the maximum tolerated dose of ralinepag is 0.8 mg daily. In some embodiments, the maximum tolerated dose of ralinepag is from 0.4 to 1.0 mg daily. In some embodiments, the maximum tolerated dose of ralinepag is from 0.6 to 1.0 mg daily. In some embodiments, the maximum tolerated dose of ralinepag is from 0.6 to 0.8 mg daily. In some embodiments, the maximum tolerated dose of ralinepag is from 0.65 to 1.0 mg daily. In some embodiments, the maximum tolerated dose of ralinepag is from 0.65 to 0.8 mg daily. In some embodiments, the maximum tolerated dose of ralinepag is greater than 0.4 mg daily. In some embodiments, the maximum tolerated dose of ralinepag is greater than 0.6 mg daily.

In some embodiments, the maximum dose of ralinepag in a dosage form is selected from, or from about, 0.4 mg, 0.45 mg, 0.5 mg, 0.6 mg, 0.65 mg, 0.7 mg, 0.75 mg, 0.8 mg, 0.85 mg, 0.9 mg, 0.95 mg, and 1.0 mg. In some embodiments, the maximum dose of ralinepag in a dosage form is 0.6 mg. In some embodiments, the maximum dose of ralinepag in a dosage form is 0.75 mg. In some embodiments, the maximum dose of ralinepag in a dosage form is 0.8 mg. In some embodiments, the maximum dose of ralinepag is from 0.4 to 1.0 mg daily. In some embodiments, the maximum dose of ralinepag is from 0.6 to 1.0 mg daily. In some embodiments, the maximum dose of ralinepag is from 0.6 to 0.8 mg daily. In some embodiments, the maximum dose of ralinepag is from 0.65 to 1.0 mg daily. In some embodiments, the maximum dose of ralinepag is from 0.65 to 0.8 mg daily. In some embodiments, the maximum dose of ralinepag is greater than 0.4 mg daily. In some embodiments, the maximum dose of ralinepag is greater than 0.6 mg daily.

In some embodiments, the maintenance dose of ralinepag is selected from, or from about, 0.01 mg, 0.02 mg, 0.025 mg, 0.03 mg, 0.04 mg, 0.05 mg, 0.06 mg, 0.065 mg, 0.07 mg, 0.075 mg, 0.08 mg, 0.09 mg, 0.1 mg, 0.12 mg, 0.15 mg, 0.16 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, and 1.0 mg daily. In some embodiments, the maintenance dose of ralinepag is from 0.4 to 1.0 mg daily. In some embodiments, the maintenance dose of ralinepag is from 0.6 to 1.0 mg daily. In some embodiments, the maintenance dose of ralinepag is from 0.6 to 0.8 mg daily. In some embodiments, the maintenance dose of ralinepag is from 0.65 to 1.0 mg daily. In some embodiments, the maintenance dose of ralinepag is from 0.65 to 0.8 mg daily. In some embodiments, the maintenance dose of ralinepag is determined by tolerability. In some embodiments, the maintenance dose of ralinepag is greater than 0.4 mg daily. In some embodiments, the maintenance dose of ralinepag is greater than 0.6 mg daily.

In some embodiments, in a patient who receives a dose of ralinepag that cannot be tolerated, the dose of ralinepag is reduced to the previous tolerated dose. In some embodiments, the previous tolerated dose is the maximum tolerated dose for the patient.

In some embodiments, the amount of ralinepag is adjusted to account for a difference in bioequivalence between an immediate-release form and an extended-release form. For example, in some embodiments, 0.8 mg of ralinepag in an extended-release dosage form is provided to equate two 0.3 mg immediate-release dosage forms of ralinepag, where the extended-release dosage form has less than 100% bioequivalence with the immediate-release dosage forms.

In some embodiments, a therapeutically effective amount is suitable for administration once daily. In some embodiments, a therapeutically effective amount is suitable for administration twice daily. In some embodiments, a therapeutically effective amount is administered once daily. In some embodiments, a therapeutically effective amount is administered twice daily.

In various embodiments, ralinepag is titrated. In various embodiments, riociguat is titrated. In various embodiments, both ralinepag and riociguat are titrated. In some embodiments, riociguat is titrated in accordance with a product label approved by a regulatory authority (such as the U.S. FDA, see, ADEMPAS® label), which is incorporated herein by reference.

In various embodiments, ralinepag is titrated. In various embodiments, treprostinil is titrated. In various embodiments, both ralinepag and treprostinil are titrated. In some embodiments, treprostinil is titrated in accordance with a product label approved by a regulatory authority (such as the U.S. FDA, see, UPTRAVI® label), which is incorporated herein by reference.

In various embodiments, ralinepag is coadministered with one or more of treprostinil, iloprost, cisaprost, and epoprostenol.

In various embodiments, the coadministration methods disclosed herein are useful for treating PAH, for example idiopathic PAH; heritable PAH; familial PAH; PAH associated with: a collagen vascular disease, a congenital heart disease, a congenital heart disease with repaired shunts, portal hypertension, connective tissue disease, HIV infection, ingestion of a drug or toxin, hereditary hemorrhagic telangiectasia, splenectomy, pulmonary veno-occlusive disease (PVOD), or pulmonary capillary hemangiomatosis (PCH); and PAH with significant venous or capillary involvement. In some embodiments, the coadministration methods disclosed herein are useful for treating human subjects with symptomatic PAH. In some embodiments, the coadministration methods disclosed herein are useful for treating human subjects with PAH, WHO Functional Class I. In some embodiments, the coadministration methods disclosed herein are useful for treating human subjects with PAH, WHO Functional Class II. In some embodiments, the coadministration methods disclosed herein are useful for treating human subjects with PAH, WHO Functional Class III. In some embodiments, the coadministration methods disclosed herein are useful for treating human subjects with PAH, WHO Functional Class IV. In some embodiments, the coadministration methods disclosed herein are useful for treating human subjects with PAH, WHO Group I. In certain embodiments, the coadministration methods disclosed herein are useful for treating PAH patients with WHO Functional Class II-III symptoms. In various embodiments, the coadministration methods disclosed herein are useful for treating chronic thromboembolic pulmonary hypertension (CTEPH). In various embodiments, the coadministration methods disclosed herein are useful for treating persistent/recurrent CTEPH (WHO Group 4) after surgical treatment. In various embodiments, the coadministration methods disclosed herein are useful for treating inoperable CTEPH to improve exercise capacity and/or WHO functional class. In various embodiments, the coadministration methods disclosed herein are useful for treating PAH (WHO Group 1) to improve exercise capacity. In various embodiments, the coadministration methods disclosed herein are useful for improving WHO functional class and/or to delay clinical worsening. In various embodiments, the coadministration methods disclosed herein are useful for delaying disease progression and/or reducing the risk of hospitalization for PAH.

DETAILED DESCRIPTION OF THE INVENTION

Figure 1A:
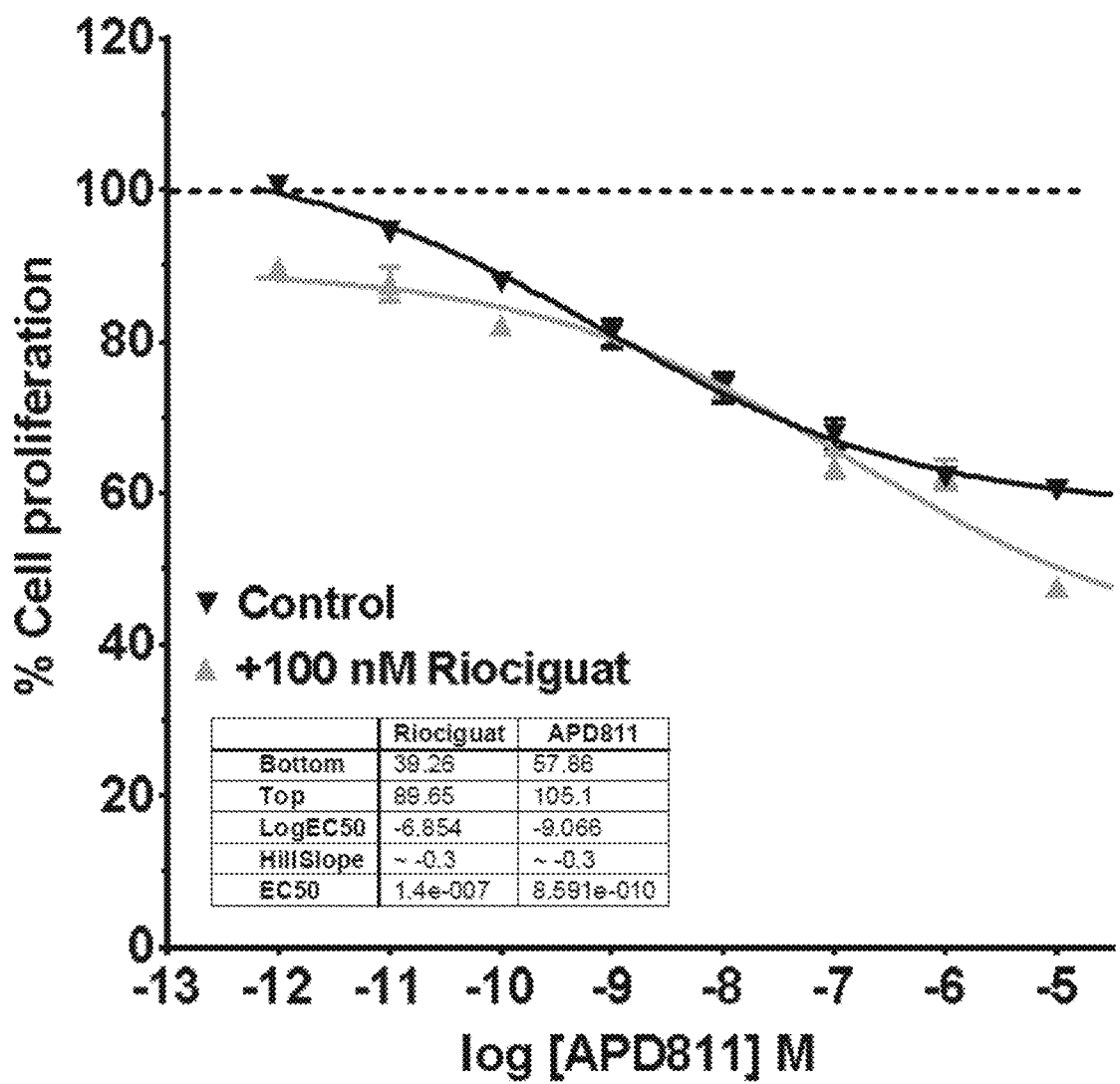
FIGS. 1A-1F show antiproliferative effects of ralinepag in combination with 100 nM riociguat. Growth arrested cells were incubated for 96 hours in human smooth muscle basal medium (SMBM) containing either 9% FBS±0.1% DMSO, FBS plus ralinepag and DMSO in the absence or presence of 100 nM riociguat and SMBM alone (time control). Cell proliferation was normalized to the growth response induced by FBS and DMSO, which were taken as the FBS and DMSO response minus the time control (=100% growth at 4 days). Growth responses induced in presence of ralinepag and solvent±riociguat are shown as % change in cell proliferation relative to the FBS response alone. Data were fit using a variable slope sigmoidal-curve fitting routine in GraphPad and parameters of each fit are shown. Data are from 5 individual patient cell isolates. *=P<0.05, when compared to ralinepag alone; 2 WAY-ANOVA with Bonferroni post hoc test.
Figure 1B:
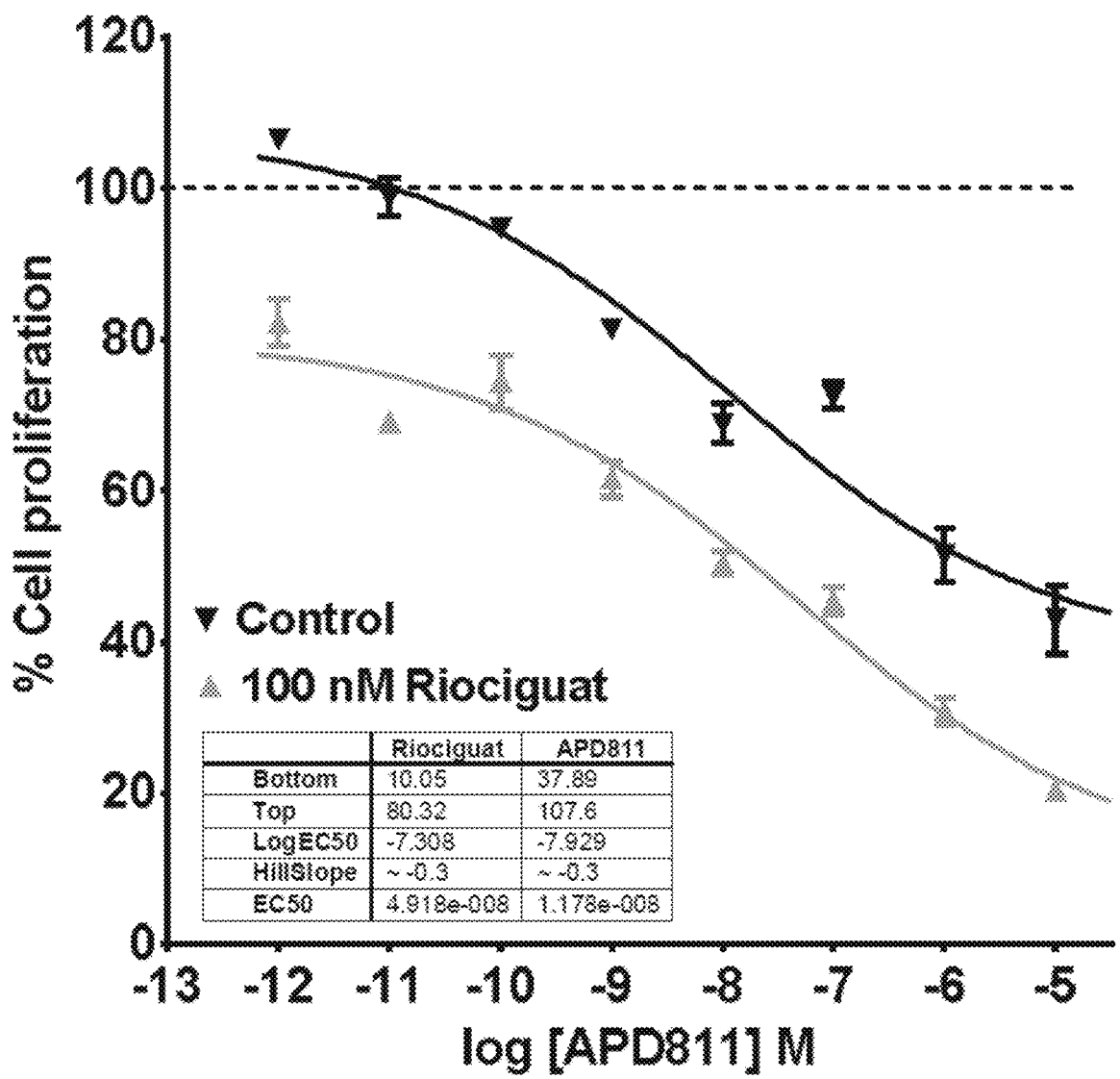
Figure 1C:
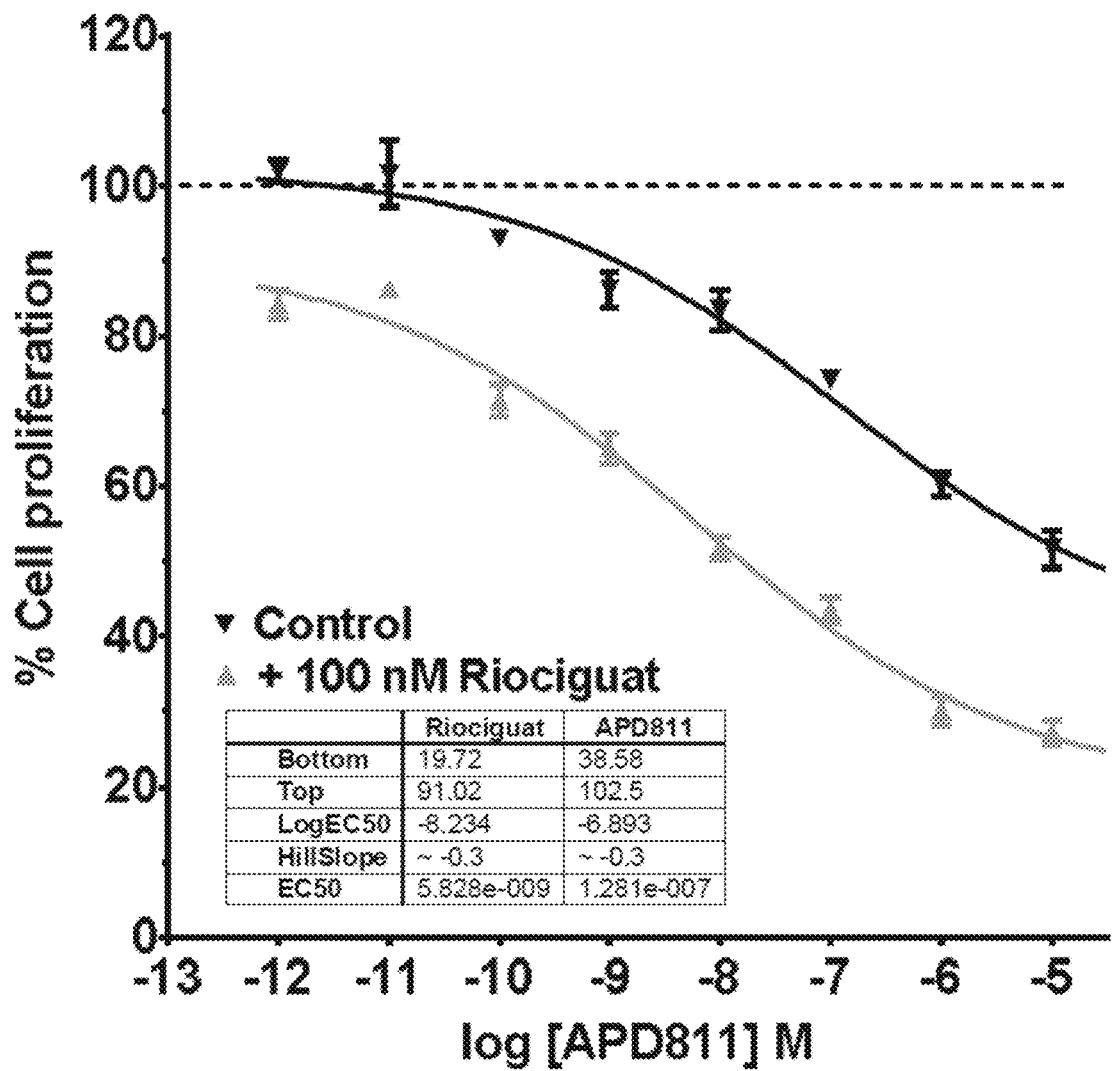
Figure 1D:
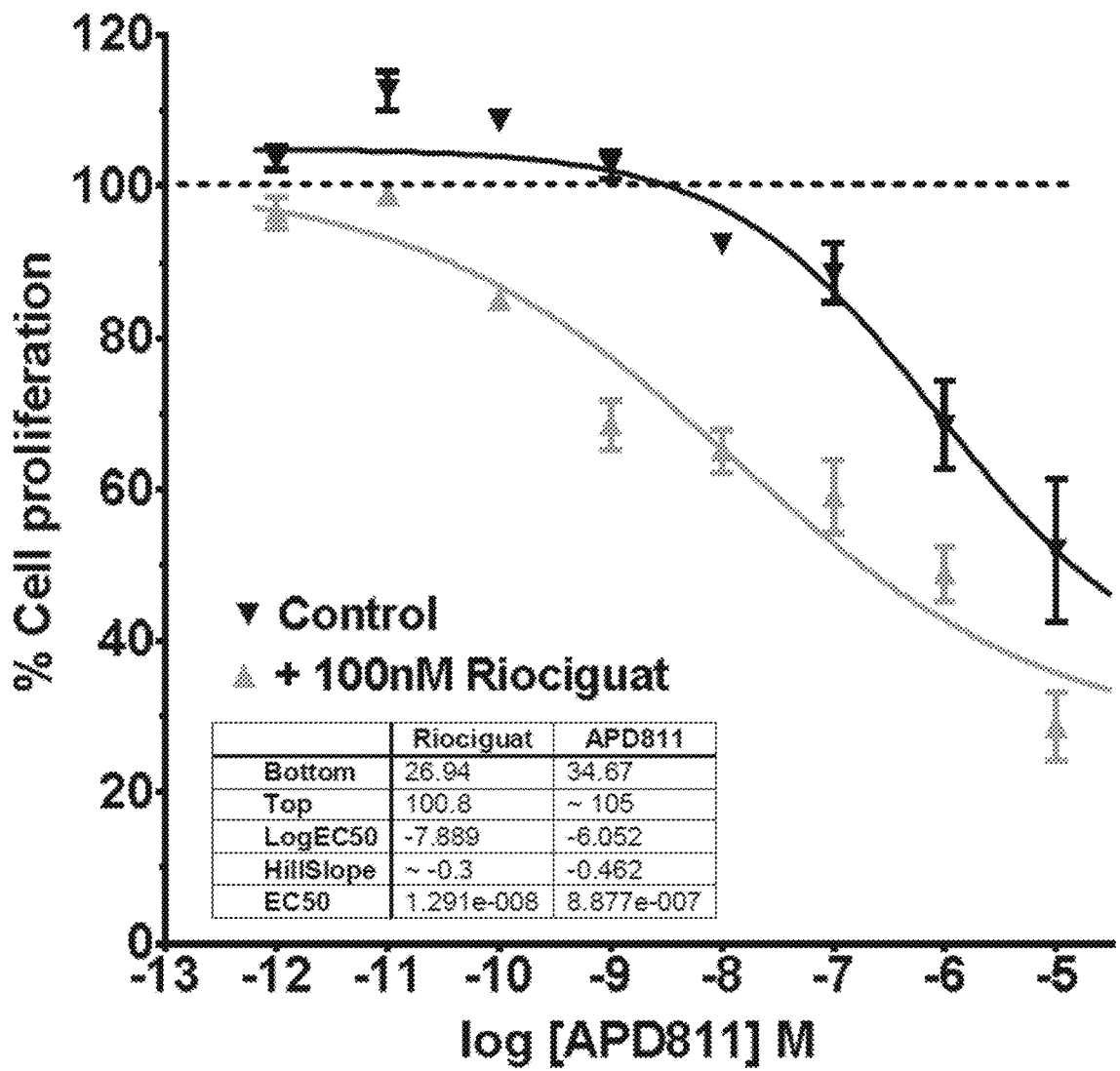
Figure 1E:
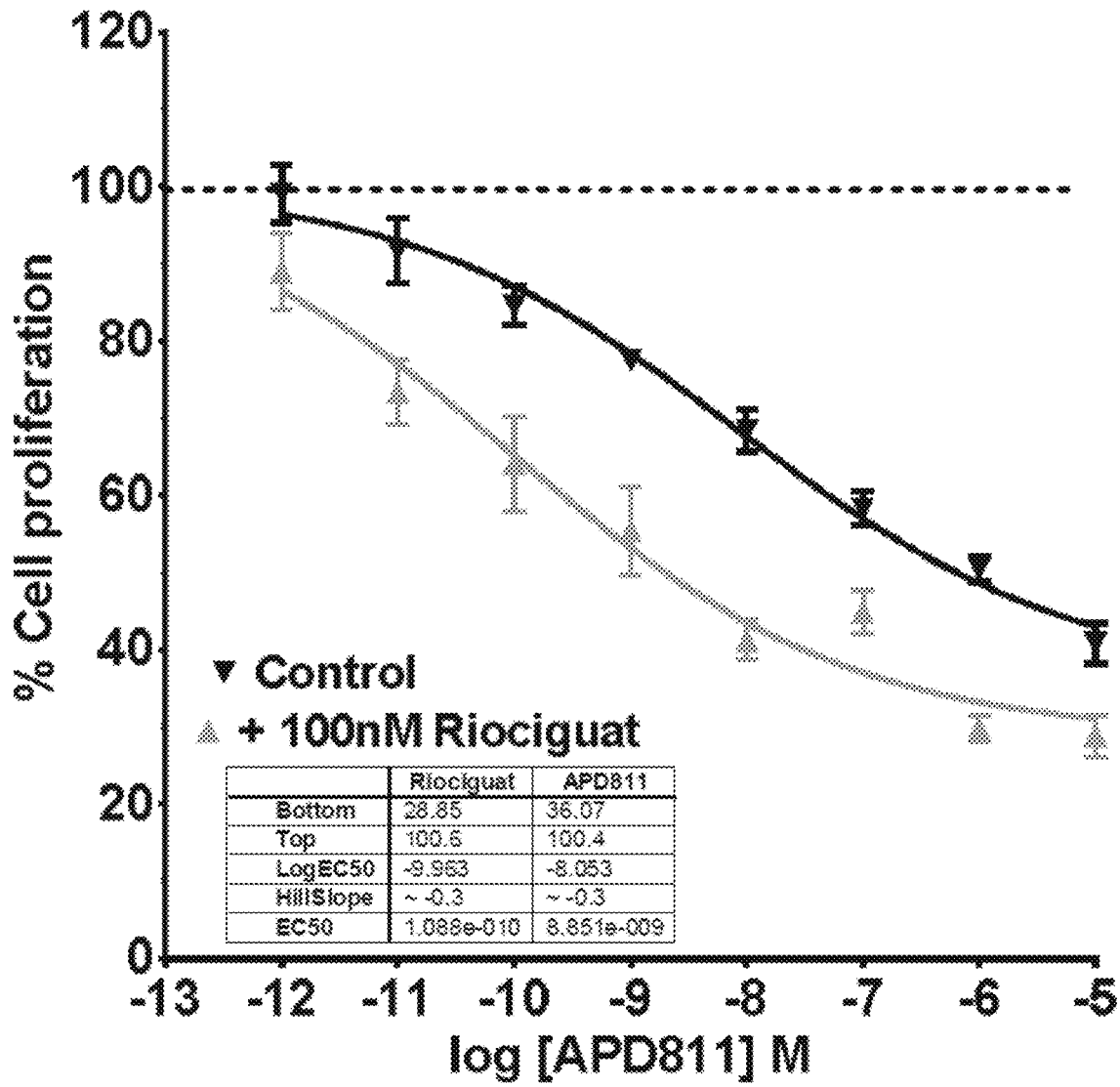
Figure 1F:
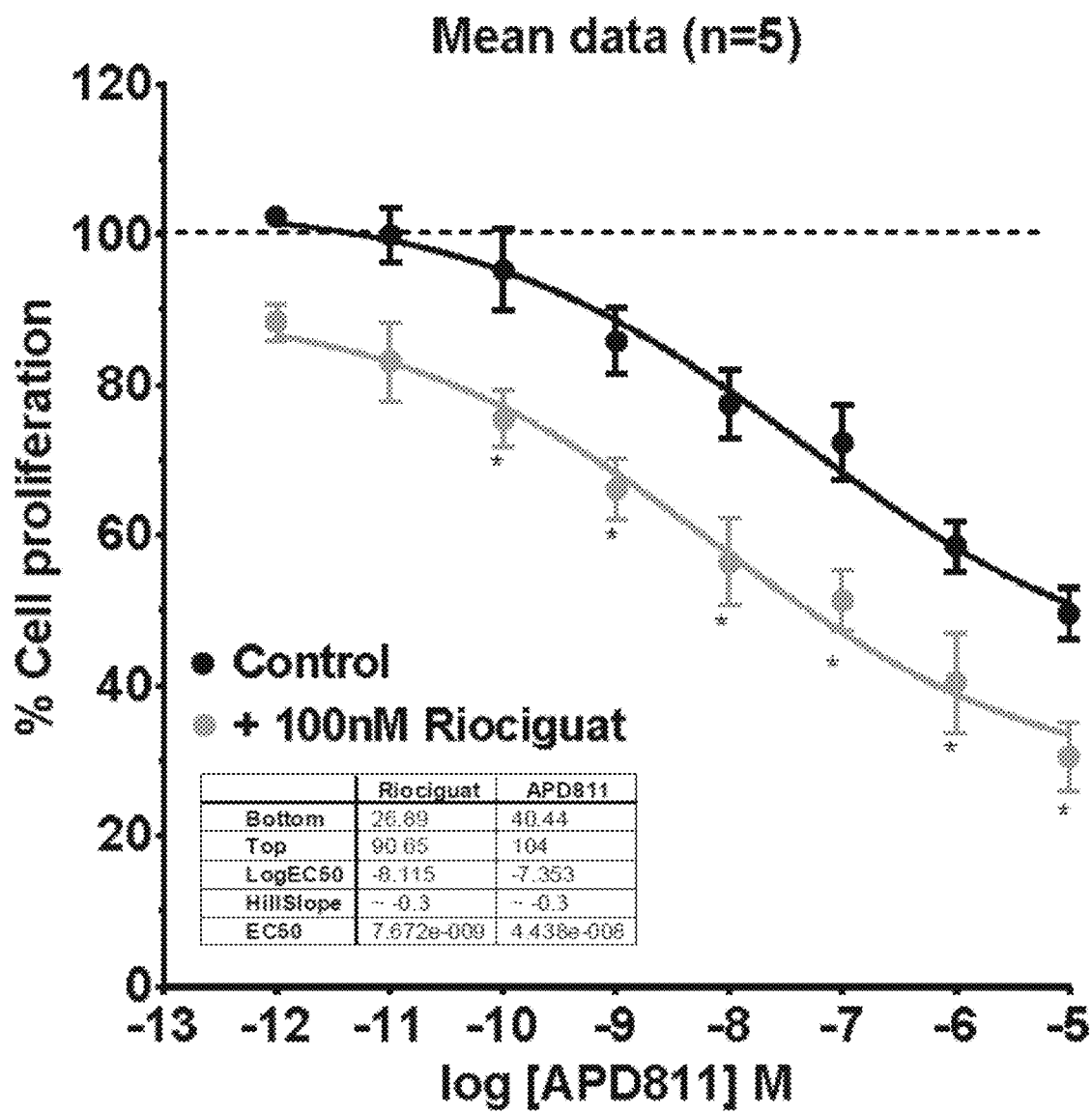

The present disclosure provides improved methods of administering ralinepag to patients in need thereof, particularly for patients suffering from PAH in its many forms, for example idiopathic PAH; familial PAH; PAH associated with: a collagen vascular disease, a congenital heart disease, portal hypertension, HIV infection, ingestion of a drug or toxin, hereditary hemorrhagic telangiectasia, splenectomy, pulmonary veno-occlusive disease (PVOD) or pulmonary capillary hemangiomatosis (PCH); and PAH with significant venous or capillary involvement. The methods of the present disclosure also suitable for treating other conditions such as platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherothrombosis; asthma or a symptom thereof; a diabetic-related disorder such as diabetic peripheral neuropathy, diabetic nephropathy or diabetic retinopathy; glaucoma or another disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; atherosclerosis; acne; type 1 diabetes; type 2 diabetes; sepsis; and chronic obstructive pulmonary disorder (COPD).

Pulmonary arterial hypertension (PAH) is a life-threatening disease characterized by a progressive pulmonary vasculopathy leading to right ventricular hypertrophy. Right heart failure occurs if left untreated. Prostacyclin, which has vasodilatory and antiproliferative effects on the pulmonary vasculature has been found to be low in patients with PAH compared with normal controls. Exogenous administration of prostacyclin or an analog of prostacyclin, e.g., prostanoids such as treprostinil, iloprost, and beraprost have been used to treat PAH. However prostacyclin, treprostinil and iloprost are not orally active and must be administered intravenously. Although beraprost is orally active, it has not been approved in Europe and the US.

Selexipag (2-{4-[(5,6-diphenylpyrazin-2-yl)(propan-2-yl)amino]butoxy}-N-(methanesulfonyl)acetamide) and its free carboxylic acid active metabolite, MRE-269, are also known for treating PAH. However, these drugs are expensive and have a relatively short half-life ranging from ~8, 3-4, and 0.5 hours, respectively in vivo (Kuwano et al., 2007; Clapp & Gurung, 2015). In contrast, and irrespective of the dose, ralinepag has a relatively long plasma half-life. Thus, ralinepag has the potential to provide improved therapeutic effectiveness in treating PAH (and related conditions as described herein) compared to known therapeutic agents.

The synthesis of ralinepag, and pharmaceutically acceptable salts, hydrates, polymorphs and solvates thereof, and a general description of pharmaceutical formulations and methods of treatment are disclosed in, e.g., U.S. application Ser. No. 12/933,196 (published as US 2011/0053958; issued as U.S. Pat. No. 8,895,776). Methods of treating, including methods of titrating ralinepag are disclosed in PCT/US 2015/056824 (published as WO 2016/065103). This latter application describes in detail various methods of optimizing the dose for a patient in need of treatment with ralinepag. In various embodiments, the initial dose of ralinepag is equivalent to 0.01 mg of the free acid form (referred to as the dose equivalent to 0.01 mg), and is either dosed once per day (QD) or twice per day (BID). If this dose is tolerated, the frequency of dosing is increased in the second week (e.g., from QD to BID dosing), and/or the amount of ralinepag is increased, e.g., from an initial dose equivalent to 0.01 mg BID, in weekly increments of e.g., 0.01 mg (dose equivalent) up to a BID dose of 0.3 mg ralinepag.

As used herein, a patient is said to "tolerate" a dose of a compound such as ralinepag if administration of that dose to the patient does not result in an unacceptable adverse event or combination of adverse events. One of skill in the art will appreciate that tolerance is subjective, and the amount that is tolerable by one patient may be intolerable to a different patient. Typically, tolerance reflects a subjective balance between the clinical benefits of the dose relative to any adverse events. As described herein, "adverse events" refers to undesirable or unwanted clinical symptoms associated with treatment with the compound. With regard to ralinepag, typical adverse events include headache, nausea, vomiting, jaw pain, flushing, abnormal pulse rate, abnormal QT interval, a sitting systolic blood pressure greater than about 160 mmHg, a sitting diastolic blood pressure greater than about 100 mmHg, a systolic blood pressure less than about 90 mmHg, abdominal pain, nosebleed, muscle aches, feelings of warmth, palpitations, dizziness, itching, diarrhea, chest pressure, joint aches, prickling or tingling skin sensations, chest pain, chest discomfort, erythema, or combinations of any of the above.

An "optimized dose" or "optimal dose" refers to a therapeutic dose, typically the highest therapeutic dose of the compound (or pharmaceutically acceptable salts, solvate, hydrates, etc. thereof) which elicits the maximum desired clinical benefits to the patient, while minimizing intolerable side effects (e.g., adverse events). One of skill in the art will recognize that the optimal dose can vary from patient to patient, or even over time for a specific patient.

The need to titrate ralinepag to minimize side effects and identify optimized or optimal dose can be time-consuming. For example, in many embodiments two to as many as about nine weeks of titration (i.e., gradually increasing the dose and/or frequency of dosing, typically on a weekly basis) may be required to identify the optimal dose of ralinepag. During this titration period, the patient can remain at a suboptimal dose for an appreciable period of time, which is undesirable. Given the severity of PAH, it would be highly desirable to achieve the optimal dose as quickly as possible. Furthermore, in order to improve patient compliance, it would be desirable to administer ralinepag on a QD schedule rather than BID dosing schedule.

As described herein, co-administering ralinepag with cGMP or cAMP elevating agents such as riociguat, or co-administering ralinepag with a prostacyclin receptor agonist, or with a prostanoid such as treprostinil or iloprost provides unexpected advantages. Specifically, these combinations provide substantial improvements. In some embodiments, the improvement allows for superior efficacy compared to either monotherapy. In some embodiments, the improvement allows for a reduction in the dosing of ralinepag and/or cAMP elevating agents, cGMP elevating agents, prostacyclin receptor agonists, or prostanoids. Alternatively, or in addition, because such combinations provide substantial improvement, optimal clinical results can be obtained at lower doses of ralinepag and/or the cAMP elevating agents, cGMP elevating agents, prostacyclin receptor agonists, or prostanoids (compared to the respective monotherapies), thereby providing the clinical benefits of a monotherapy treatment method but with reduced side effects. Alternatively, the combinations of the present method can provide both improved clinical benefit and reduced side effects.

The desired clinical benefit can be measured by any clinical metric suitable or used in the art for measuring improvement in a patient. For example, a clinical benefit could be, e.g., an increase in at least 40 meters measured by the "six-minute walk test" (6MWT) according to the American Thoracic Society guidelines for the Six-minute Walk Test disclosed in *Am. J. Respir. Crit. Care Med*. Vol. 166, p. 111-117, 2002; DOI: 10.1164/rccm.166/1/111. "Equivalent" or substantially similar clinical benefit means a clinical benefit measured by conventional clinical metrics, for example as measured by 6MWT, which provides substantially the same result in an otherwise identical patient, or the same patient, when comparing the combination therapy of ralinepag and at least one cAMP elevating agent, cGMP elevating agent, prostacyclin receptor agonist, or prostanoid described herein, compared to an otherwise identical patient (similar physiological characteristics, clinical presentation, and response to ralinepag) experiencing a similar level of adverse events or side effects.

In some embodiments, coadministered ralinepag and at least one cAMP elevating agent, cGMP elevating agent, prostacyclin receptor agonist, or prostanoid as described herein provides an improvement in clinical benefit compared to ralinepag monotherapy using the same or a higher dose of ralinepag. For example, the combination therapy as described herein can exhibit an increase in clinical benefit using the 6MWT metric of at least about 5 m, at least about 10 m, at least about 15 m, at least about 20 m, at least about 25 m, or at least about 30 m compared to the same daily dose administered to an otherwise identical patient using a ralinepag monotherapy (i.e., without coadministered cAMP elevating agent, cGMP elevating agent, prostacyclin receptor agonists, or prostanoids).

Similarly, as described herein, co-administering ralinepag with a cAMP elevating agent, cGMP elevating agent, prostacyclin receptor agonist, or prostanoid, the dose of such cAMP elevating agent, cGMP elevating agent, prostacyclin receptor agonist, or prostanoid can be reduced relative to the amount required to achieve an equivalent therapeutic effect in an otherwise identical patient administered such cAMP elevating agent, cGMP elevating agent, prostacyclin, or prostanoid as a monotherapy (i.e., without ralinepag). For example, as discussed herein, the dose of the respective cAMP elevating agent, cGMP elevating agent, prostacyclin receptor agonist, or prostanoid can be reduced by about 1%, about 5%, about 10%, about 15%, about 20%, about 25%, about 30%, about 35%, about 40%, about 45%, or about 50%, relative to the dose required without ralinepag, while achieving a similar level of clinical efficacy, for example as measured by 6MWT and/or side effect level. Alternatively, the combination of ralinepag and cAMP elevating agent, cGMP elevating agent, prostacyclin receptor agonists, or prostanoid provides an improvement in efficacy, e.g., as measured by 6MWT (at least about 5 m, at least about 10 m, at least about 15 m, at least about 20 m, at least about 25 m, or at least about 30 m) compared to a patient administered similar levels of cAMP elevating agent, cGMP elevating agent, prostanoid, or a prostacyclin receptor agonist without ralinepag.

In one embodiment, when co-administering ralinepag with riociguat, prostacyclin, treprostinil, or iloprost (or other prostanoids), significantly lower doses of ralinepag in the combination therapy can be administered compared to the amount required in a ralinepag monotherapy to achieve the same or substantially similar clinical benefit in otherwise identical patients (or in the same patient). That is, the combination of ralinepag and riociguat, prostacyclin, treprostinil, or iloprost act synergistically, so that the clinical effects of ralinepag are potentiated or enhanced by the coadministration of riociguat, prostacyclin, treprostinil, or iloprost. For example, the daily dose of ralinepag required in the combination therapy described herein can be at least about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.225 mg, 0.25 mg, or 0.275 mg, or 0.3 mg lower than the daily ralinepag dose required in a monotherapy to achieve the equivalent, or substantially the same clinical benefit in an otherwise identical patient (or in the same patient). The daily dose can be provided under a QD or BID dosing protocol.

In other embodiments, when co-administering ralinepag with riociguat, prostacyclin, treprostinil, or iloprost (or other prostanoids), the same dose of ralinepag can be administered in the combination therapy that could be administered in a ralinepag monotherapy. However, in the combination therapy, a substantially improved clinical benefit is provided, e.g., as measured by 6MWT (at least about 5 m, at least about 10 m, at least about 15 m, at least about 20 m, at least about 25 m, or at least about 30 m) with a substantially similar side effect profile (i.e., comparing the combination therapy with monotherapy in otherwise identical patients, or in the same patient).

In still other embodiments, equivalent, or substantially similar clinical benefits are provided by the combination of significantly lower doses of ralinepag and reduced doses of riociguat, prostacyclin, treprostinil, or iloprost (or other prostanoids). For example, the daily dose of ralinepag required in the combination therapy described herein can be at least about 0.01 mg, 0.02 mg, 0.03 mg, 0.04 mg, 0.05 mg, 0.06 mg, 0.07 mg, 0.08 mg, 0.09 mg, 0.1 mg, 0.15 mg, 0.2 mg, 0.225 mg, 0.25 mg, or 0.275 mg, or 0.3 mg lower than the ralinepag dose required in a monotherapy to achieve the same, or substantially the same clinical benefit in an otherwise identical patient (or in the same patient). The daily dose of riociguat, prostacyclin, treprostinil, or iloprost (or other prostanoids) can be reduced by about 1%, about 5%, about 10%, about 15%, about 20%, about 25%, about 30%, about 35%, about 40%, about 45%, or about 50%, relative to the dose required in a monotherapy without ralinepag to achieve the equivalent, or substantially the same clinical benefit in an otherwise identical patient (or in the same patient). For example, the daily dose of riociguat required in the combination therapy described herein can be at least about 0.1 mg, 0.2 mg, 0.3 mg, 0.4 mg, 0.5 mg, 0.6 mg, 0.7 mg, 0.8 mg, 0.9 mg, 1.0 mg, 1.25 mg, 1.5 mg, 1.75 mg, or 2 mg lower than the riociguat dose required for an equivalent clinical benefit and/or adverse event profile. The daily dose can be provided under a QD or BID dosing protocols.

In some embodiments, a therapeutically effective amount of ralinepag is administered contemporaneously with one or more cAMP elevating agent, cGMP elevating agent, prostacyclin receptor agonist, or prostanoid such that therapeutically effective amounts of ralinepag and the one or more cAMP elevating agent, cGMP elevating agent, prostacyclin receptor agonist, or prostanoid are both present within the patient and exerting their therapeutic effects at the same time. Ralinepag can be administered prior to, simultaneously with, or subsequent to the cAMP elevating agent, cGMP elevating agent, prostacyclin receptor agonists, or prostanoid. If both ralinepag and the cAMP elevating agent, cGMP elevating agent, prostacyclin receptor agonists, or prostanoid administered at the same time, they can be administered separately in different dosage forms, or in some embodiments in a combined dosage form. When administered in separate dosage forms, the ralinepag can be administered orally in the form of a tablet or capsule, and the cAMP elevating agent, cGMP elevating agent, prostacyclin receptor agonists, or prostanoid can be administered orally (if oral dosage forms are available or possible) or as an intravenous or subcutaneous dosage form. In some embodiments, the ralinepag can also be administered as an injectable or IV dosage form.

In one embodiment, ralinepag is coadministered with riociguat. In another embodiment, ralinepag is coadministered with treprostinil. In yet another embodiment, ralinepag is coadministered with iloprost. In still yet another embodiment, ralinepag is coadministered with prostacyclin. In another embodiment, ralinepag is coadministered with riociguat and treprostinil. In another embodiment, ralinepag is coadministered with riociguat and iloprost.

Ralinepag is a highly selective IP receptor agonist. In normal human pulmonary arterial smooth muscle cells (PASMCs), the IP receptor, through the generation of cyclic AMP appears to be the main mediator of the antiproliferative responses to treprostinil and iloprost (Wharton et al., 2000; Clapp et al., 2002; Falcetti et al., 2010). In contrast, in human PASMCs isolated from idiopathic pulmonary arterial hypertension (IPAH) patients, neither the IP receptor nor cyclic AMP appeared to be the main mediator underlying the antiproliferative effects of treprostinil and iloprost, at least at the concentrations studied (Falcetti et al., 2010).

The functional effects of ralinepag in pulmonary arteries or cells from microvessels of normal tissue or from PAH patients was previously unknown, and thus the pharmacological behavior of such selective IP agonists in the pulmonary circulation was unpredictable. Ralinepag was therefore evaluated with other prostacyclin drugs (which are expected to have diverse effects through activation of additional targets, including other prostanoid receptors (Clapp & Gurung, 2015)) to ascertain how it compares in its ability to generate cAMP and inhibit smooth muscle proliferation in PASMCs isolated from PAH patients.

EXAMPLES

The effects of combinations of ralinepag with endothelin-1 receptor antagonists (ERA), phosphodiesterase type 5 (PDE 5) inhibitors, or cAMP/cGMP elevating agents (e.g., soluble guanylate cyclase activators) was evaluated herein.
Source of Lung Tissue from Hypertensive and Normal Patients Lung tissue samples were obtained from patients with group 1 PAH or group 3 PAH (PAH associated with lung diseases) who were either undergoing transplantation after failed treatment, or who had died. For control samples, donor lungs found to be unsuitable for transplantation or from lung resection for suspected malignancy were used (Benyahia et al., 2013).

Primary cell lines of distal PASMCs from PAH patients were derived from explanted lungs as previously described (Falcetti et al., 2010; Bubb et al., 2014). These cells have an abnormal proliferative capacity when grown in culture (Zhang et al., 2007; Falcetti et al., 2010). Frozen cells were revived and grown in human smooth muscle basal medium-2 (SMBM; Lonza, Slough, UK) supplemented with 9% fetal bovine serum (FBS) at 37° C. in a humidified atmosphere of 5% CO2. After reaching confluence, cells were washed with phosphate-buffered saline (PBS) and treated with trypsin-EDTA for further passage. Only cells between passages 3 and 10 were used for experiments.
Cyclic AMP Assays Human PASMCs from PAH patients were grown to 70-80% confluence in 12 well plates in DMEM/F12 containing 9% foetal bovine serum (FBS), penicillin (50 U/ml)/streptomycin (50 ag/ml). To assess the time-course of cAMP elevation, cells were stimulated with 100 nM ralinepag for varying times (0.5, 1, 2, 4, 8, 24, 48 hours). This dose of ralinepag was chosen on the basis that it was close to the $EC_{50}$ for cAMP generation in preliminary experiments. In other experiments, the IP receptor agonist was added for a specified time (60 minutes) over a full concentration range (0.1-10,000 nM) in the absence and presence of 1 M of the IP receptor antagonist, RO-1138452. The antagonist is added 30 minutes beforehand and remained throughout.

To extract cyclic AMP, the medium was aspirated and PASMCs cells incubated in 0.1 M HCl for 20 minutes on ice followed by centrifugation at 1000 g for 10 minutes at 4° C.

The protein concentration in the supernatant was determined using a Bradford based protein assay (BCA, Novagen, EmD Chemicals, CA, USA). Intracellular cyclic AMP was measured using a competitive enzyme immunoassay 96 well plate kit (ADI-900-163, Enzo Life Sciences, Exeter, UK) and the assay performed according to the manufacturer's instructions. Each sample was run in duplicate and data expressed as pmol of cAMP per mg of total protein for each individual sample. Basal levels were subtracted from each agonist concentration data point. Given the large variation (~15-fold) in cAMP generation from different patient samples, data was also normalized to the peak cyclic AMP response (assigned 100%) in each cell isolate.

Cell Proliferation Assays

Comparative concentration-dependent effects of IP receptor agonists on cell proliferation were assessed on human PASMCs derived from PAH patients. Cells were seeded onto 96-well plates at a density of $1\times10^4$ cells/ml and grown at 37° C. in a humidified $CO_2$ incubator in human smooth muscle basal medium-2 (SMBM; Lonza) containing 9% FBS and penicillin-streptomycin (Pen/Strep; 50 units/ml). After 24 hours, cells were growth arrested by incubating for 48 hours in fresh media containing no added serum. Media was then subsequently removed, replaced with human SMBM containing 9% serum with or without 0.1% DMSO in the absence and presence of the IP receptor agonist (either ralinepag, iloprost, treprostinil or MRE-269) and cells treated with the IP receptor agonist for 4 days over the concentration range (10-12-10-5 M). Responses were directly compared in cells containing the IP receptor antagonist, RO-1138452 (1 µM), which was added to cells 30-60 minutes prior to the addition of the IP agonist and remained throughout the experiment. Cells incubated with no added serum over the same time period (4 days) acted as the time control.

Cell proliferation was obtained using an MTS proliferation kit (Promega), a colorimetric method for determining the number of viable cells which is based on the cleavage of the tetrazolium salt MTS to formazan by cellular mitochondrial dehydrogenases. An increase in cell number leads to a proportional increase in the amount of formazan dye formed which is quantified by measuring the absorbance of the dye solution at 490 nm. In each case background absorbance was corrected by subtracting the average absorbance from the "no cell" control wells from all other absorbance values.

Cell proliferation was then normalized to the growth response induced by FBS alone, which was taken as the FBS response minus the time control (=100% growth at 4 days). Growth responses induced in presence of solvent±drugs is shown as % change in cell proliferation relative to the FBS response alone in all figures.

Materials, Reagents, Equipment
  Human Smooth Muscle Basal Medium-2 (Lonza, Slough, UK; Cat No. CC-3181)
  DMEM/F12 (Life Technologies, Paisley, UK; Cat No 11320-074)
  Foetal bovine serum South American (FBS; Invitrogen, Cat No 10270106)
  Penicillin-Streptomycin Pen/Strep (5000 units/ml; Life Technologies, Paisley, UK; Cat No 15070-063)
  Sterile Ca2+/Mg2+ free phosphate buffered saline (PBS; Life Technologies, Cat No 10010-056)
  Sterile Trypsin/EDTA solution (0.05%; Life Technologies, Cat No 25300-054)
  Sterile dimethyl sulfoxide (DMSO; Sigma-Aldrich, Cat No, D2650)
  MRE-269 ([4[(5,6diphenylpyrazinyl)(1methylethyl) amino]butoxy]acetic acid (CAY10010412), iloprost (50:50 R/S isomer; CAY 18215), treprostinil (CAY10162) and RO-1138452 (IP receptor antagonist; CAY 10441), riociguat (Cat No 2644-5), sildenafil citrate (Cat No 2872-10), macitentan (Cat No M009) and treprostinil (CAY10162) were purchased from Cambridge Bioscience, UK (distributor for Cayman Chemical Co). Bosentan (Cat No 11731) was purchased from Cayman Chemicals Company (USA).
  Iloprost came dissolved in methyl acetate which was blown off and replaced with DMSO to give a stock solution of 10 mM. All other stock solutions were made up in DMSO (treprostinil, RO-1138452, ralinepag, MRE-269) to a final concentration of 10 mM. Drugs were serially diluted in growth medium, with the solvent concentration in each well remaining constant at 0.11% regardless of the concentration of the agent added.
  Competitive enzyme immunoassay 96 well plate cAMP kit (ADI-900-163, Enzo Life Sciences, Exeter, UK)
  Cell proliferation assay kit (MTS, Promega, UK, Cat No G5421)
  BCA (bicinchoninic acid) protein assay kit (Cat No. 71285-3; Novagen, Merck Millipore, Nottingham, UK)
  Galaxy R CO2 cell culture incubator (WolfLabs Ltd, York UK)
  Tecan Genios Microplate Reader (Tecan Group Ltd, Mannedorf, Germany)
  OpsysMRTM Microplate Reader (Dynex Technology, Chantilly, Va., USA)

Data and Statistical Analysis

All data are presented as mean±standard error of mean (S.E.M) of at least 5 observations. Agonist log-concentration curves were constructed and fitted using the non-linear fitting routine in GraphPad Prism 4 or 6 (San Diego, Calif., USA). The concentration of agonist causing 50% of the maximal response ($E_{max}$) was expressed as the negative log ($pEC_{50}$) and the mean $EC_{50}$ calculated. Statistical analysis was performed using one or two way ANOVA with post-hoc correction as indicated in the figure legends. P values <0.05 are considered statistically significant.

Example 1: Antiproliferative Effects of Ralinepag in Combination with Cyclic GMP and Cyclic AMP Elevating Agents or Endothelin-1 Antagonists The antiproliferative effects of ralinepag in human pulmonary smooth muscle cells (PASMCs) from PAH patients were compared with other prostacyclin mimetics, and compared in combination with an endothelin-1 receptor antagonist (ERA), a phosphodiesterase type 5 (PDE5) inhibitor or a soluble guanylate cyclase (sGC) activator.

Ralinepag and MRE-269 behaved as selective IP receptor agonists in cyclic AMP and cell proliferation assays in human PASMCs from PAH patients, with ralinepag producing 2-fold more cyclic AMP and 10-fold more antiproliferation effects. Both ralinepag and MRE-269 produced weaker maximal effects in the cyclic AMP and cell proliferation assays than treprostinil. Treprostinil and iloprost exhibited inhibition of cell proliferation through IP-independent mechanisms.

Antiproliferative Effects of Ralinepag in Combination with Riociguat

The concentration-dependent antiproliferative effects of ralinepag in the absence and presence of 100 nM riociguat in human PASMCs grown in 9% serum and 0.1% DMSO for four days are shown in FIG. 1. In four out of the five cell isolates, there was a greater inhibition of cell growth when riociguat was combined with ralinepag compared to ralinepag alone. From the mean data, overall, ralinepag was more effective in the presence of riociguat across the entire concentration range (0.01-10,000 nM), being significantly more effective at 10 nM and above (P<0.05, two way ANOVA, with Bonferroni post-hoc correction).

Figure 2:
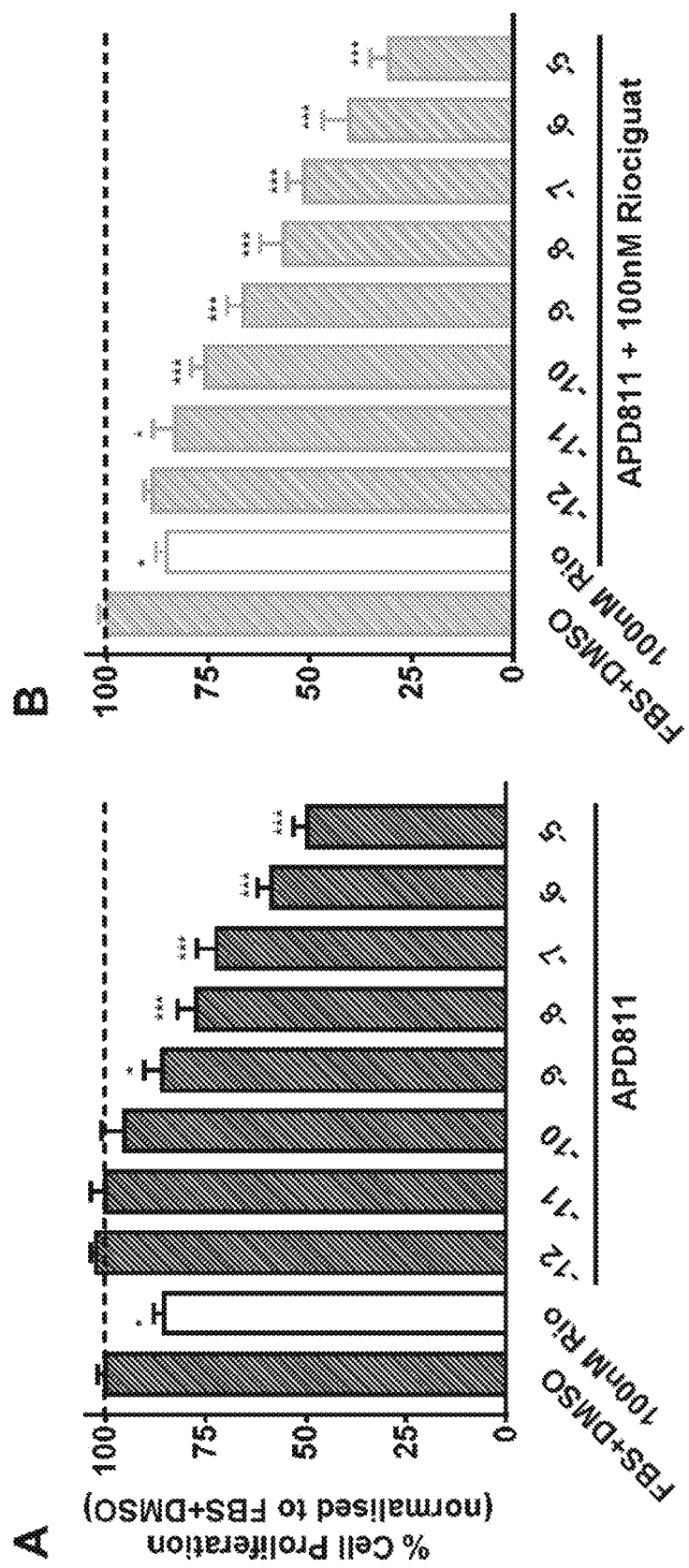
FIG. 2 shows that ralinepag is a more effective inhibitor of serum-induced proliferation in human PASMCs from PAH patients in the presence of riociguat. Mean antiproliferative effects of increasing doses of ralinepag in the absence (A) and presence of 100 nM riociguat (B). Human PASMCs were grown in 9% serum (FBS) and 0.1% DMSO for 4 days±drug(s). Cell proliferation was normalized to the growth response induced by FBS and DMSO, which was taken as the FBS response minus the time control (=100% growth at 4 days). Growth responses induced in the presence of ralinepag and solvent±riociguat are shown as % change in cell proliferation relative to the FBS response alone. Shown on the graph also is the effect riociguat (100 nM) in the presence of growth medium containing solvent *=P<0.05, ***=P<0.001 when compared to control (FBS and DMSO); 1 WAY-ANOVA with Bonferroni post hoc test (n=5).
Figure 3A:
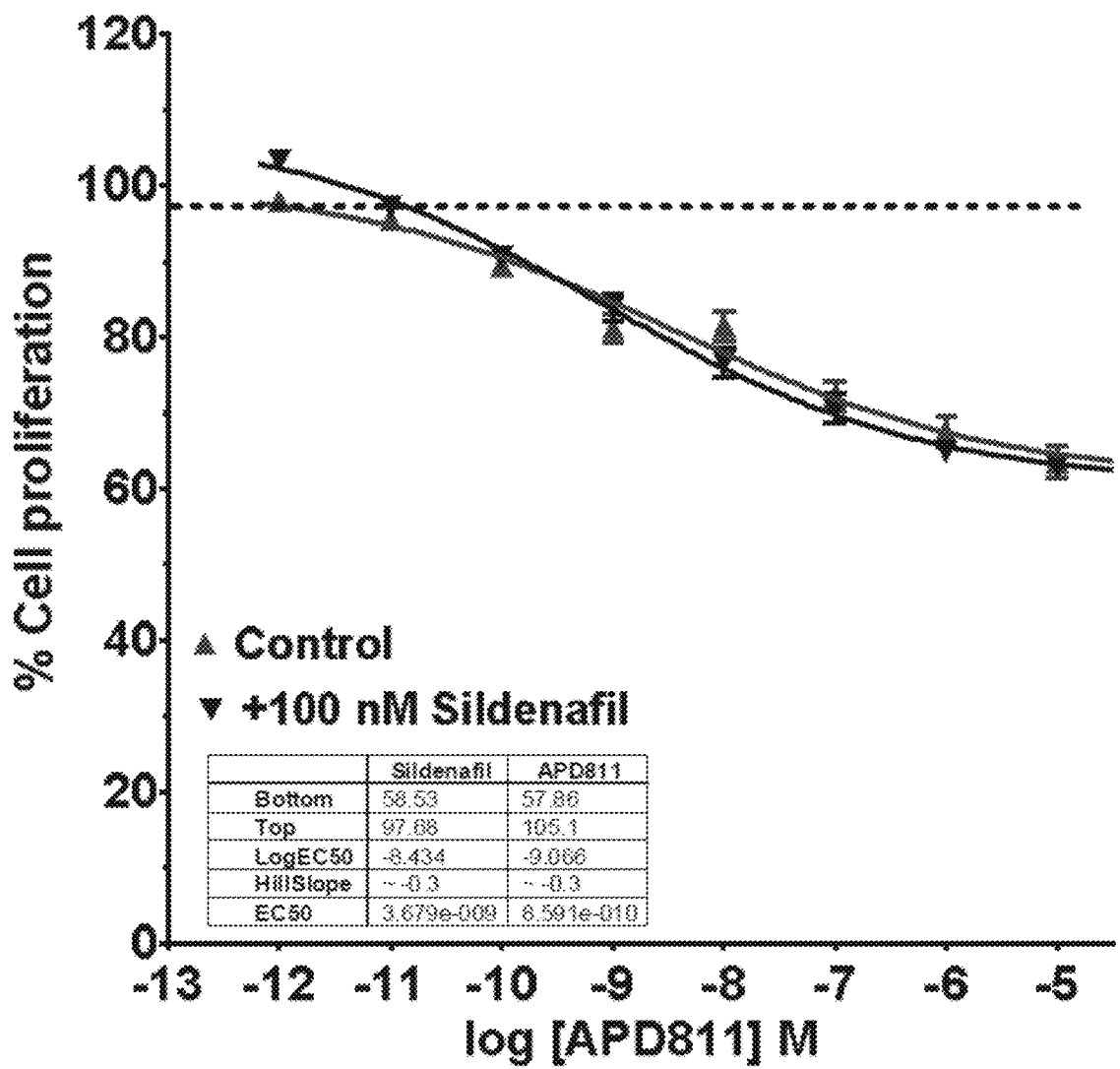
FIGS. 3A-3F show antiproliferative effects of ralinepag in combination with 100 nM sildenafil. Growth arrested cells were incubated for 96 hours in human smooth muscle basal medium (SMBM) containing either 9% FBS+0.1% DMSO, FBS plus ralinepag and DMSO in the absence and presence of 100 nM sildenafil or SMBM alone (time control). Cell proliferation was normalized to the growth response induced by FBS alone, which was taken as the FBS response minus the time control (=100% growth at 4 days). Growth responses induced in the presence of ralinepag plus solvent are shown as % change in cell proliferation relative to the FBS response alone. Data were fit using a variable slope sigmoidal-curve fitting routine in GraphPad and parameters of each fit are shown. Data are from 5 individual patient cell isolates.
Figure 3B:
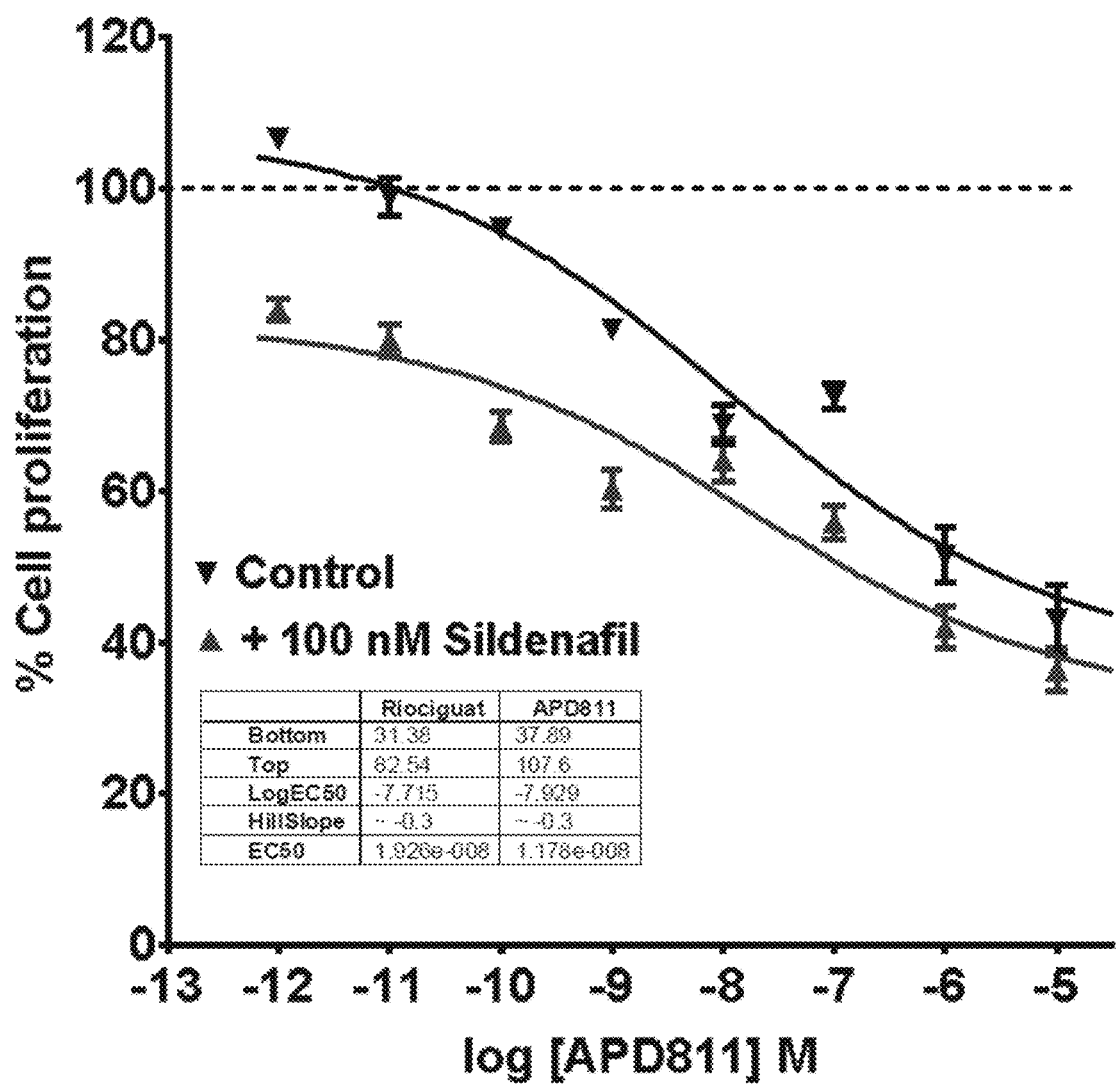
Figure 3C:
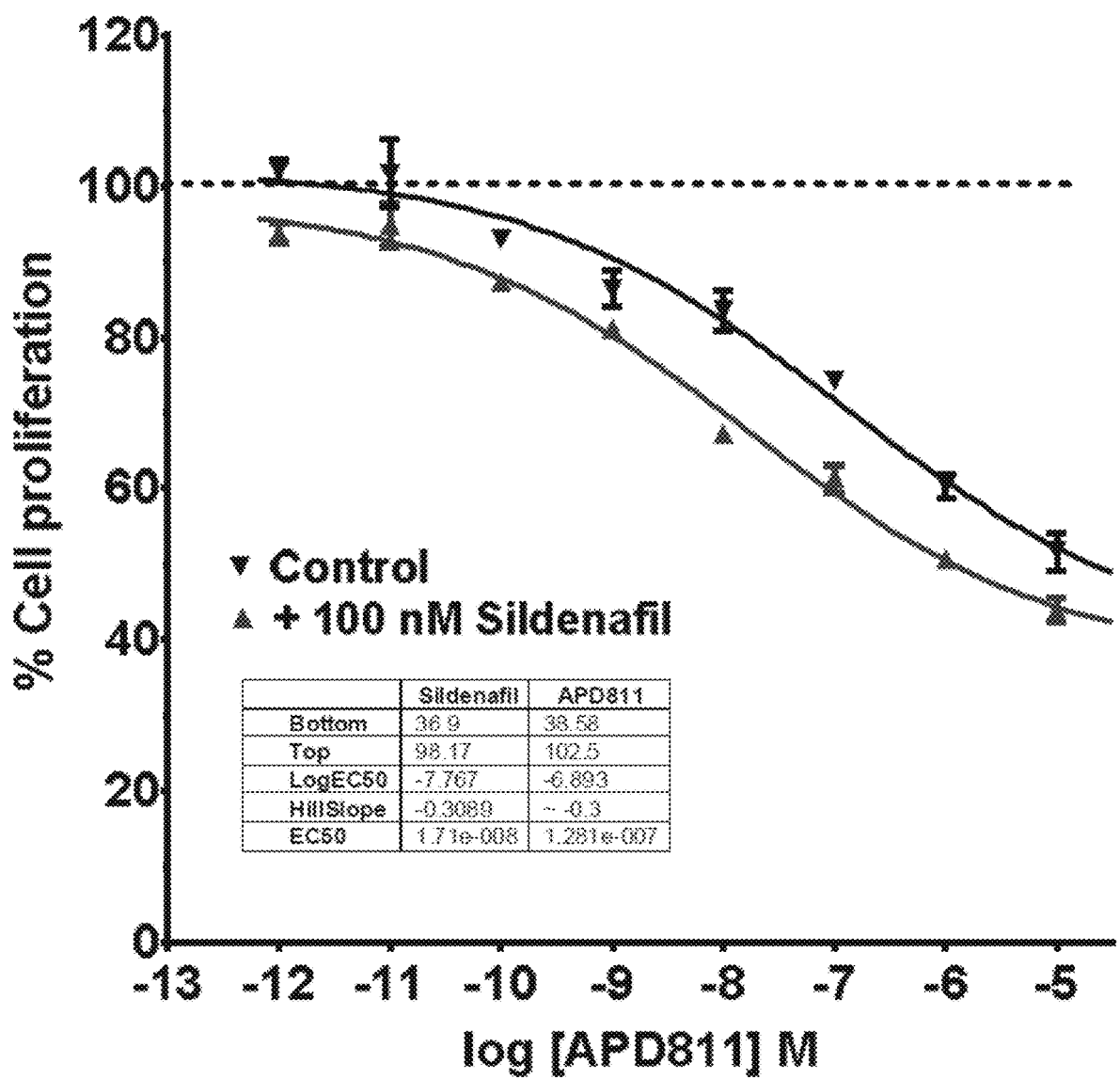
Figure 3D:
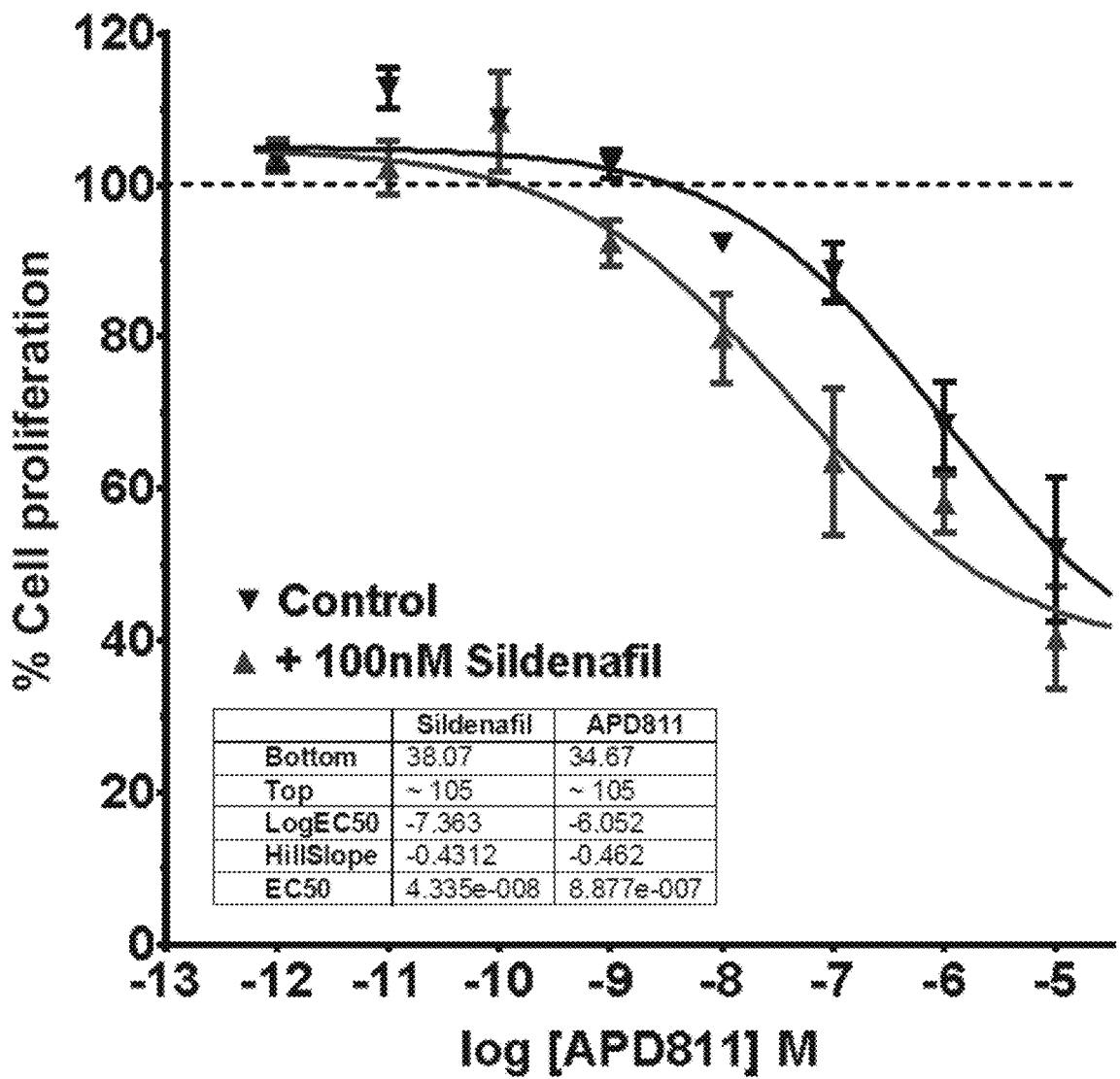
Figure 3E:
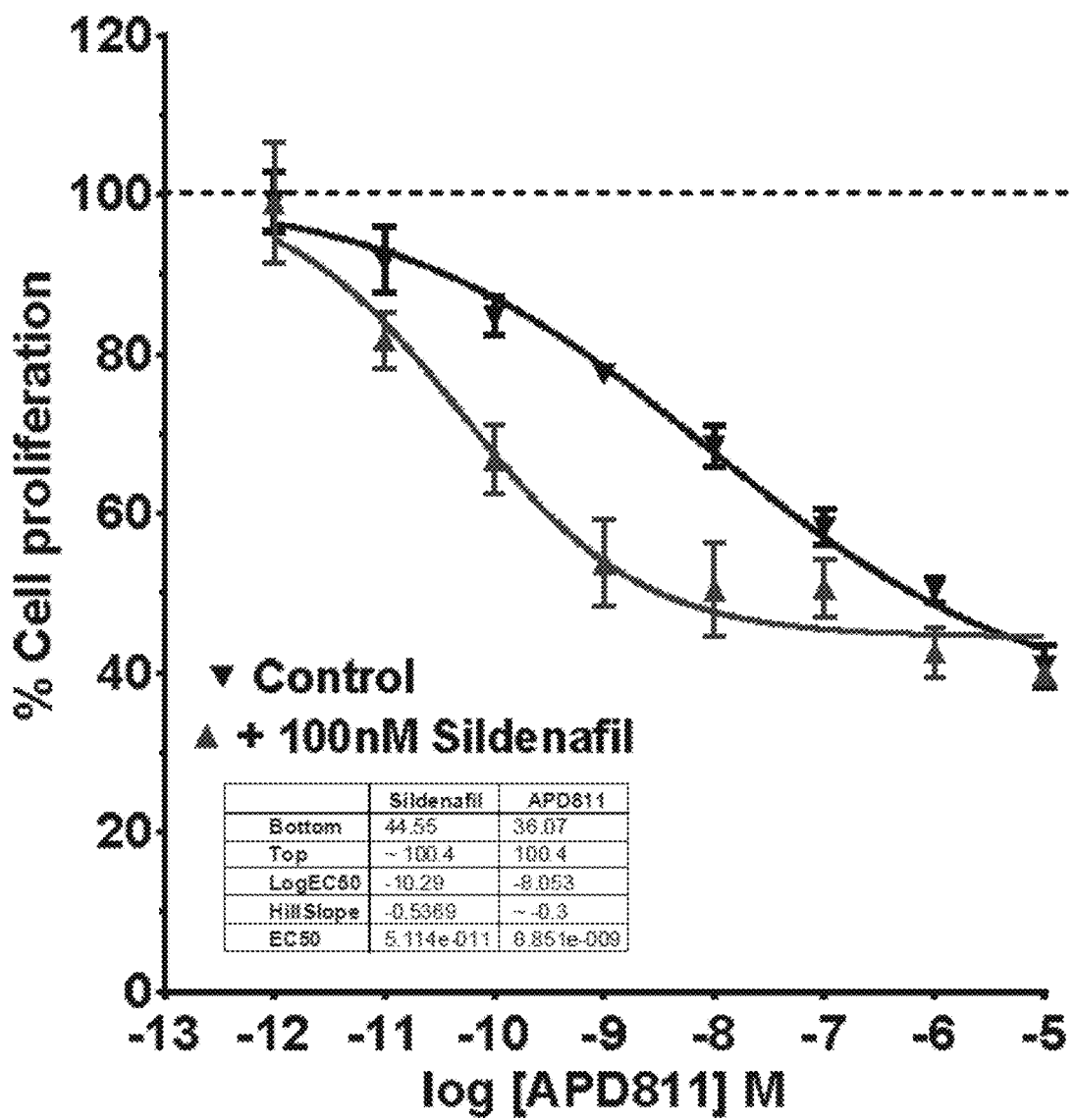
Figure 3F:
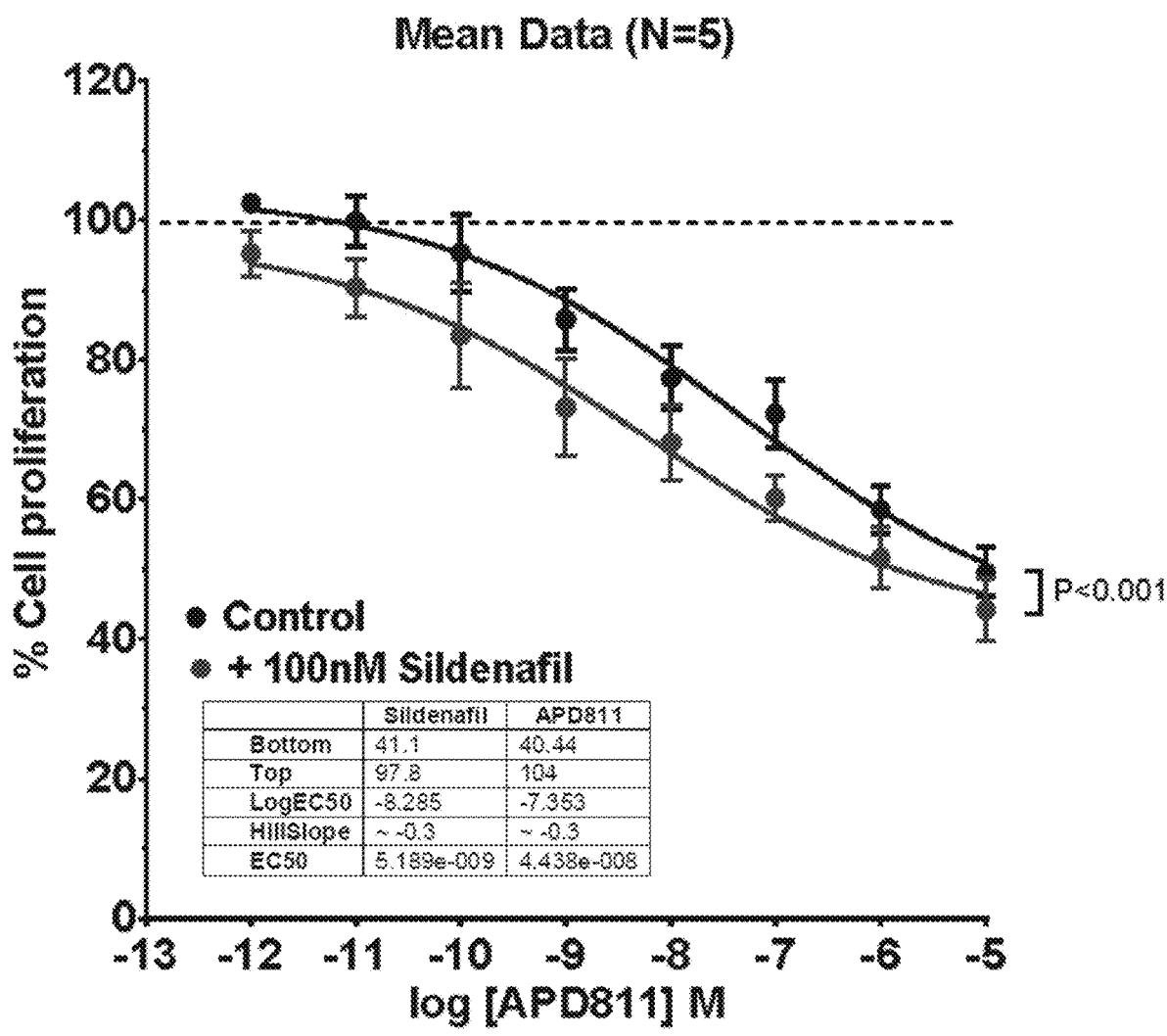

Riociguat alone (100 nM) caused significant inhibition (~15%) of cell proliferation compared to FBS and DMSO. At 100 nM, ralinepag inhibited growth by 28% (FIG. 2A), which was almost double the inhibition induced by the same dose of riociguat (FIG. 2B). However, in the presence of 100 nM riociguat, significant inhibition of cell growth occurred at a 100-fold lower dose (0.01 nM) of ralinepag. This suggests that the agents work on separate pathways to enhance inhibition of proliferation-riociguat through cGMP (Lang et al., 2012) and ralinepag through the IP receptor and cAMP generation (proliferation was completely inhibited by the IP receptor antagonist RO1138452 in experiments provided herein). Potentiation occurred at sub nanomolar concentrations of ralinepag. At the higher doses of ralinepag, inhibition of cell growth appeared to be more than predicted from additive effects.

Riociguat has been shown to induce apoptosis and inhibit proliferation of pulmonary artery cells associated with an up-regulation of soluble guanylyl expression and increased cyclic GMP production (Lang et al., 2012). Thus, potentiation of ralinepag effects by riociguat may result from elevated cyclic AMP levels in response to cyclic GMP-dependent inhibition of PDE3, an isoform known to regulate cAMP generation induced by IP receptor agonists (Knebel et al., 2013). Previous experiments showed that riociguat was the most effective antiproliferative combination with treprostinil compared to either PDE5 inhibitors or ERAs in human PASMCs from PAH patients (Patel et al., 2014). However, the combined effects were less than predicted if additive. Both agents may work on separate pathways (cyclic GMP and the IP receptor/cAMP pathway) with some crossover in terms of mechanism of growth inhibition. For example, inhibition of cell growth through inhibition of the calcium-dependent phosphatase, calcineurin, could occur through both cyclic GMP and cyclic AMP (Jabr et al., 2007; Lu et al., 2013).

Antiproliferative Effects of Ralinepag in Combination with Sildenafil

Figure 4:
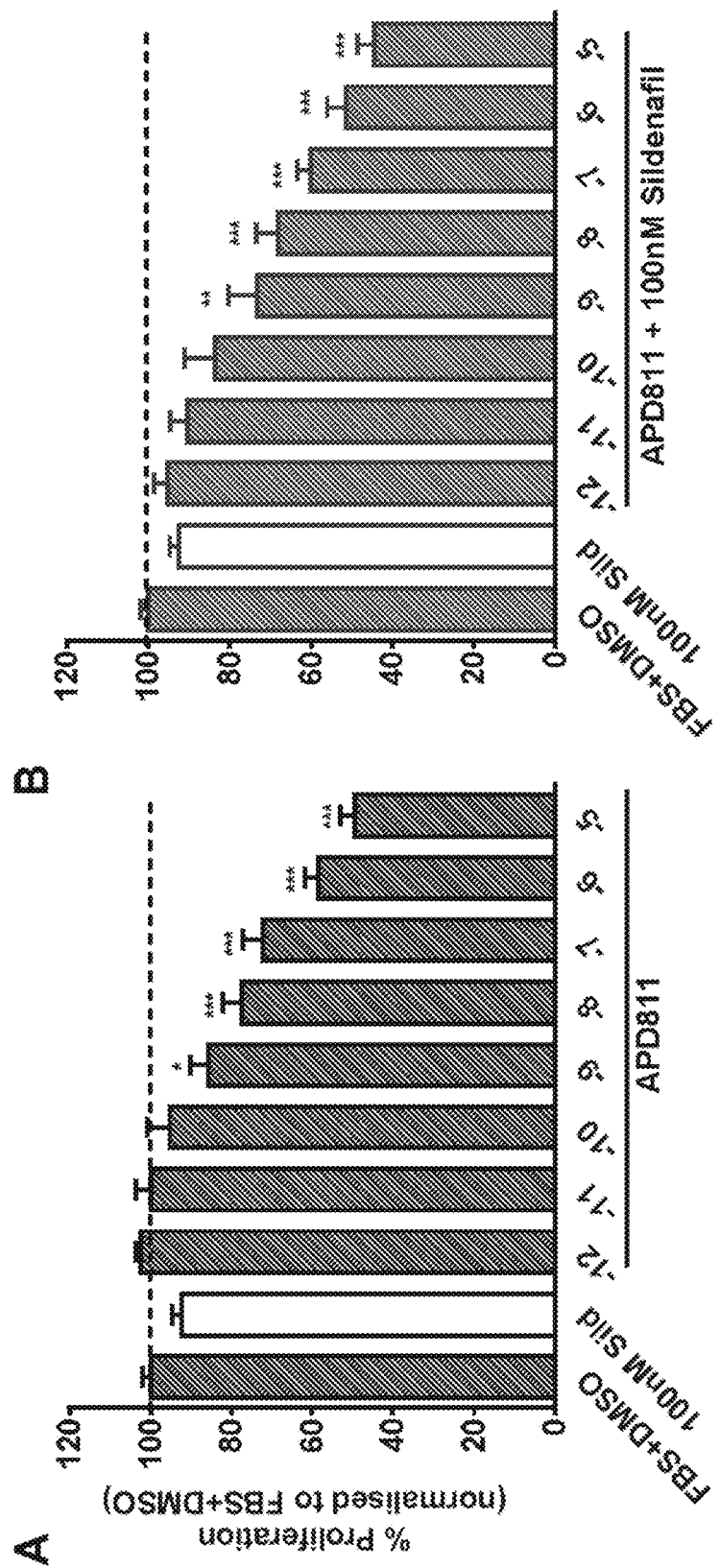
FIG. 4 shows the effect of sildenafil on the antiproliferative response of ralinepag in human PASMCs from PAH patients. Mean anti-proliferative effects of increasing doses of ralinepag in the absence (A) and presence of 100 nM sildenafil (B). Human PASMCs were grown in 9% serum (FBS) and 0.1% DMSO for 4 days±drug(s). Cell proliferation was normalized to the growth response induced by FBS alone, which was taken as the FBS response minus the time control (=100% growth at 4 days). Growth responses induced in the presence of ralinepag and solvent±sildenafil are shown as % change in cell proliferation relative to the FBS response alone. Shown on the graph is the effect sildenafil (Sild; 100 nM) in the presence of growth medium containing solvent. *=P<0.05, =P<0.01, *=P<0.001 when compared to control (FBS and DMSO); 1-WAY ANOVA with Bonferroni post hoc test (n=5).
Figure 5A:
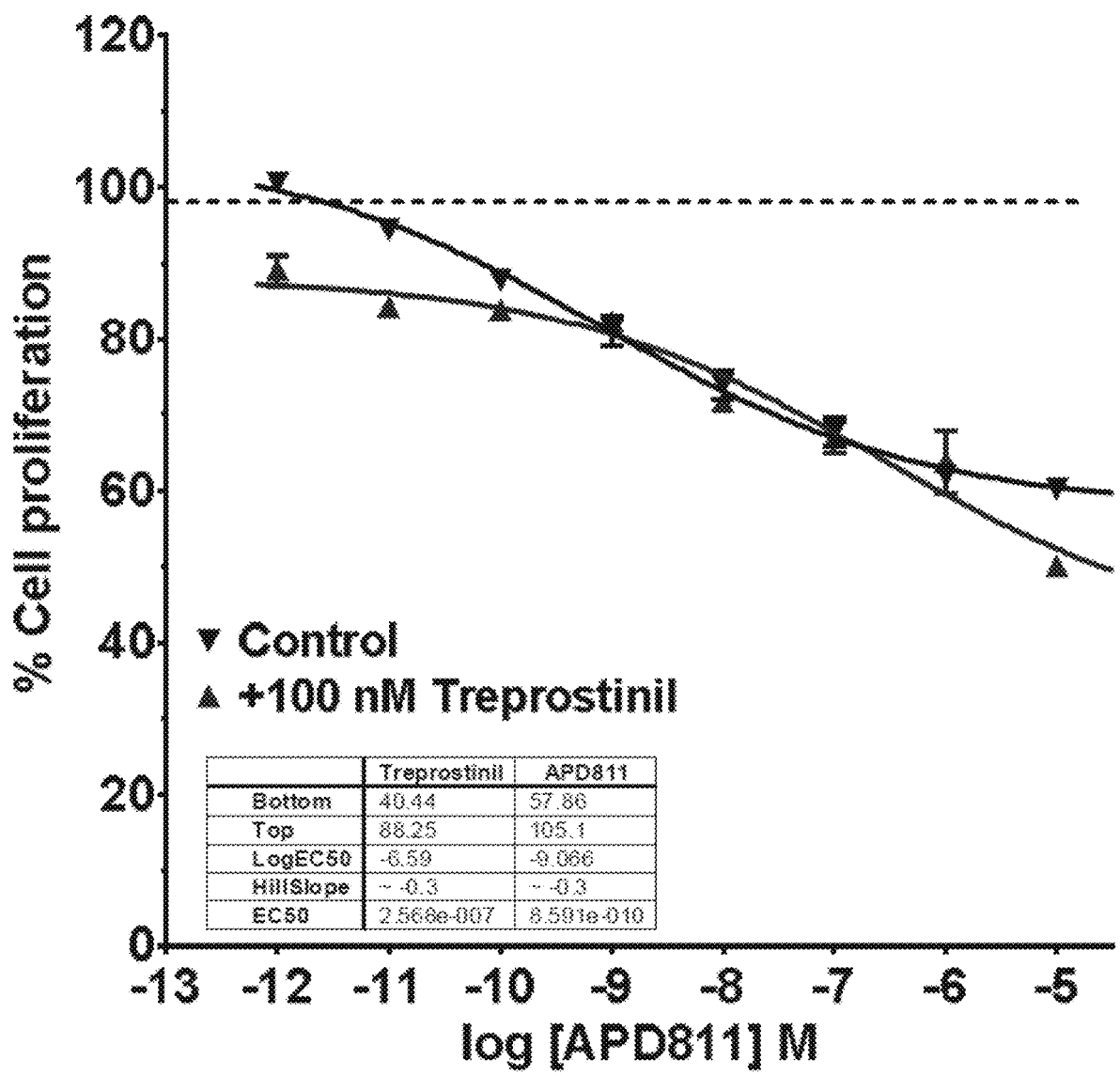
FIGS. 5A-5F show antiproliferative effects of ralinepag in combination with 100 nM treprostinil. Growth arrested cells were incubated for 96 hours in human smooth muscle basal medium (SMBM) containing either 9% FBS+0.1% DMSO, FBS plus ralinepag and DMSO in the absence and presence of 100 nM treprostinil or SMBM alone (time control). Cell proliferation was normalized to the growth response induced by FBS alone, which was taken as the FBS response minus the time control (=100% growth at 4 days). Growth responses induced in the presence of ralinepag plus solvent are shown as % change in cell proliferation relative to the FBS response alone. Data were fit using a variable slope sigmoidal-curve fitting routine in GraphPad and parameters of each fit are shown. Data are from 5 individual patient cell isolates.
Figure 5B:
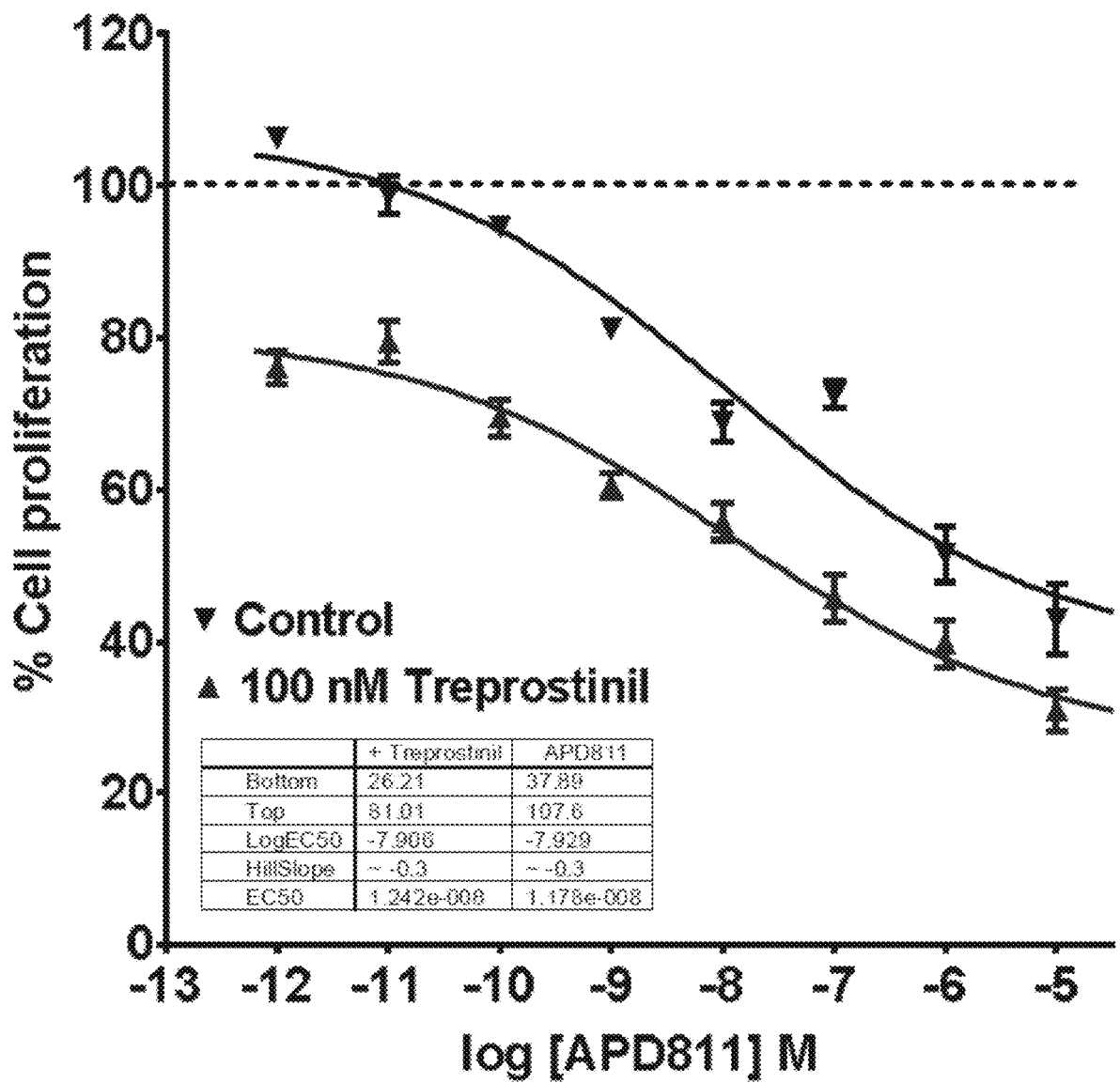
Figure 5C:
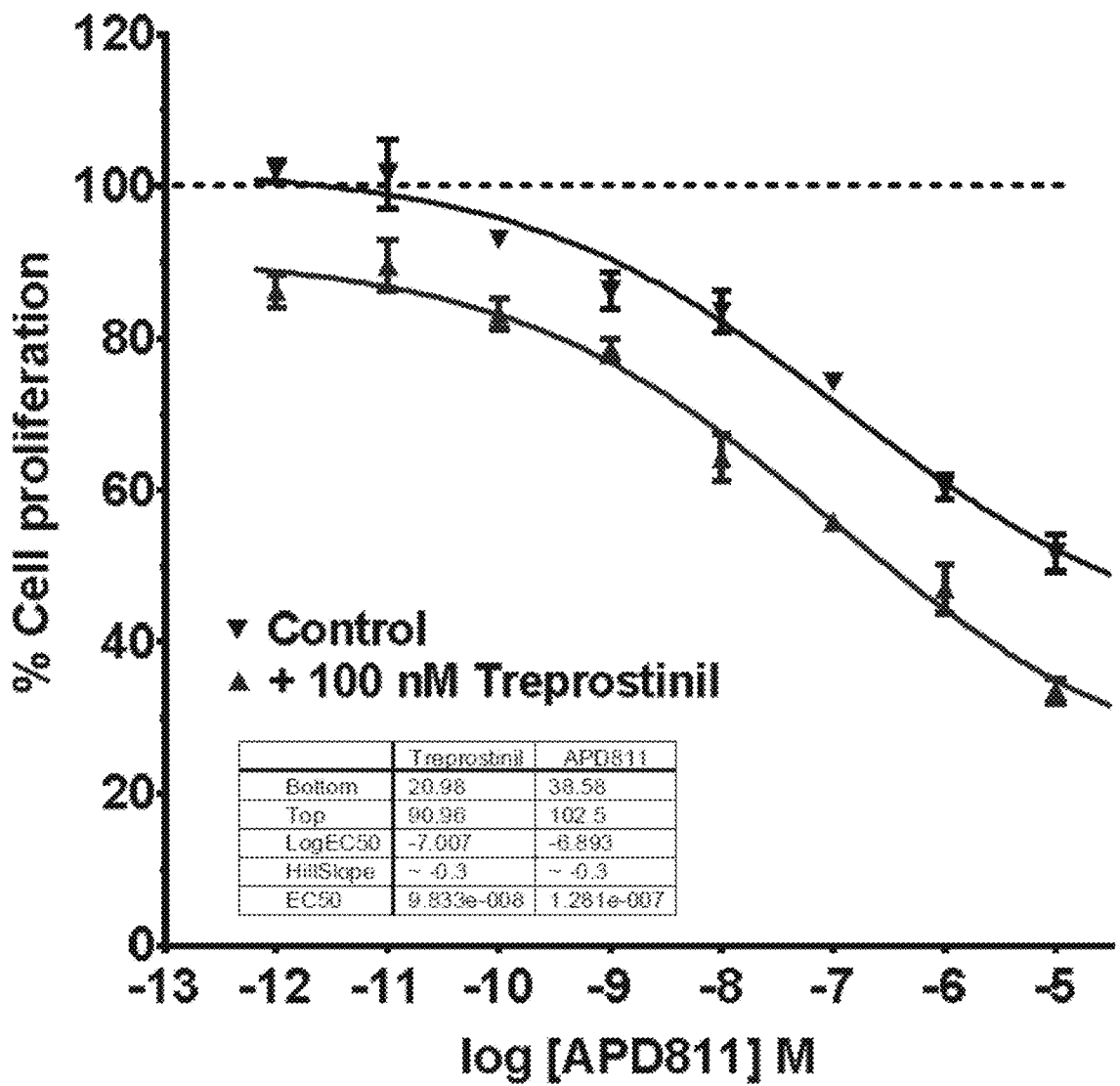
Figure 5D:
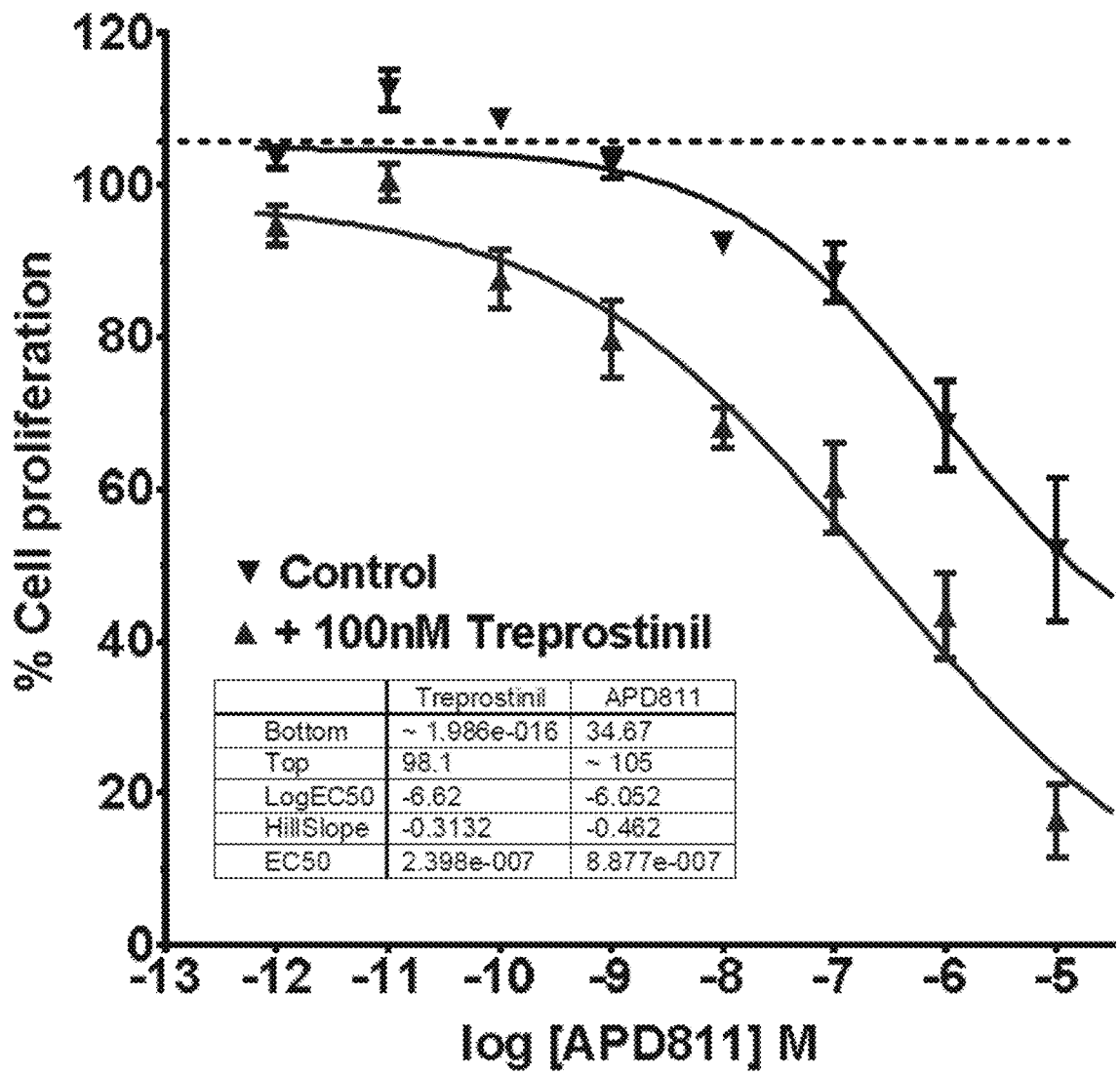
Figure 5E:
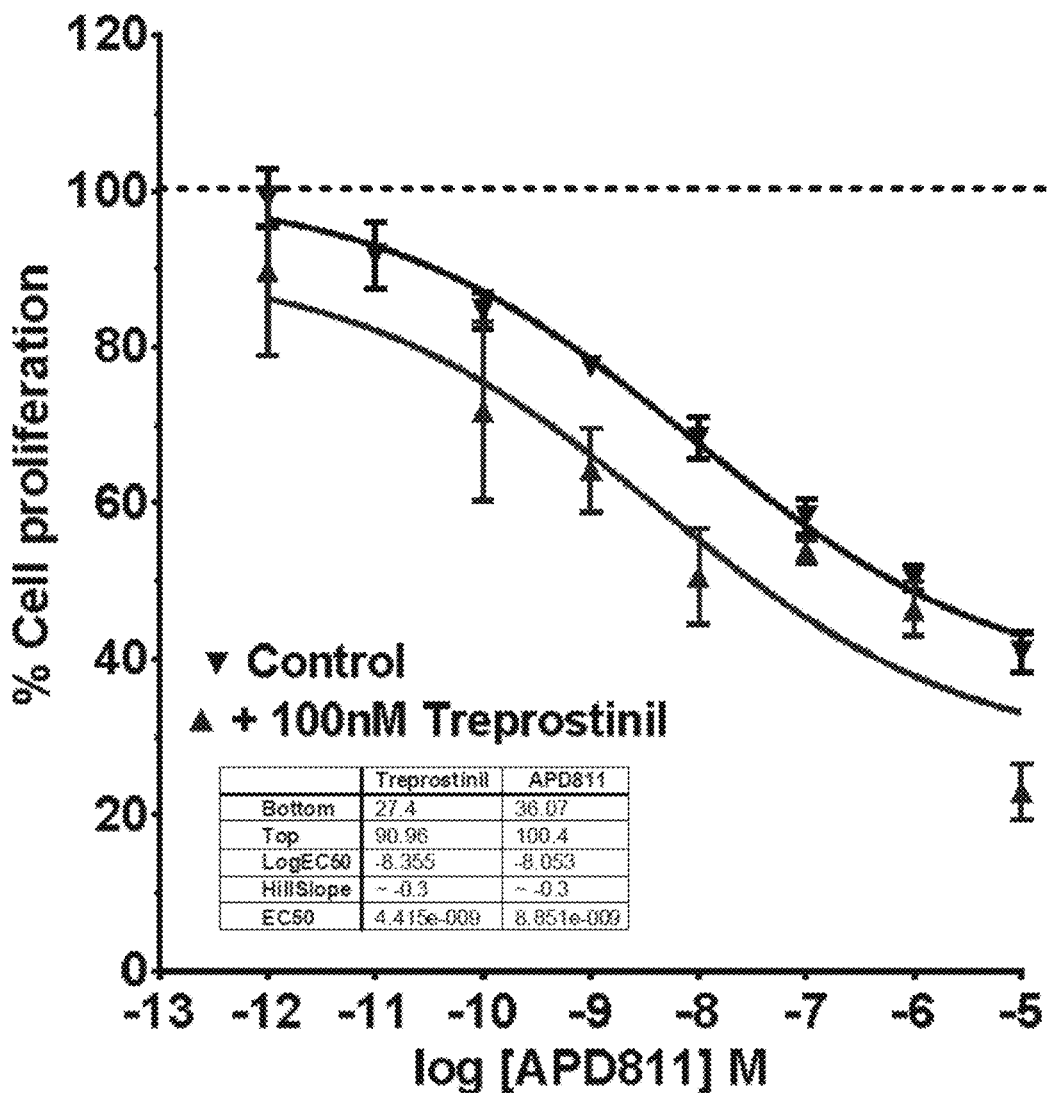
Figure 5F:
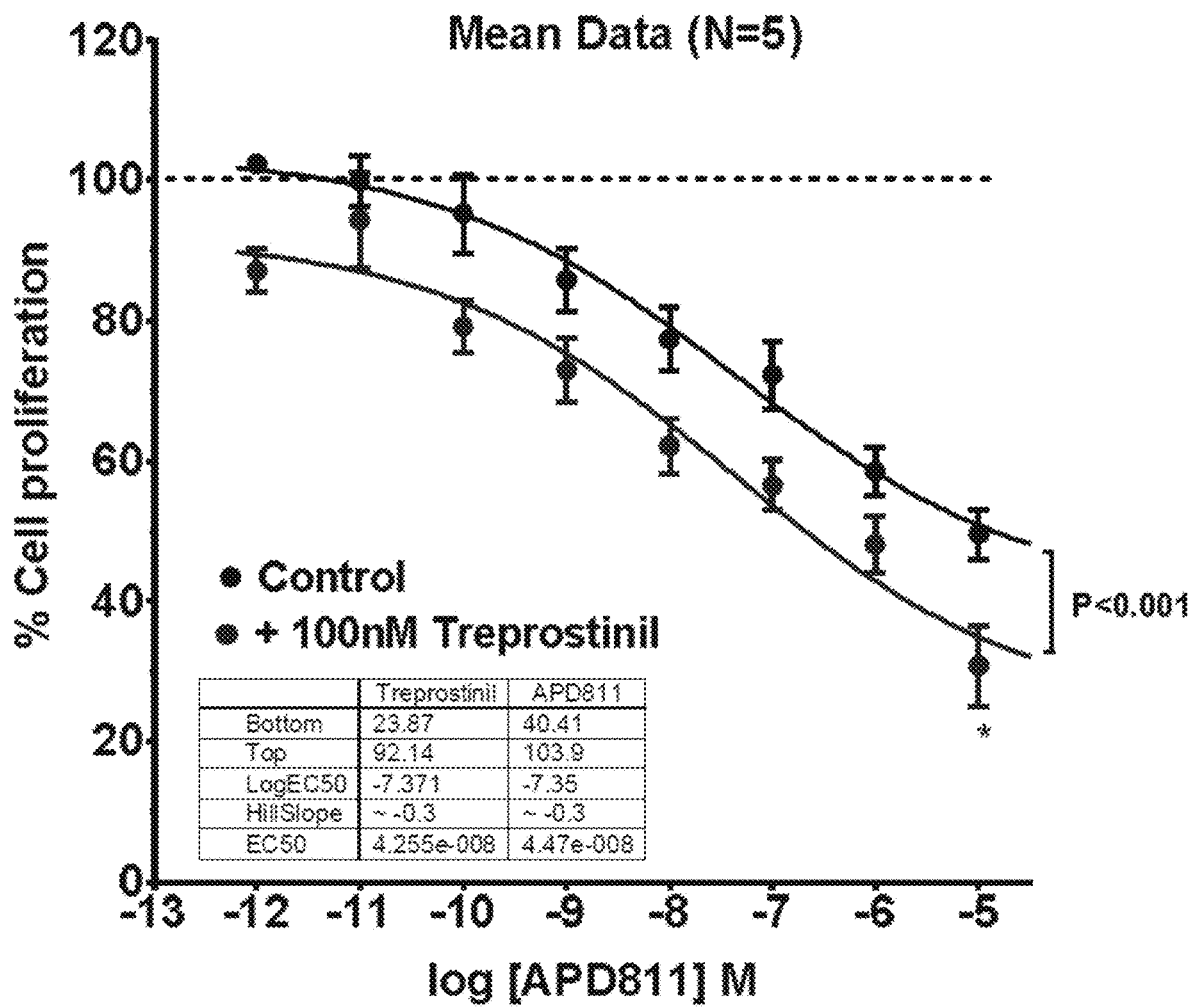

The concentration-dependent antiproliferative effects of ralinepag in the absence and presence of 100 nM sildenafil in human PASMCs grown in 9% serum and 0.1% DMSO for four days are shown in FIG. 3. In four out of the five cell isolates, there was a greater inhibition of cell growth when sildenafil was combined with ralinepag compared to ralinepag alone. Ralinepag appeared significantly (P<0.001, two-way ANOVA) more effective in the presence of sildenafil across the entire concentration range (0.01-10,000 nM), though significance at individual drug doses was not found with a Bonferroni post-hoc analysis. The mean antiproliferative effects of ralinepag in the absence and presence of 100 nM sildenafil compared with responses to 9% serum and 0.1% DMSO alone are shown in FIG. 4. Unlike riociguat, sildenafil (100 nM) did not significantly inhibit growth induced by serum. However, when combined with ralinepag, there was further inhibition of cell growth compared to ralinepag alone. At 1 nM ralinepag, growth was inhibited by 14% rising to 27% in the presence of sildenafil, though the magnitude of these changes were smaller at the highest (10 µM) dose tested (56% inhibition of cell growth as opposed to 50%).

The potentiating effect of sildenafil was found to be less than was observed with riociguat. This may due to riociguat being a direct activator of guanylate cyclase, producing a greater rise in cyclic GMP than sildenafil, which would be expected to increase basal cyclic GMP levels. Furthermore, in three of five cell isolates, the antiproliferative effects of the drug combination tapered off at higher doses of ralinepag, consistent with some overlap of downstream mechanisms of PDE5 inhibitors and IP receptor agonists. Indeed, sildenafil inhibits cell proliferation in part through activation of PPARy (Wang et al., 2013), a mechanism known to underlie the antiproliferative effects of treprostinil in these pulmonary smooth muscle cells (Falcetti et al., 2010). It is likely for sildenafil that the dose used in these experiments is below the therapeutic dose, as the upper plasma levels of this drug in patients was 1500 nM (Burgess et al., 2008). It is, however, well above the $K_i$ for PDE5 inhibition reported for sildenafil, which is reported to be 1-3 nM (Ballard et al., 1998). At 100 nM, sildenafil is also likely to inhibit PDE1 and PDE6 activity ($K_i$ 40 nM and 10 nM, respectively), so its mode of action therapeutically may not entirely be related to inhibition of PDE5 (Bischoff, 2004).

Antiproliferative Effects of Ralinepag in Combination with Treprostinil

The antiproliferative effects of ralinepag in the absence and presence of 100 nM treprostinil in human PASMCs grown in 9% serum and 0.1% DMSO for 4 days is shown in FIG. 5. In four out of the five cell isolates, there was a greater inhibition of cell growth when treprostinil was combined with ralinepag compared to ralinepag alone. From the mean data, overall ralinepag appeared more effective in the presence of treprostinil across the entire concentration range (P<0.001, two-way ANOVA), though only the highest dose (10 µM) of ralinepag was significantly enhanced by treprostinil in a post hoc test (P<0.05, two-way ANOVA with Bonferroni correction).

Figure 6:
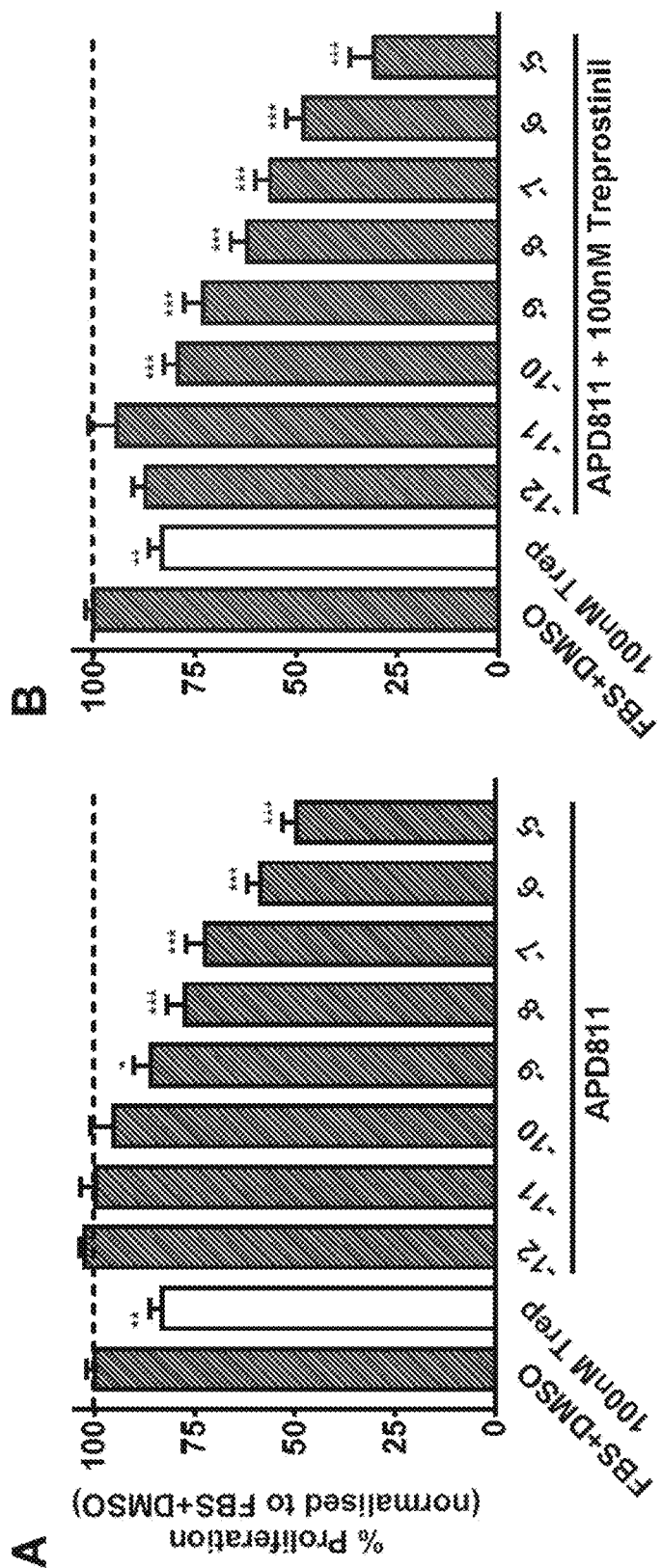
FIG. 6 shows ralinepag is a more effective inhibitor of serum-induced proliferation in human PASMCs from PAH patients in the presence of treprostinil. Mean antiproliferative effects of increasing doses of ralinepag in the absence (A) and presence of 100 nM treprostinil (B). Human PASMCs were grown in 9% serum (FBS) and 0.1% DMSO for 4 days±drug(s). Cell proliferation was normalized to the growth response induced by FBS alone, which was taken as the FBS response minus the time control (=100% growth at 4 days). Growth responses induced in the presence of ralinepag and solvent±treprostinil are shown as % change in cell proliferation relative to the FBS response alone. Shown on the graph also is the effect treprostinil (Trep; 100 nM) in the presence of growth medium containing solvent *=P<0.05, =P<0.01, *=P<0.001 when compared to control (FBS and DMSO); 1 WAY-ANOVA with Bonferroni post hoc test (n=5).
Figure 7A:
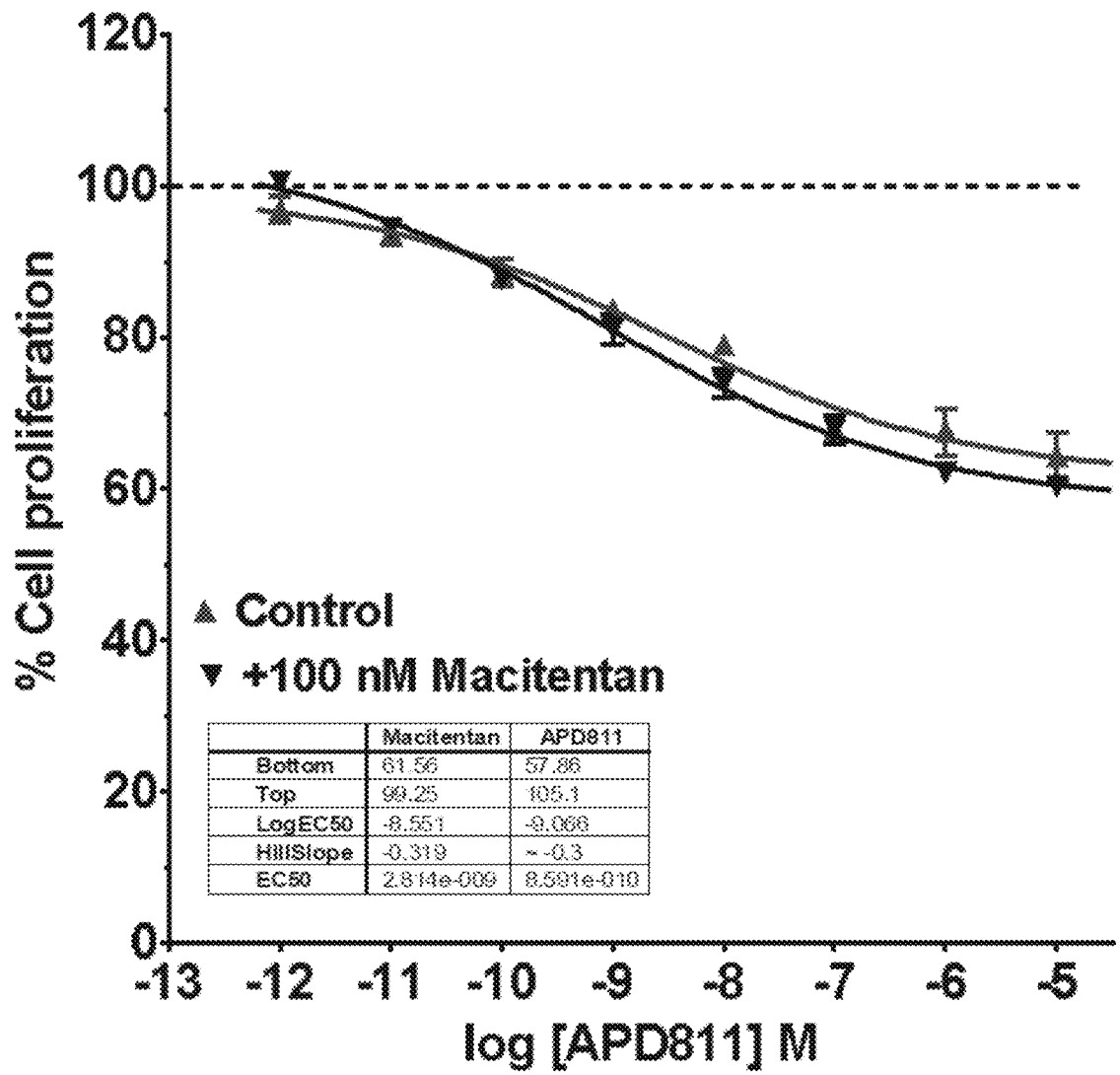
FIGS. 7A-7F show antiproliferative effects of ralinepag in combination with 100 nM macitentan. Growth arrested cells were incubated for 96 hours in human smooth muscle basal medium (SMBM) containing either 9% FBS+0.1% DMSO, FBS plus ralinepag and DMSO in the absence and presence of 100 nM macitentan or SMBM alone (time control). Cell proliferation was normalized to the growth response induced by FBS alone, which was taken as the FBS response minus the time control (=100% growth at 4 days). Growth responses induced in the presence of ralinepag plus solvent are shown as % change in cell proliferation relative to the FBS response alone. Data were fit using a variable slope sigmoidal-curve fitting routine in GraphPad and parameters of each fit are shown. Data are from 5 individual patient cell isolates.
Figure 7B:
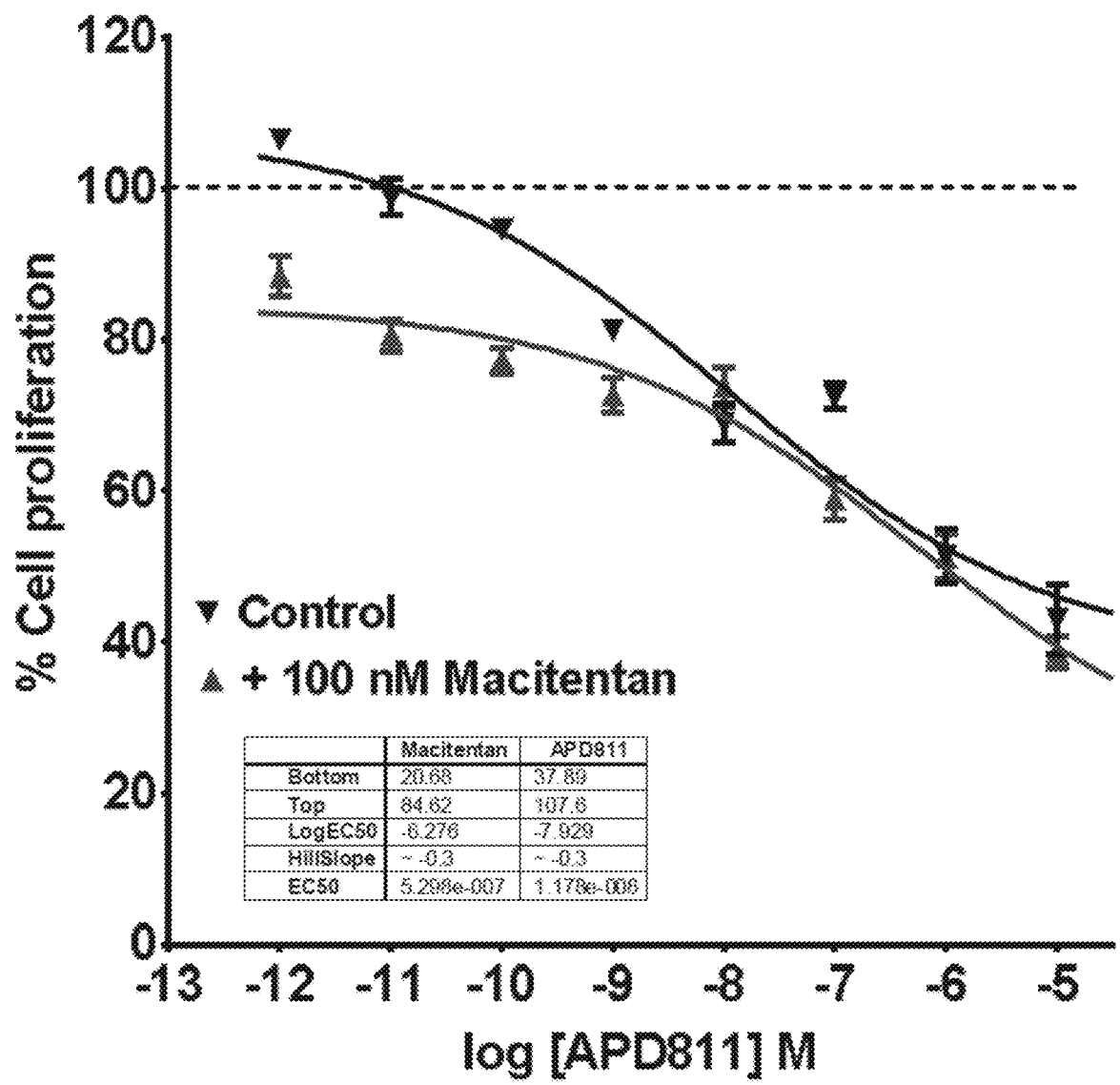
Figure 7C:
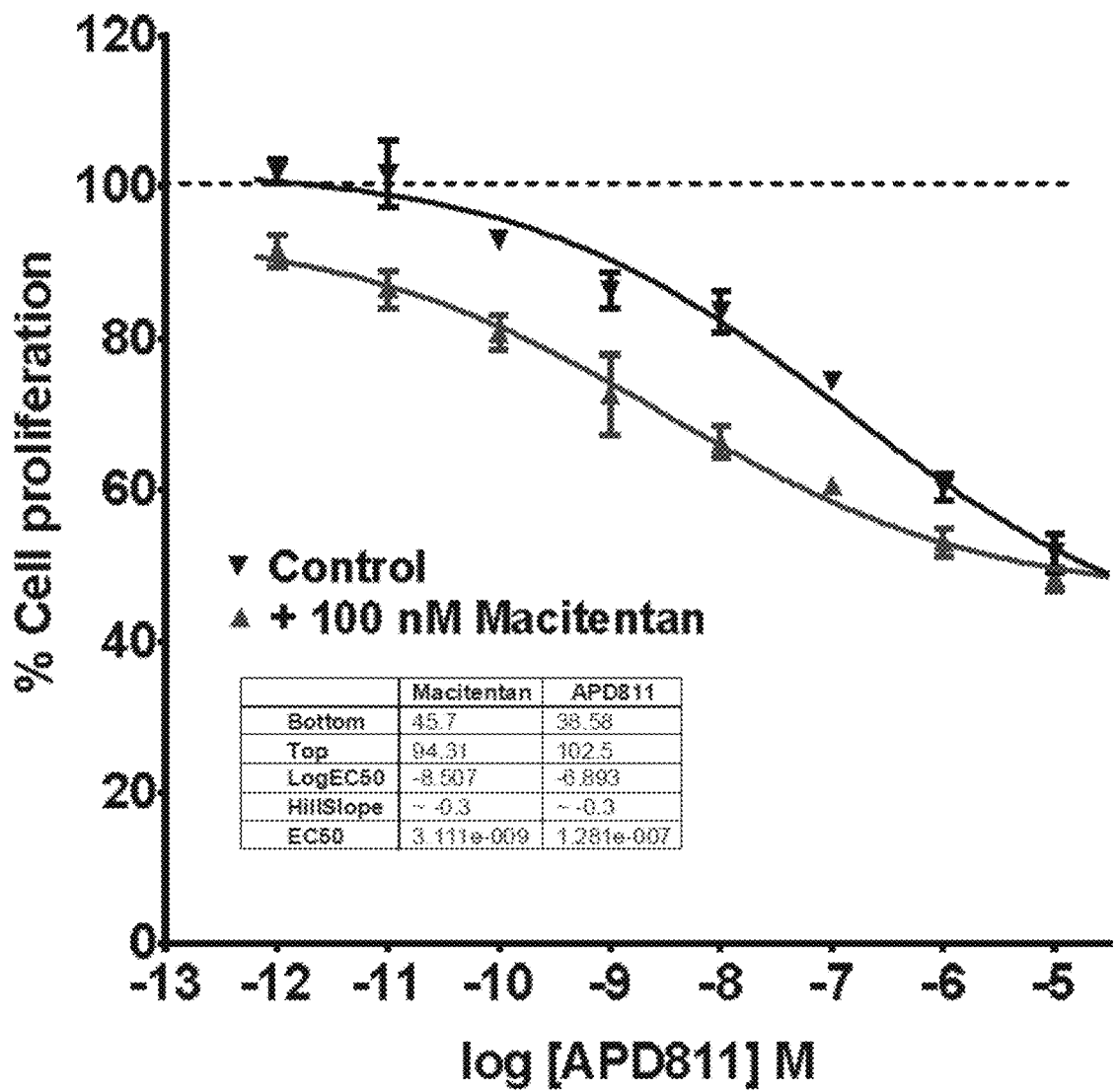
Figure 7D:
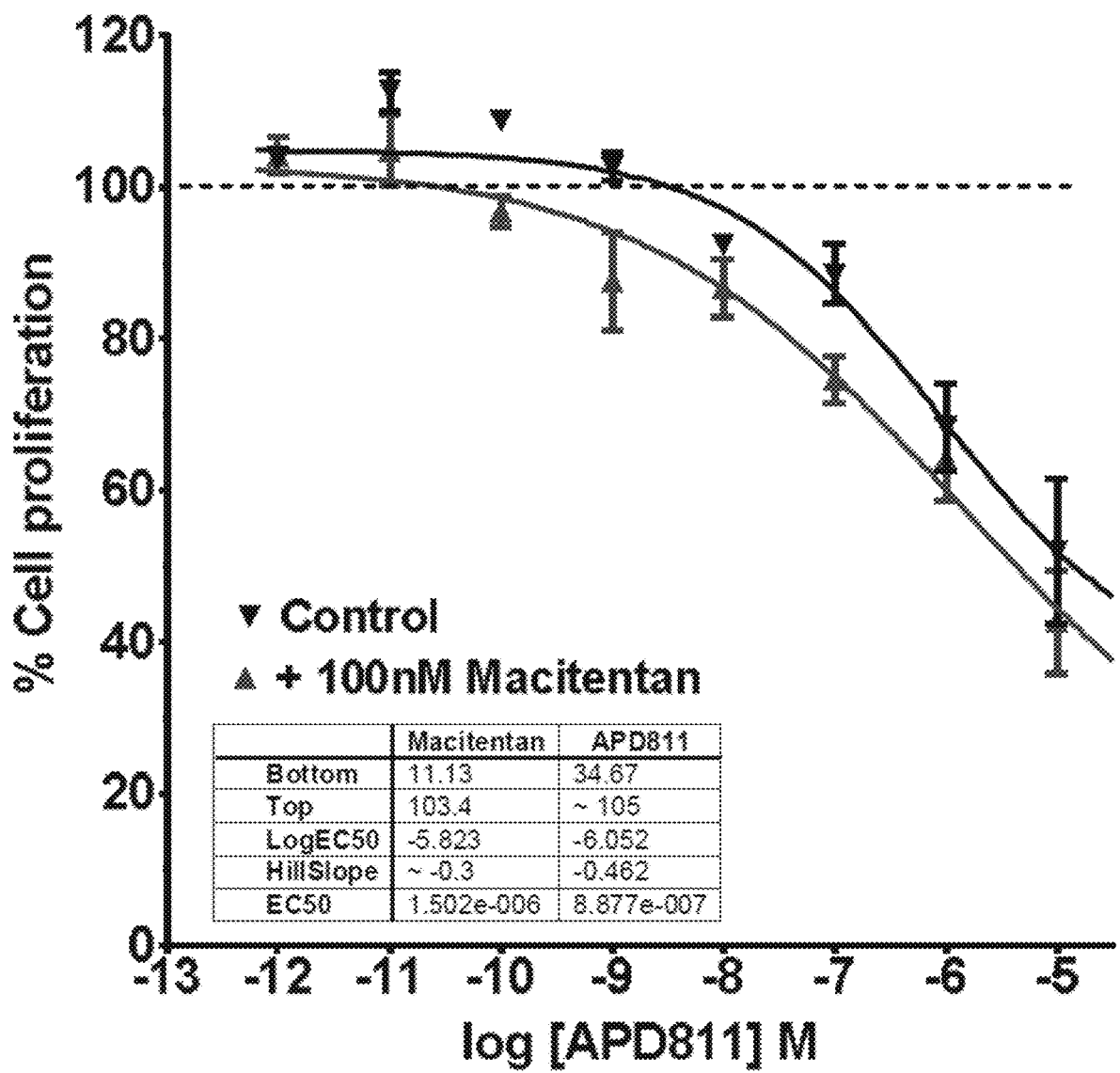
Figure 7E:
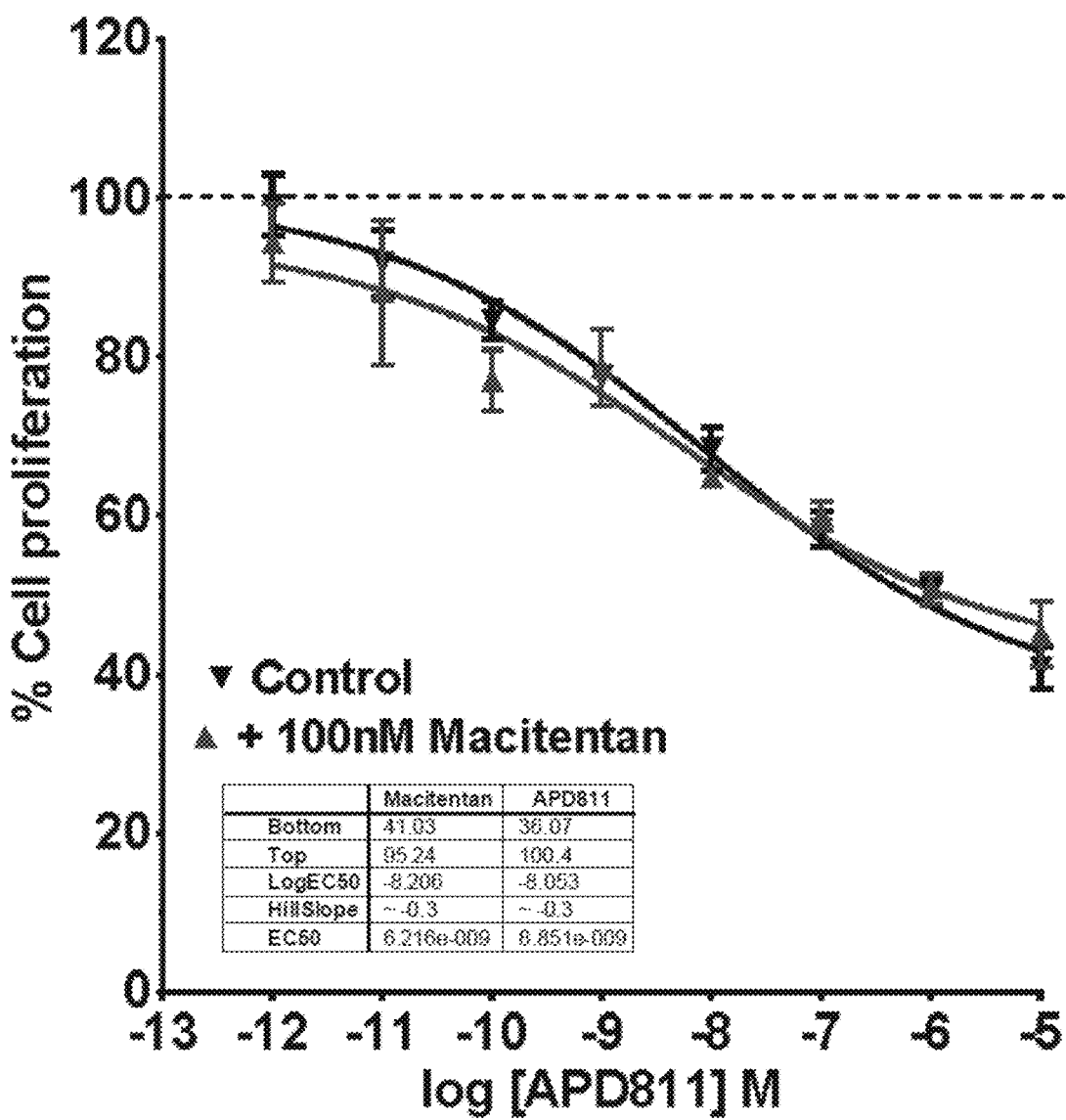
Figure 7F:
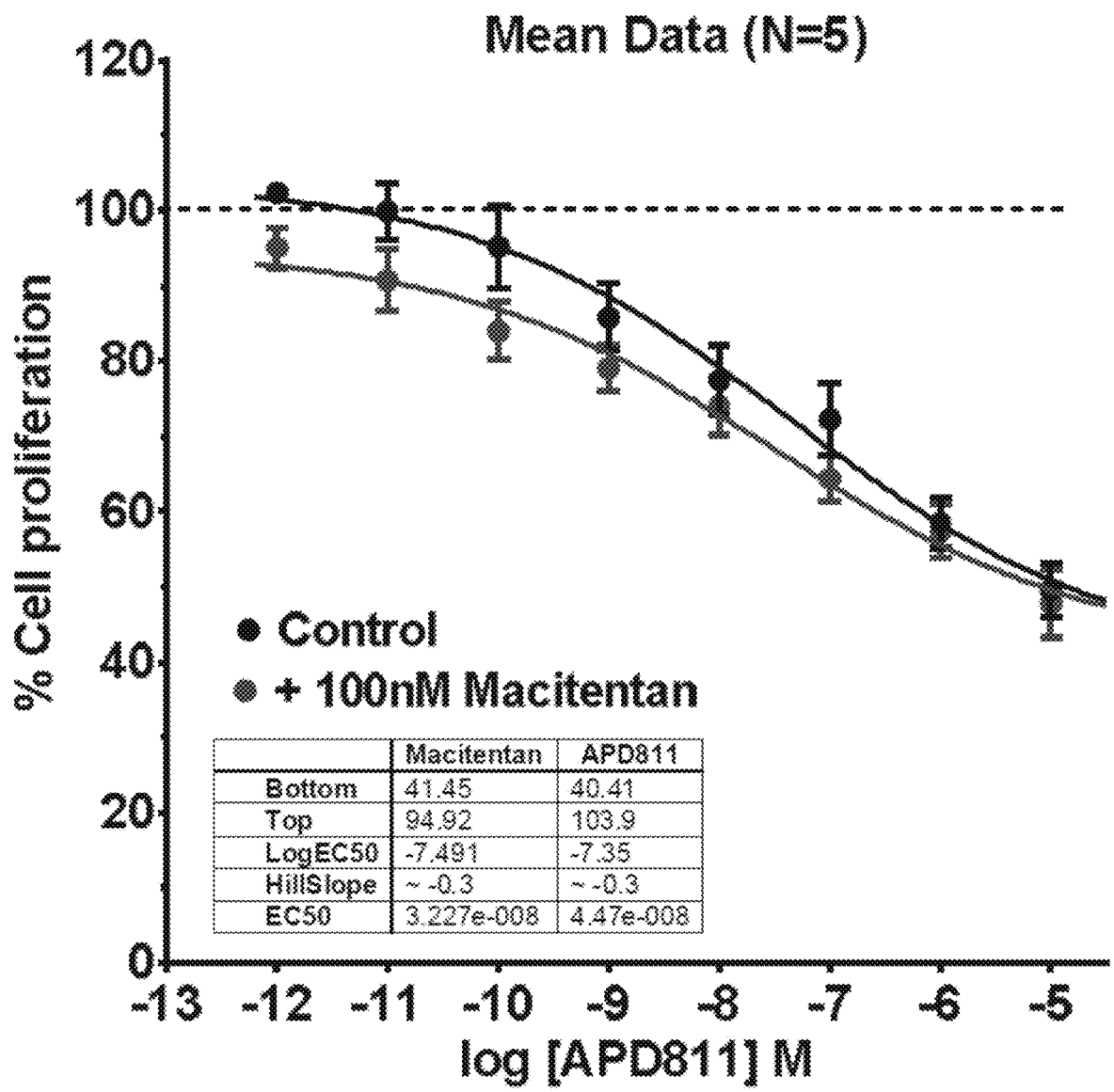

Mean antiproliferative effects of ralinepag in the absence and presence of 100 nM treprostinil compared with responses to 9% serum and 0.1% DMSO alone are shown in FIG. 6. Treprostinil significantly inhibited growth at 100 nM compared to serum and DMSO alone. When combined with ralinepag, significant inhibition of cell growth occurred at a 10-fold lower dose (0.1 nM) of ralinepag. At the highest dose tested (10 µM), ralinepag produced a 69% inhibition of cell growth as opposed to 50% in the absence of treprostinil. This greater inhibition of serum-induced cell proliferation can be accounted for in part by the magnitude of the inhibition induced by treprostinil alone, and suggests that both agents are inhibiting cell proliferation via separate pathways.

That treprostinil enhanced ralinepag responses might be surprising given that both agents are IP agonists and would presumably activate the same pathway to inhibit cell proliferation. Treprostinil is also a potent activator of EP2 and DP1 receptors (reviewed in Clapp & Gurung, 2015), which may explain the greater response to ralinepag in the presence of treprostinil. In experiments provided herein, it was observed that the antiproliferative responses to treprostinil were only weakly inhibited by an IP receptor antagonist, whereas those responses to ralinepag were completely inhibited.

Antiproliferative Effects of Ralinepag in Combination with Endothelin-1 Receptor Antagonists (ERAs)

The antiproliferative effects of ralinepag in the absence and presence of 100 nM macitentan in human PASMCs grown in 9% serum and 0.1% DMSO for 4 days are shown in FIG. 7. Macitentan (100 nM) only weakly affected responses to ralinepag when combined, and in two out of the five cell isolates, did not enhance the antiproliferative effects at any concentration of ralinepag investigated. In the other three cell isolates, there was a trend to a greater inhibition of cell growth, which was more apparent at the lower doses of ralinepag when combined with 100 nM macitentan. However, overall from the mean data, ralinepag was not significantly more effective in the presence of macitentan compared to ralinepag alone.

Figure 8:
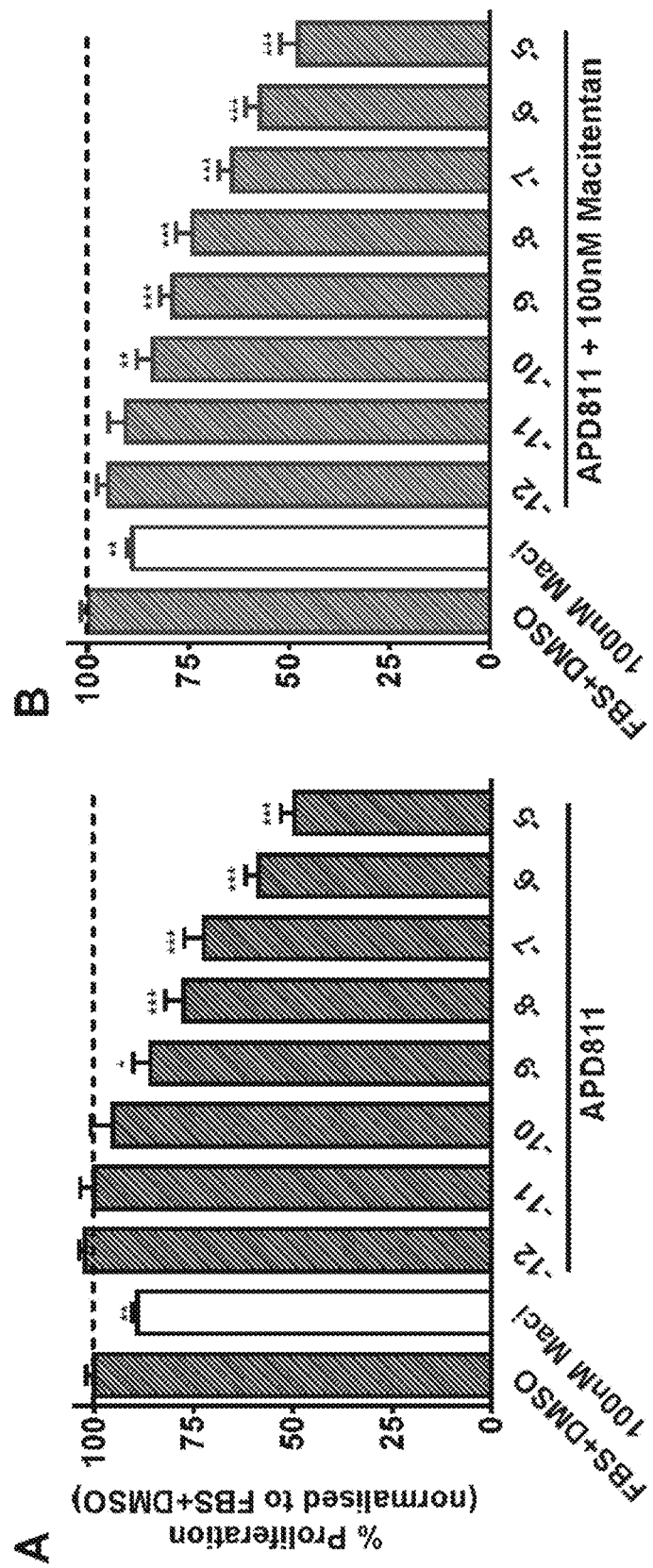
FIG. 8 shows the effect of macitentan on the antiproliferative response of ralinepag in human PASMCs from PAH patients. Mean anti-proliferative effects of increasing doses of ralinepag in the absence (A) and presence of 100 nM macitentan (B). Human PASMCs were grown in 9% serum (FBS) and 0.1% DMSO for 4 days±drug(s). Cell proliferation was normalized to the growth response induced by FBS alone, which was taken as the FBS response minus the time control (=100% growth at 4 days). Growth responses induced in the presence of ralinepag and solvent±macitentan are shown as % change in cell proliferation relative to the FBS response alone. Shown on the graph is the effect macitentan (Maci; 100 nM) in the presence of growth medium containing solvent. *=P<0.05, =P<0.01, *=P<0.001 when compared to control (FBS and DMSO); 1-WAY ANOVA with Bonferroni post hoc test (n=5).
Figure 9A:
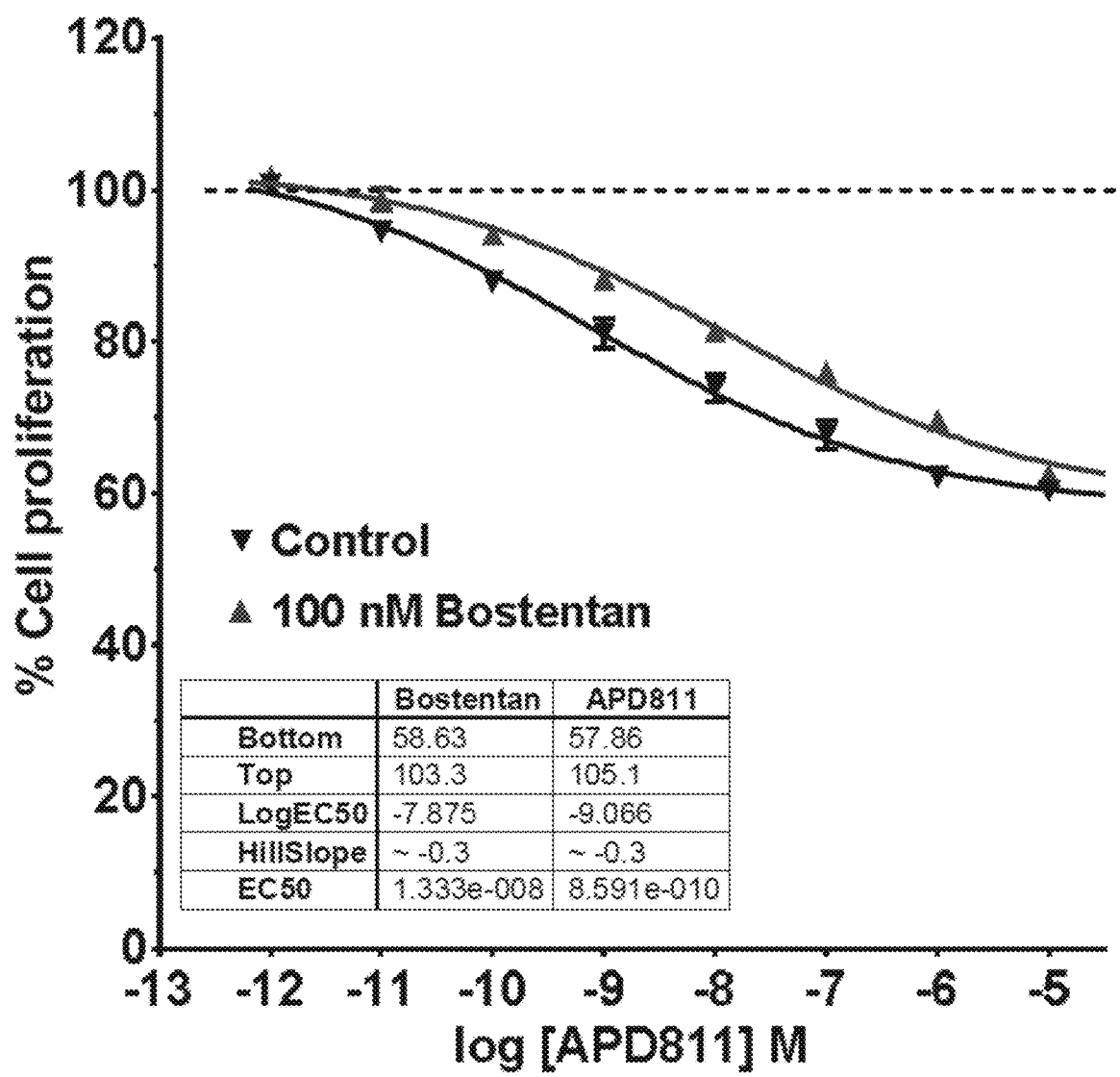
FIGS. 9A-9F show antiproliferative effects of ralinepag in combination with 100 nM bosentan. Growth arrested cells were incubated for 96 hours in human smooth muscle basal medium (SMBM) containing either 9% FBS+0.1% DMSO, FBS plus ralinepag and DMSO in the absence and presence of 100 nM bosentan or SMBM alone (time control). Cell proliferation was normalized to the growth response induced by FBS alone, which was taken as the FBS response minus the time control (=100% growth at 4 days). Growth responses induced in the presence of ralinepag plus solvent are shown as % change in cell proliferation relative to the FBS response alone. Data were fit using a variable slope sigmoidal-curve fitting routine in GraphPad and parameters of each fit are shown. Data are from 5 individual patient cell isolates.
Figure 9B:
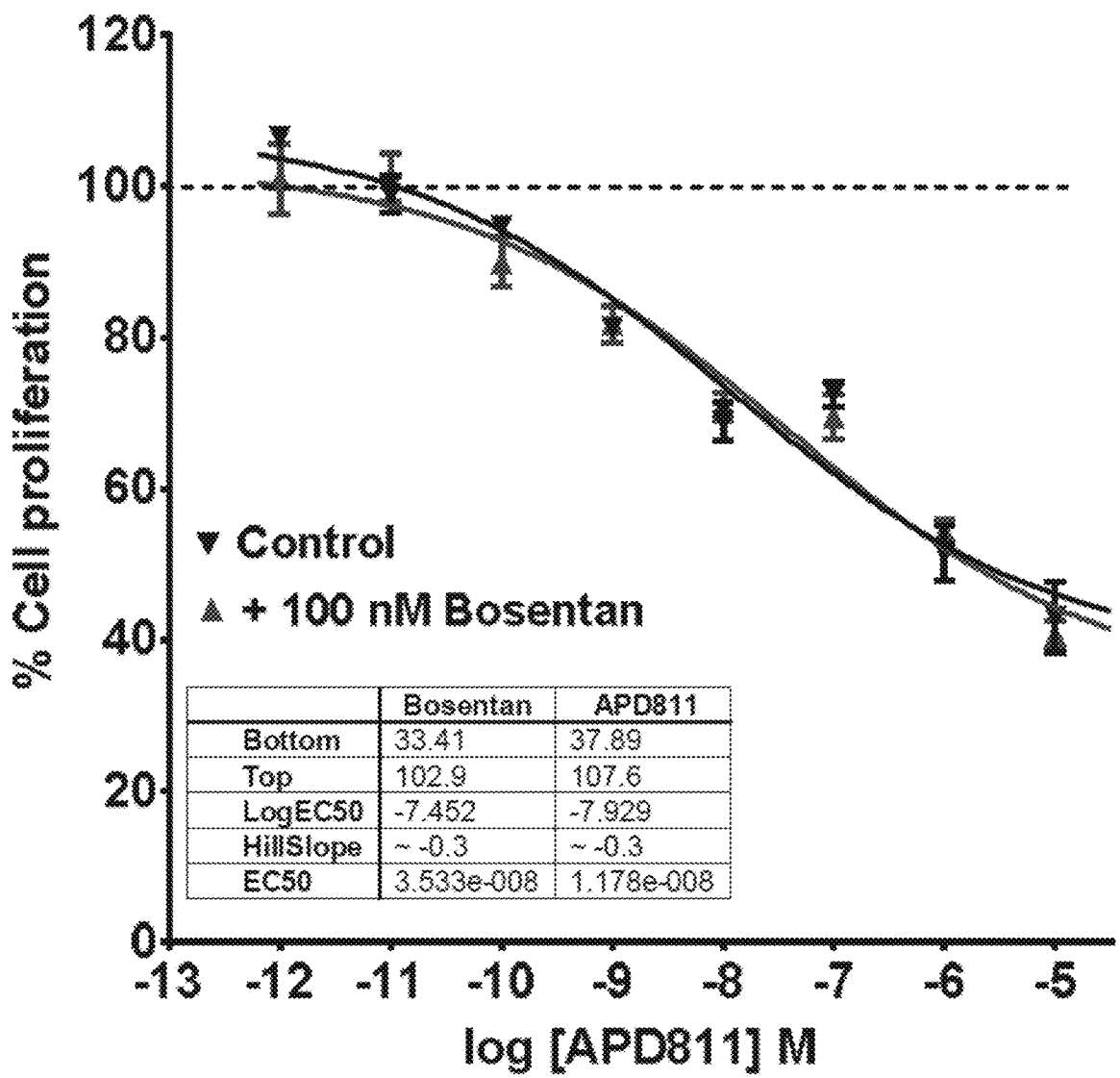
Figure 9C:
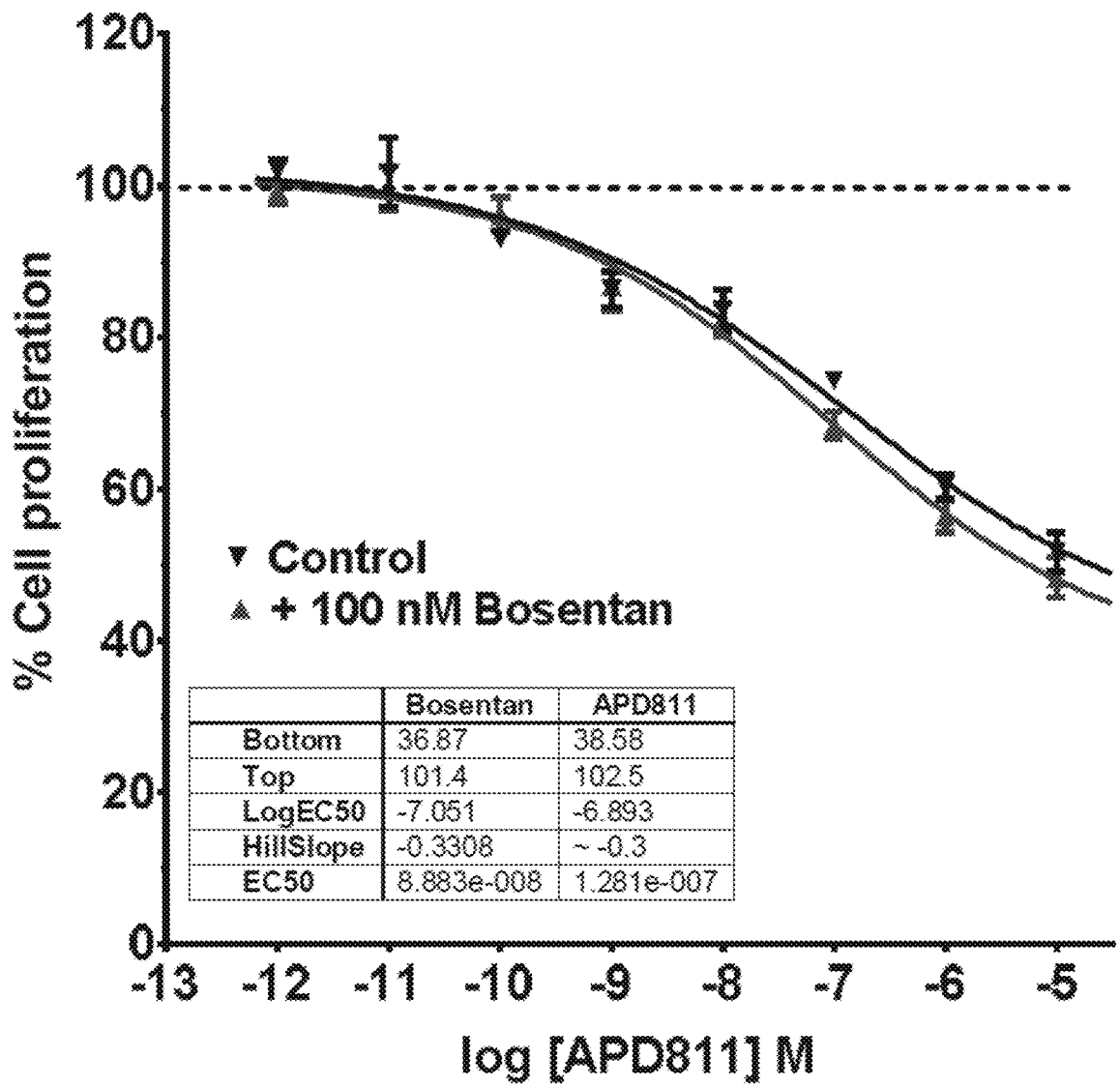
Figure 9D:
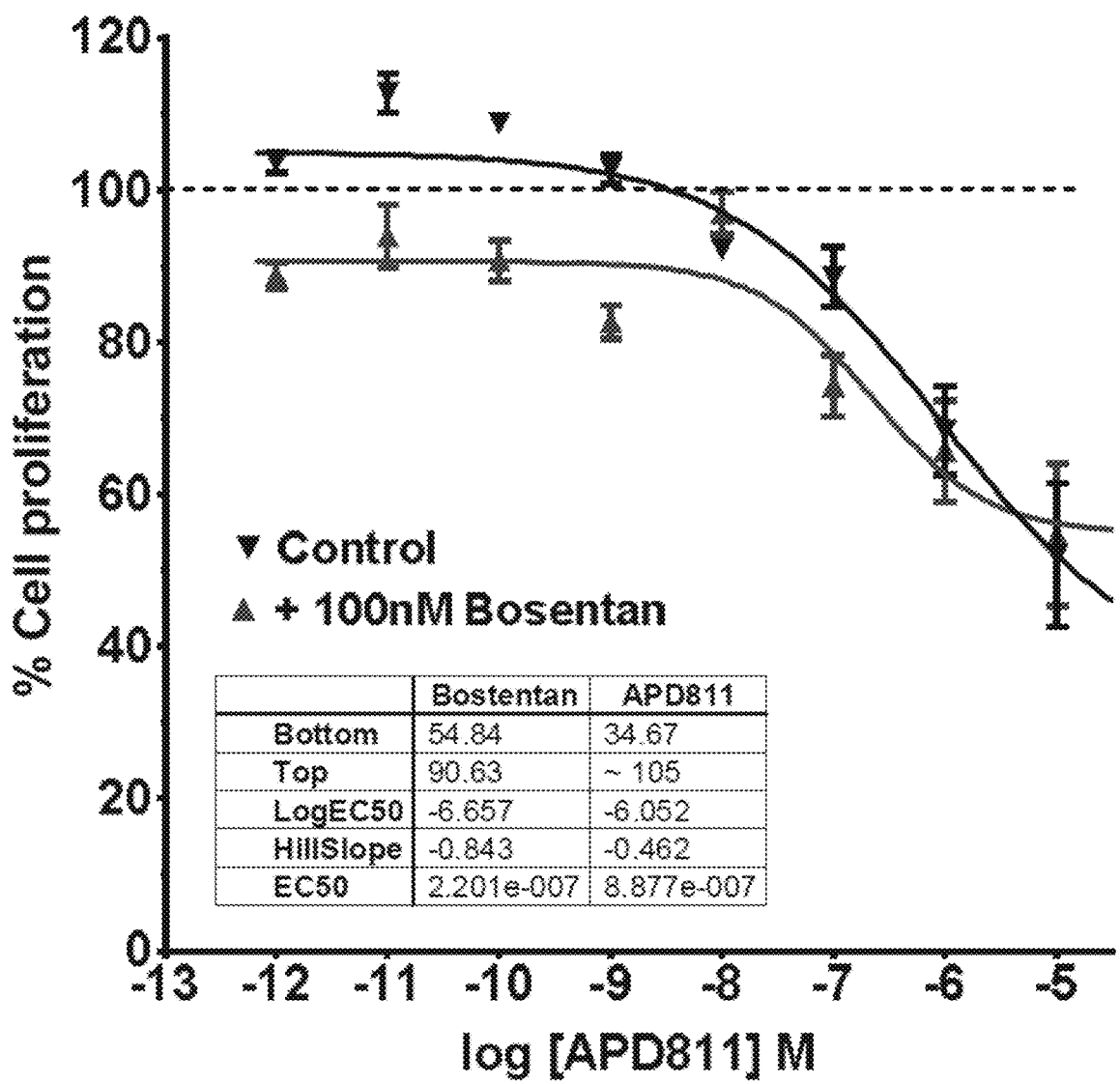
Figure 9E:
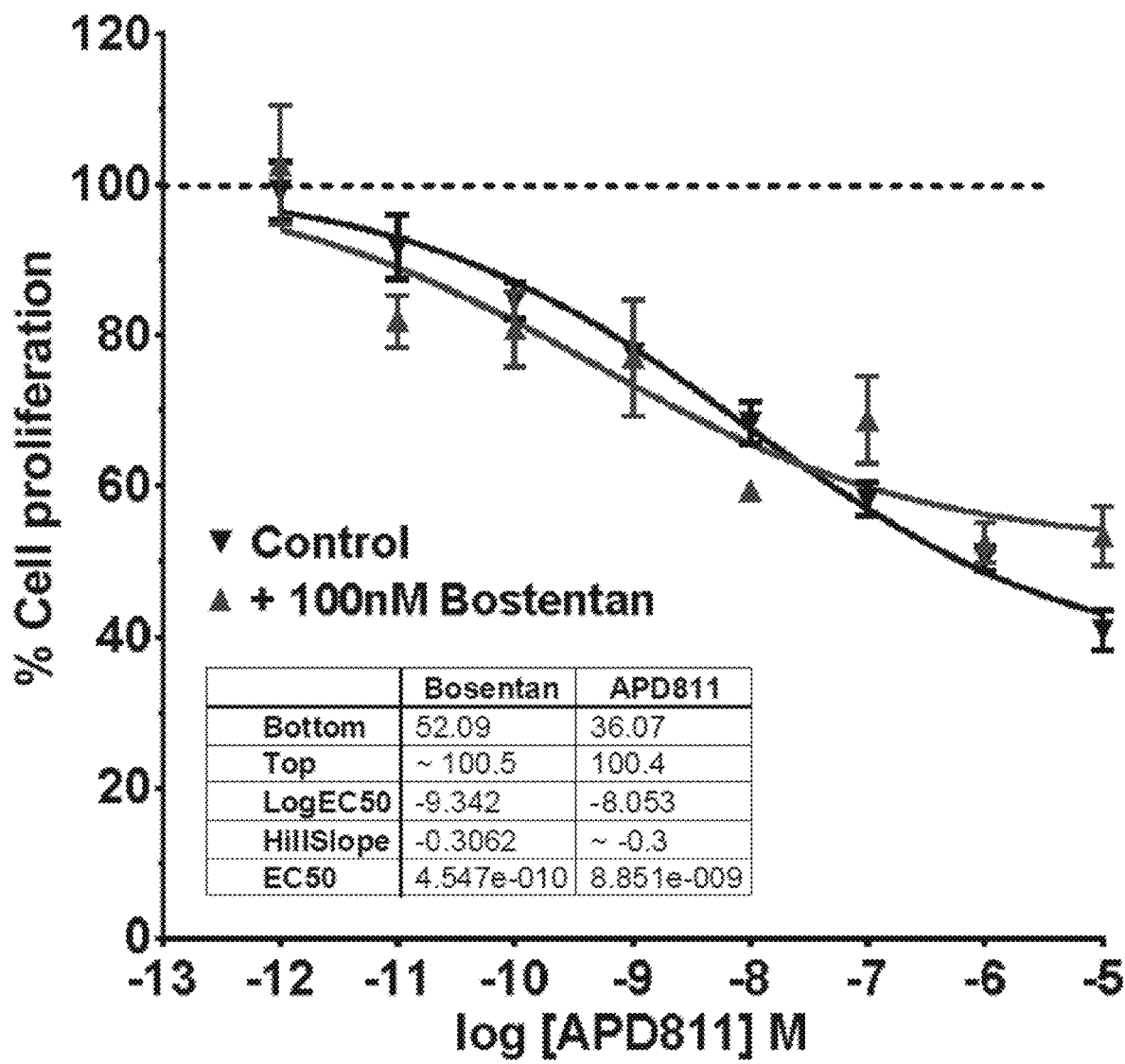
Figure 9F:
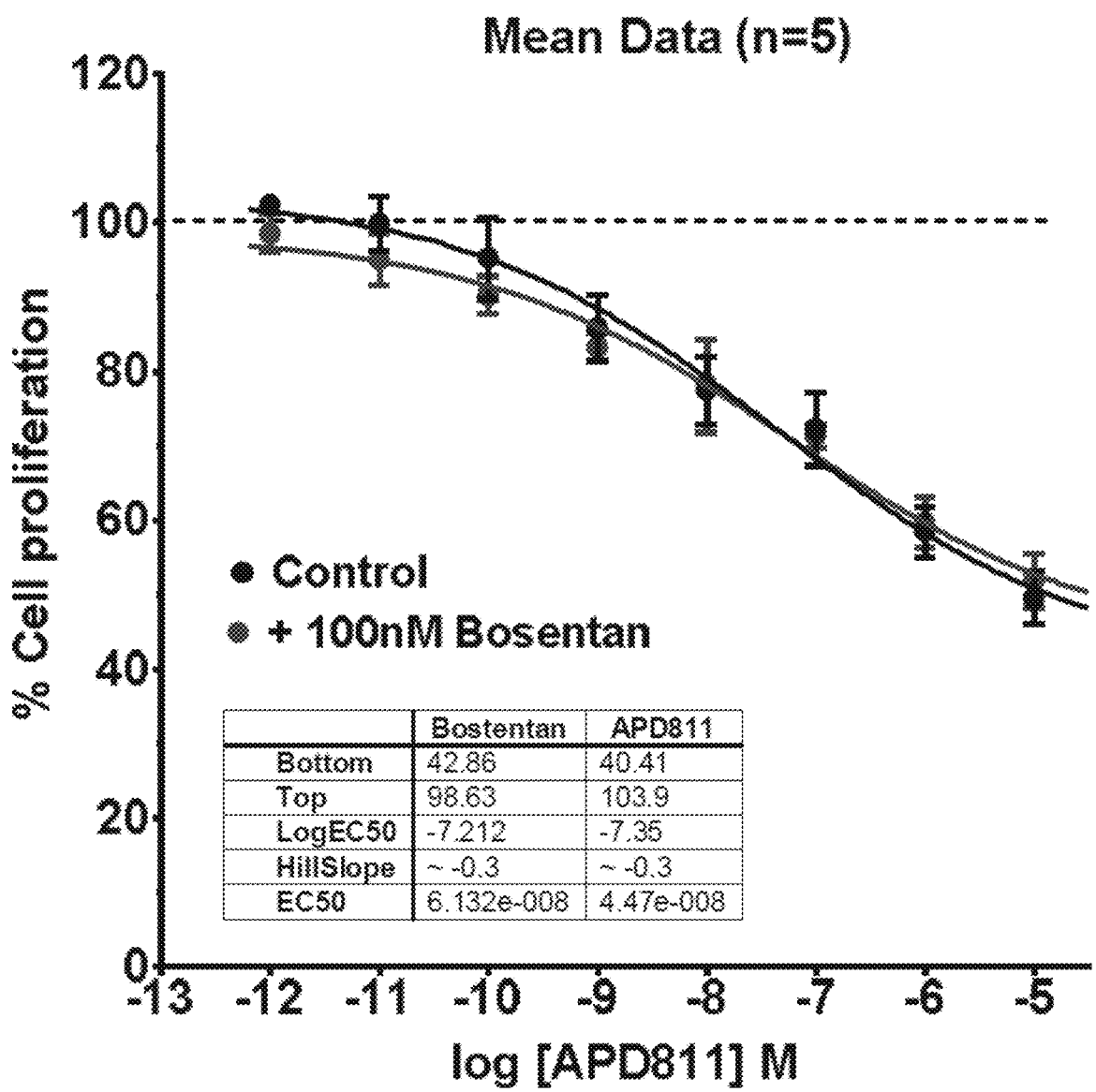

Mean antiproliferative effects of ralinepag in the absence and presence of 100 nM macitentan compared with responses to 9% serum and 0.1% DMSO alone are shown in FIG. 8. Macitentan alone (100 nM) caused a significant inhibition (~12%) of cell proliferation compared to serum and DMSO. Furthermore, when combined with macitentan, ralinepag inhibited cell proliferation at a 10-fold lower dose (0.1 nM) compared to ralinepag alone. At higher concentrations of ralinepag (>10 nM), effects converged, such that responses to ralinepag were similar in the absence or presence of macitentan.

The modes of action of these two drugs may overlap, and thus provide no real added benefit when combined. Macitentan is a mixed ET-1 antagonist, inhibiting binding to ETA and ETB receptors with a mean IC50 value of 0.5 nM and 391 nM, respectively (Iglarz et al., 2014). Thus at the concentration used, macitentan would predominately inhibit ETA receptors, receptors known to contribute to ET-1 induced cell proliferation of distal human PASMCs (Zamora et al., 1993; Davie et al., 2002). On the other hand, prostacyclin analogues inhibit serum or transforming growth factor 3 (TGF-β) induced release of ET-1 in human distal PASMCs, and such a mechanism is postulated in part to underlie the antiproliferative effects of prostacyclin analogues in normal human PASMCs (Wort et al., 2001; Davie et al., 2002).

Figure 10:
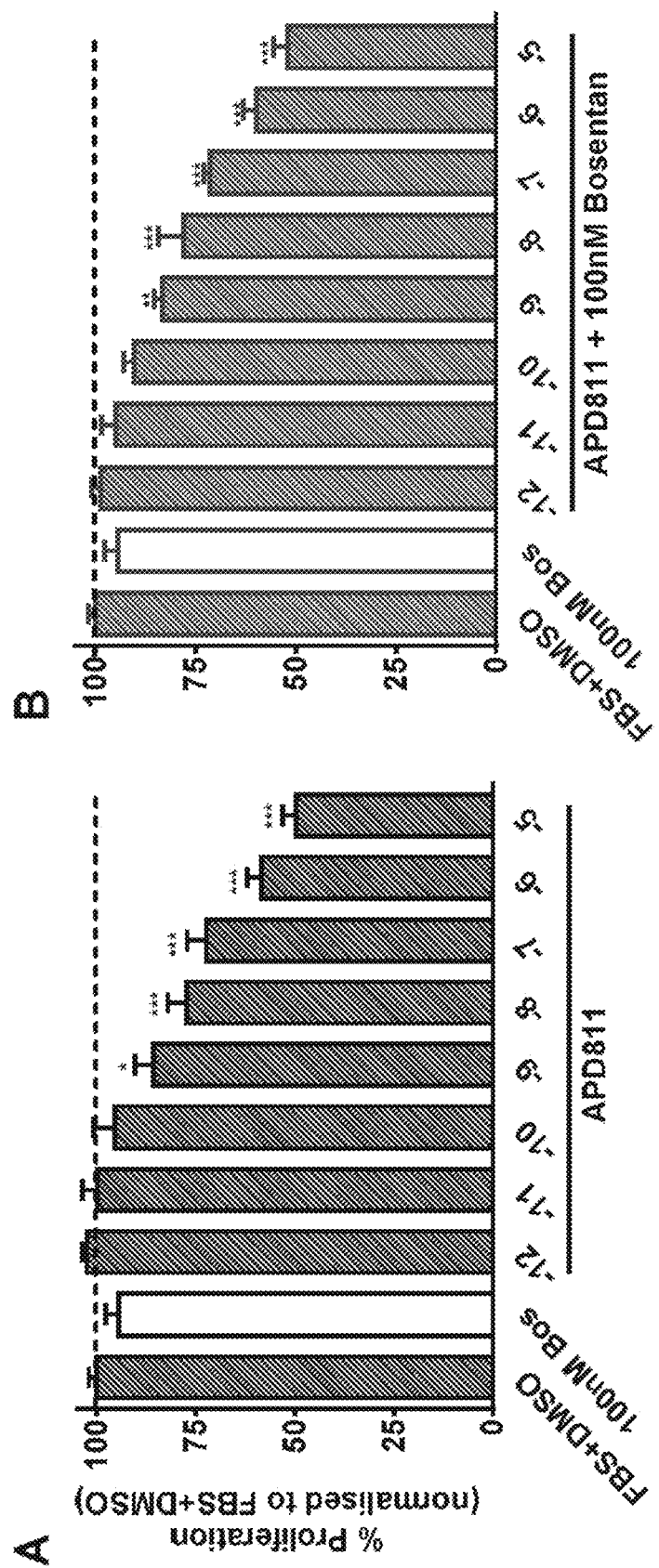
FIG. 10 shows the effect of bosentan on the antiproliferative response of ralinepag in human PASMCs from PAH patients. Mean anti-proliferative effects of increasing doses of ralinepag in the absence (A) and presence of 100 nM bosentan (B). Human PASMCs were grown in 9% serum (FBS) and 0.1% DMSO for 4 days±drug(s). Cell proliferation was normalized to the growth response induced by FBS alone, which was taken as the FBS response minus the time control (=100% growth at 4 days). Growth responses induced in the presence of ralinepag and solvent±bosentan are shown as % change in cell proliferation relative to the FBS response alone. Shown on the graph is the effect bosentan (Bos; 100 nM) in the presence of growth medium containing solvent. *=P<0.05, =P<0.01, *=P<0.001 when compared to control (FBS and DMSO); 1-WAY ANOVA with Bonferroni post hoc test (n=5).
Figure 11A:
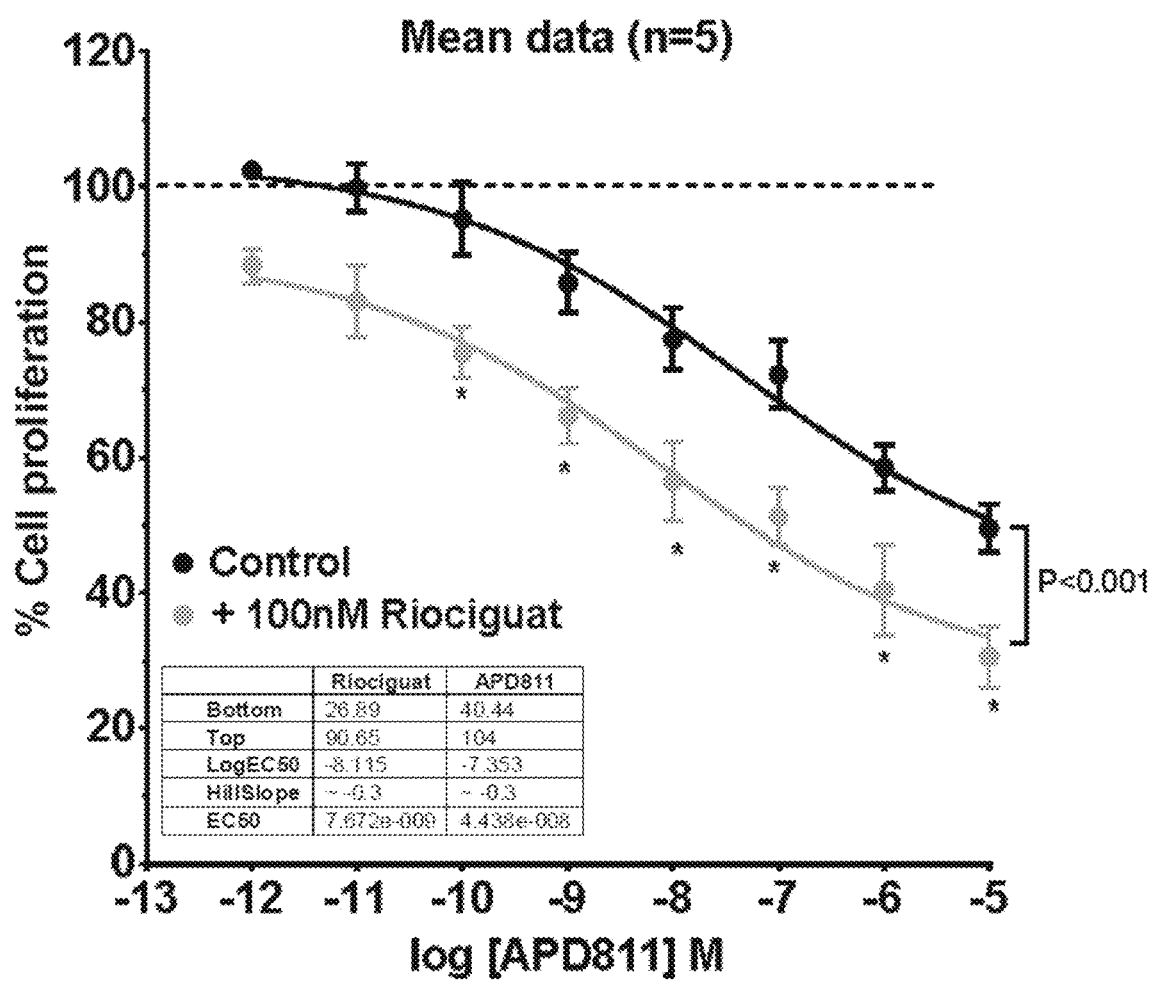
FIGS. 11A-11E show combinations of PAH therapies with ralinepag on cell proliferation in human PASMC cells. Comparisons were made in cells derived from the same PAH patients and passage and had been grown in 9% serum (FBS) and 0.1% DMSO for 4 days and treated with ralinepag±riociguat (A), sildenafil (B), treprostinil (C), macitentan (D), or bosentan (E). Cell proliferation was normalized to the growth response induced by FBS plus solvent. Data are shown as mean±S.E.M. in fit using a variable slope sigmoidal-curve fitting routine in Graph Pad, with parameters of each fit shown. *=P<0.05 when compared to ralinepag alone; 1 WAY-ANOVA with Bonferroni post hoc test (n=5).
Figure 11B:
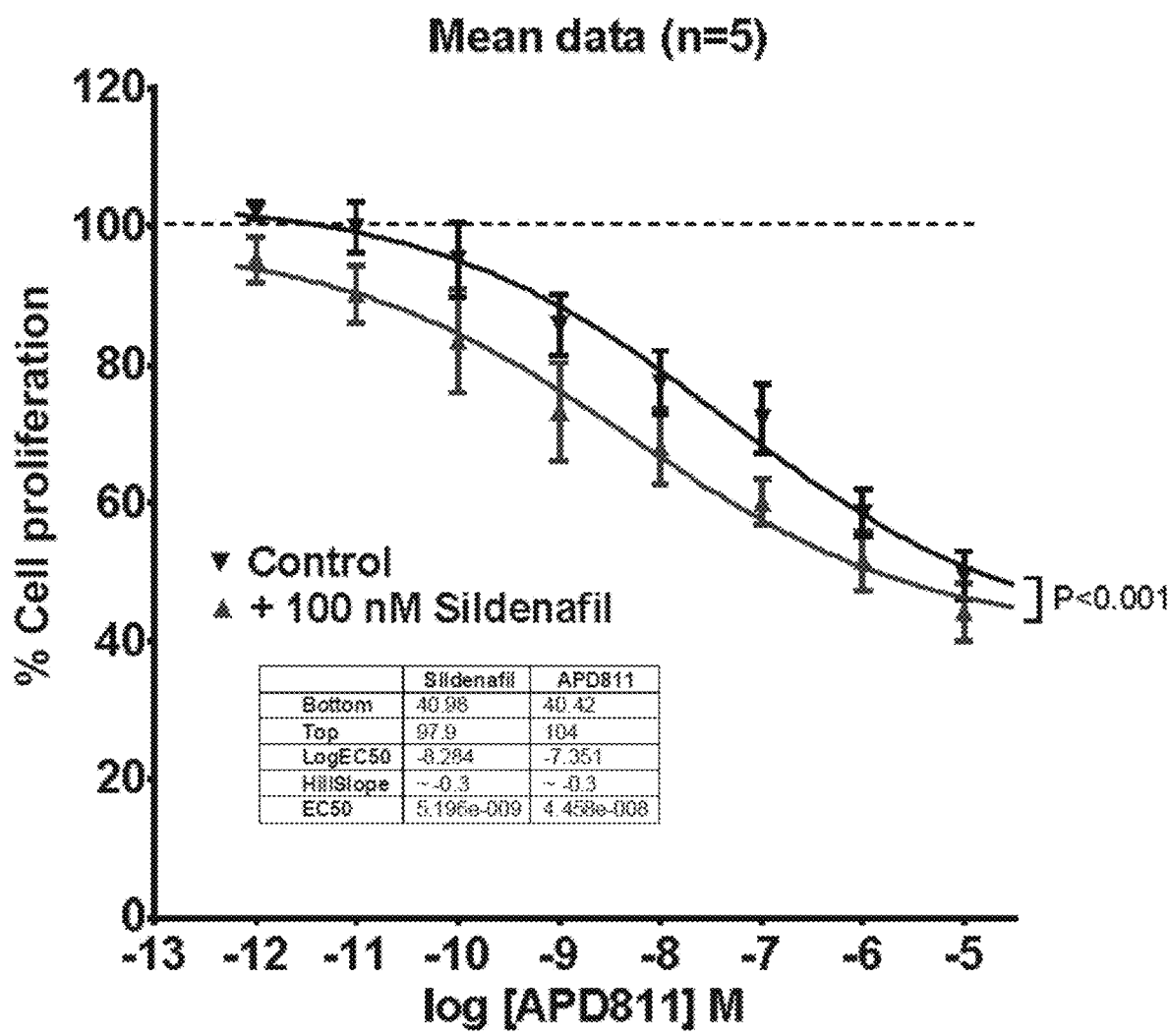
Figure 11C:
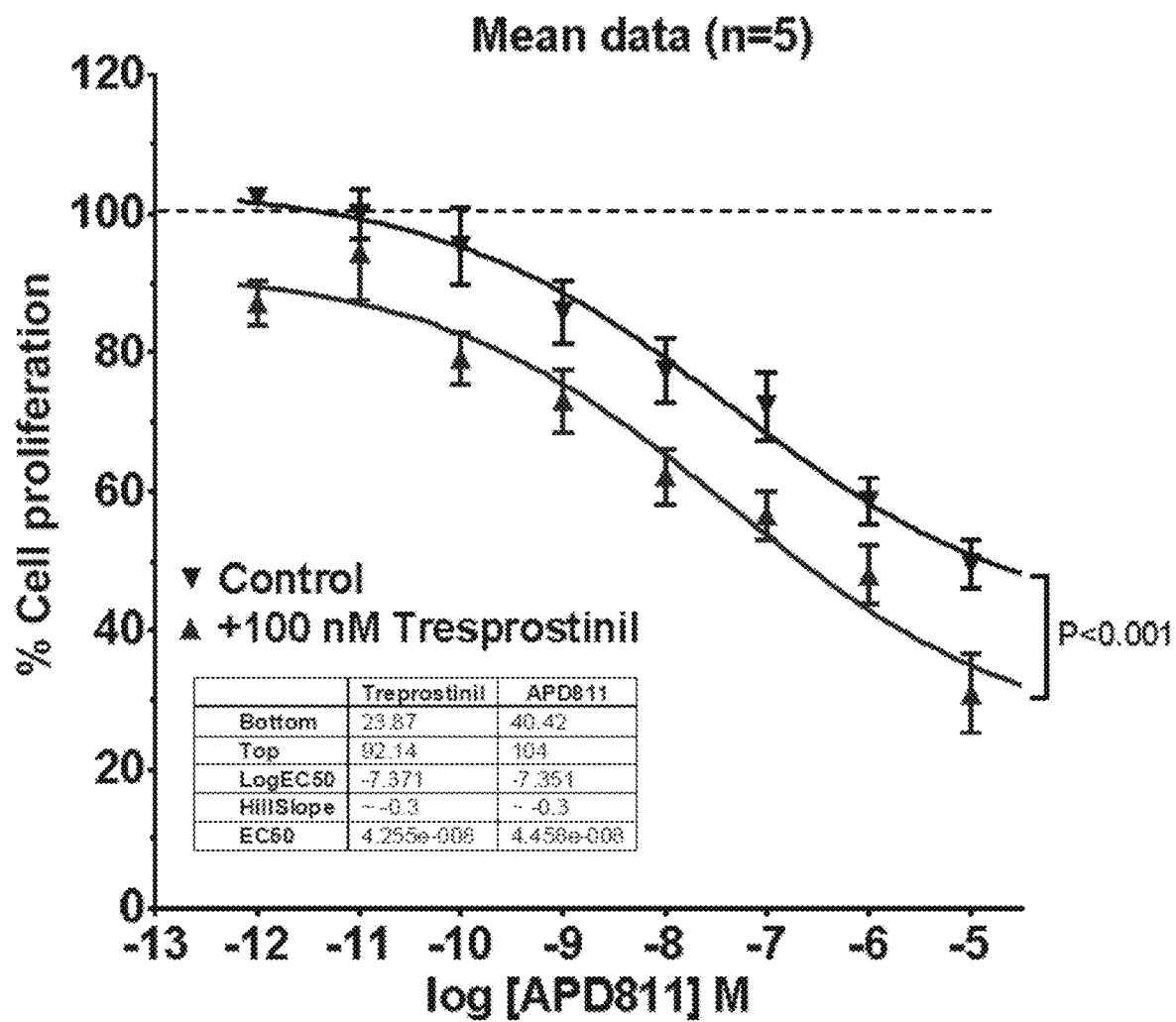
Figure 11D:
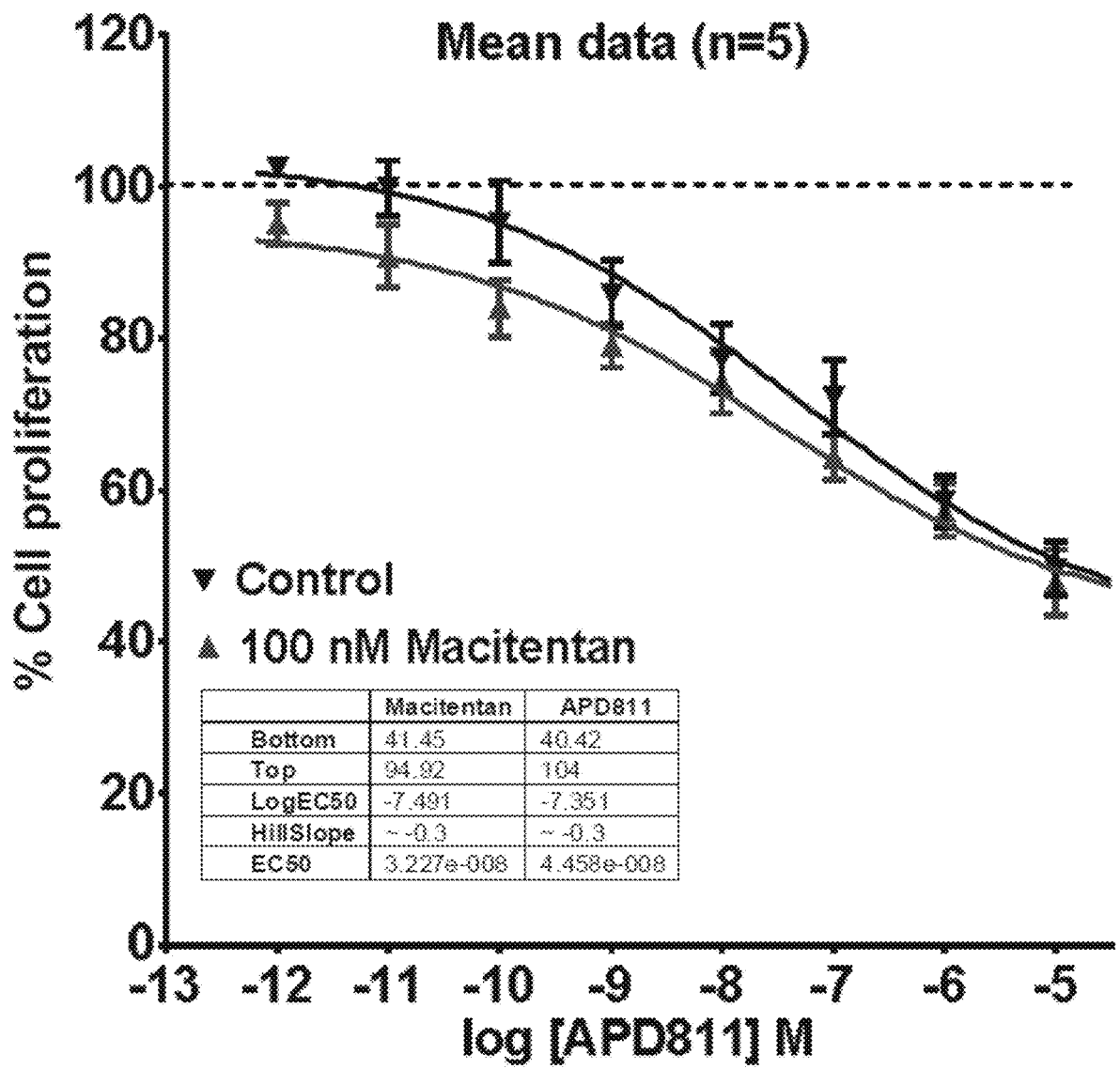
Figure 11E:
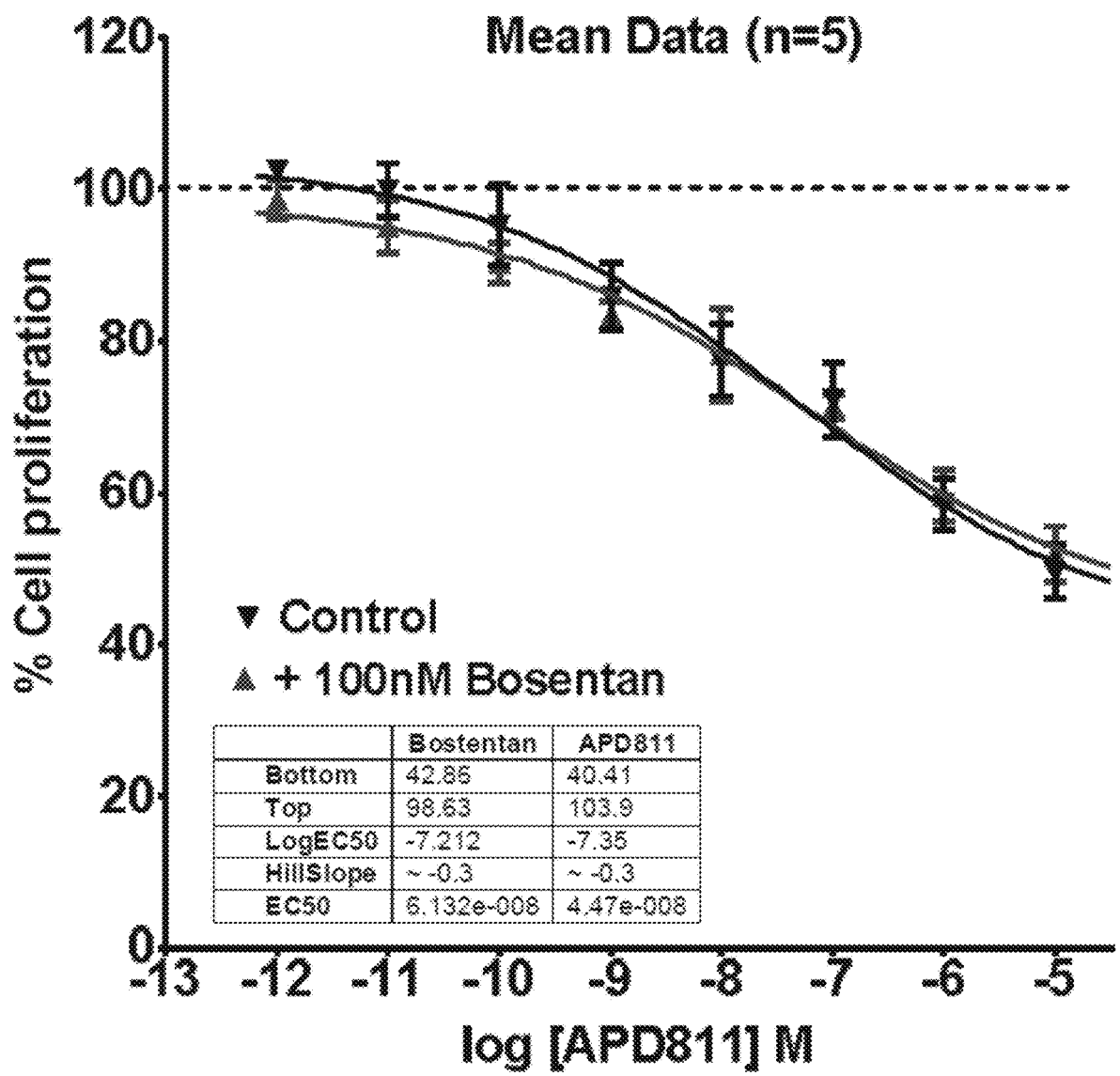

The antiproliferative effects of ralinepag in the absence and presence of 100 nM bosentan in human PASMCs grown in 9% serum and 0.1% DMSO for 4 days are shown in FIG. 9. In contrast to the other PAH drugs, bosentan did not enhance the antiproliferative response to ralinepag in four out of the five cell isolates, and in one cell isolate, actually decreased its response. Overall, from the mean data, ralinepag was not more effective in the presence of bosentan across the entire concentration. Shown in FIG. 10 are the mean antiproliferative effects of ralinepag in the absence and presence of 100 nM bosentan compared with responses to 9% serum and 0.1% DMSO alone. Unlike macitentan, bosentan (100 nM) did not cause a significant inhibition of cell proliferation when compared to serum and DMSO alone. Furthermore, when combined with ralinepag, bosentan did not enhance inhibition of cell proliferation compared to ralinepag alone, nor did it lower the concentration (lnM), at which ralinepag started to significantly inhibit cell proliferation as observed with all other agents (riociguat, treprostinil, and macitentan). Thus, bosentan appears to have less of an inhibitory effect on cell proliferation than macitentan, possibly related to its lower potency at the ETA receptor and/or differential receptor ET-1 receptor selectivity. While bosentan is like macitentan a mixed ET-1 receptor antagonist, its potency and selectivity ratio against ETA and ETB receptors is somewhat different as are its receptor kinetics. Bosentan has a 10-fold lower potency than macitentan with a $K_i$ of 4 nM for the ETA receptor, but only has a selectivity ratio of ETA/ETB of ~20 (Davie et al., 2009), compared to a selectivity ratio of 780 for macitentan (Iglarz et al., 2014).

Comparisons of Different PAH Drug Combinations with Ralinepag

Figure 12:
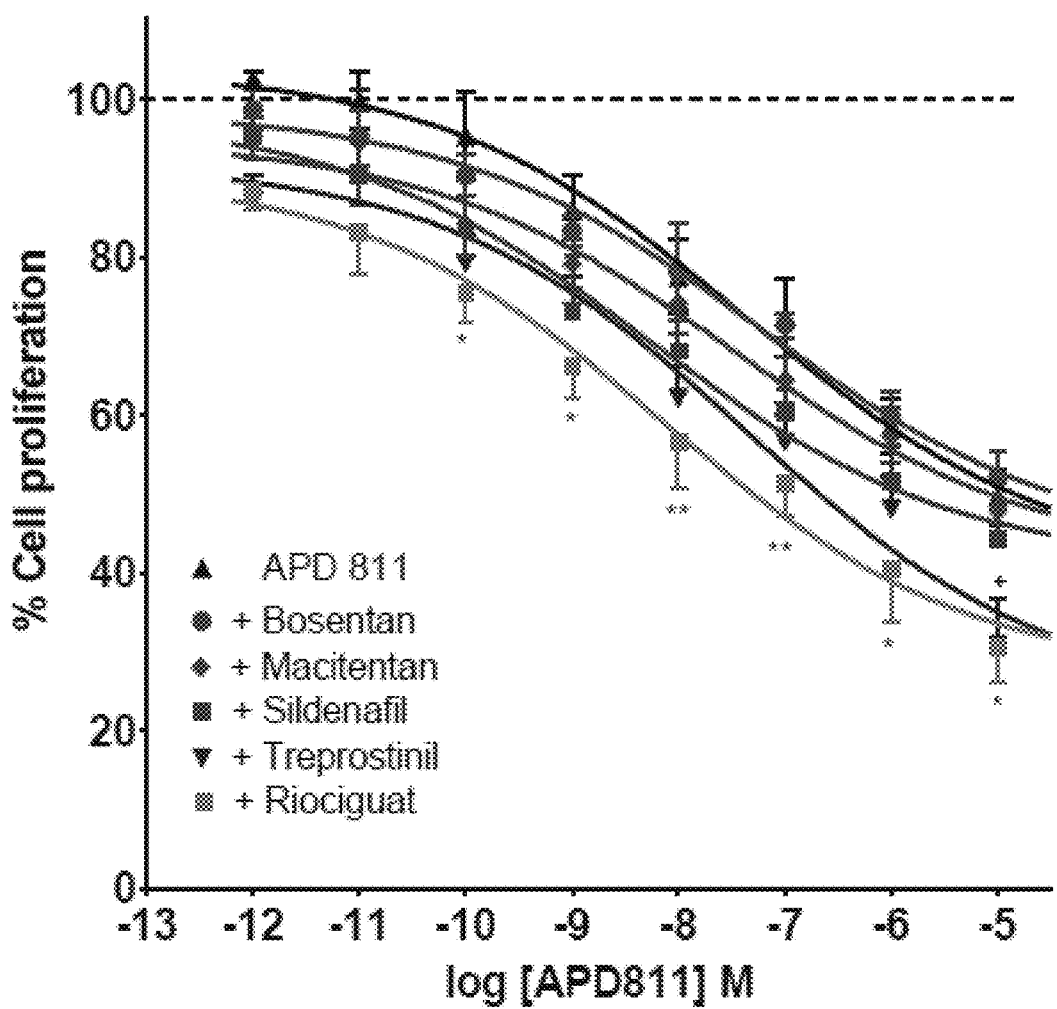
FIG. 12 shows comparisons of different PAH drug combinations with ralinepag on cell proliferation in human PASMCs from PAH patients. Data are shown as mean±S.E.M. and taken from FIGS. 1, 3, 5, 7, and 9. Concentration dependent effects of ralinepag on serum-induced growth are compared when this drug was combined with 100 nM of either bosentan, macitentan, sildenafil, treprostinil or riociguat. *=P<0.05, **=P<0.01 when compared to ralinepag; 2 WAY-ANOVA with Bonferroni post hoc test.

It appears that cGMP elevating agents and treprostinil combine with ralinepag to provide a greater antiproliferative effect, whereas ETRAs do not significantly enhance ralinepag effects on cell proliferation (FIG. 11). At 10 nM ralinepag, growth was inhibited by 45% when combined with riociguat and by only 21% in the presence of bosentan (FIG. 12). Compared to riociguat, and to a lesser extent with treprostinil, there was however a smaller potentiating effect with sildenafil (no significant difference with a post-hoc test, even though there is a significant drug interaction). A summary of the antiproliferative effects of ralinepag in the absence and presence of different PAH therapies, where $EC_{50}$ and $E_{Max}$ values were obtained for each individual fit (using data contained in FIGS. 1, 3, 5, 7, and 9 are presented as the mean±S.E.M in Table 1. Table 1 shows that ralinepag is ~2.5-5 times more potent in the presence of riociguat and sildenafil, respectively ($EC_{50}$=10 nM and 5 nM). Overall, ralinepag produces a significantly greater maximum response in the presence of riociguat or treprostinil, but not when combined with other PAH therapies. An analysis where $EC_{50}$ and $E_M$ax values were obtained from fits to mean data (FIG. 11) are presented in Table 2. The $EC_{50}$ for ralinepag is slightly higher than from individual fits (44 nM as opposed to 25 nM), though potency was still enhanced 8-fold in the presence of riociguat and sildenafil. Ralinepag still produced a significantly greater maximum response in the presence of riociguat or treprostinil, but not with the other PAH therapies.

TABLE 1

Mean anti-proliferative effects of ralinepag in combination with other PAH drugs (extrapolated log $EC_{50}$ and Emax from individual fits)

| APD811 + 100 nM Drug | Log $EC_{50}$ (n = 5) | $EC_{50}$ | $E_{max}$ (% Inhibition) |
|---|---|---|---|
| APD811 | −7.60 ± 0.52 | 25 nM | 58.2 ± 4.1% |
| +Bosentan | −7.69 ± 0.47 | 20 nM | 52.8 ± 4.9% |
| +Macitentan | −7.42 ± 0.62 | 38 nM | 65.3 ± 9.8% |
| +Sildenafil | −8.30 ± 0.53 | 5 nM | 58.5 ± 4.7% |
| +Treprostinil | −7.29 ± 0.35 | 51 nM | 77.2 ± 6.6% |
| +Riociguat | −8.01 ± 0.55 | 10 nM | 76.0 ± 4.7% |

TABLE 2

Mean anti-proliferative effects of ralinepag in combination with other PAH drugs (extrapolated log $EC_{50}$ and Emax from mean fits)

| Drug | Log $EC_{50}$ (n = 5) | $EC_{50}$ | $E_{max}$ (% Inhibition) |
|---|---|---|---|
| APD811 | −7.35 ± 0.79 | 44 nM | 59.6 ± 17.3% |
| +Bosentan | −7.21 ± 0.83 | 61 nM | 57.1 ± 15.6% |
| +Macitentan | −7.49 ± 0.76 | 32 nM | 58.5 ± 13.9% |
| +Sildenafil | −8.28 ± 0.72 | 5 nM | 59.0 ± 13.1% |
| +Treprostinil | −7.37 ± 0.86 | 42 nM | 76.1 ± 20.1% |
| +Riociguat | −8.12 ± 0.72 | 6 nM | 73.1 ± 13.1% |

Example 2: Clinical Trial

A 22-week randomized, double-blind, placebo-controlled study with a dose titration period of up to 9 weeks was conducted. Sixty-one patients were randomized 2:1 ralinepag to placebo. Right Heart Catheterization (RHC) measurements were obtained prior to study Day 1 of the dose titration period and at Week 22. The following values were obtained and recorded: pulmonary artery pressure (PAP) (systolic, diastolic, and mean), heart rate (HR), right atrial pressure (RAP), pulmonary capillary wedge pressure (PCWP) right ventricular pressure (RVP) and cardiac output (CO), pulmonary vascular resistance (PVR), arterial and mixed venous oxygen saturation (FiO2) (if applicable). Systemic vascular resistance (SVR) was estimated from blood pressure measurements. All patients were receiving background PAH treatment with an endothelin receptor antagonist, phosphodiesterase type-5-inhibitor, or soluble guanylate cyclase activator, alone or in combination.

The primary efficacy endpoint for the study was change from baseline in PVR after 22 weeks of treatment. Additional analyses included change from baseline in 6 MWD after 22 weeks of treatment, hemodynamics, and safety and tolerability. Ralinepag was administered as a capsule in 0.01, 0.02, 0.03, 0.04, and 0.10 mg dose strengths.

The starting dose of ralinepag was 0.01 mg twice daily. The dose of ralinepag was titrated according to patient tolerability. If the initial dose was tolerated (0.01 mg twice daily), then the dose was increased once a week in the following fashion: 0.02 mg twice daily, 0.03 mg twice daily, 0.04 mg twice daily, 0.06 mg twice daily, 0.08 mg, 0.1 mg twice daily, 0.2 mg twice daily and 0.3 mg twice daily. The dose was optionally escalated to a possible maximum total daily dose of 0.6 mg (0.3 mg twice daily), pending tolerability. If a dose was not tolerated, ralinepag was optionally decreased to the previous dose level. If the initial dose of 0.01 mg twice daily was not tolerated, dosing was optionally decreased to 0.01 mg once daily.

Ralinepag achieved the primary endpoint with a statistically significant change from baseline in pulmonary vascular resistance (PVR) compared to placebo. Ralinepag also demonstrated numerical improvement in 6-minute walk distance (6MWD). Adverse events observed in the study were consistent with other prostacyclin treatments for the management of PAH. The distribution of maintenance doses for patients receiving ralinepag was as follows: 0.02 mg (n=1), 0.03 mg (n=1), 0.04 mg (n=0), 0.06 mg (n=3), 0.08 mg (n=3), 0.12 mg (n=5), 0.16 mg (n=4), 0.2 mg (n=6), 0.4 mg (n=12), and 0.6 mg (n=5).

All documents, including patent and nonpatent literature cited herein are each incorporated herein by reference in their entirety for all purposes.

REFERENCES

1. Ballard S A, Gingell C J, Tang K, Turner L A, Price M E, & Naylor A M (1998). Effects of sildenafil on the relaxation of human corpus cavernosum tissue in vitro and on the activities of cyclic nucleotide phosphodiesterase isozymes. *J Urol* 159, 2164-2171.
2. Barst R J, McGoon M, McLaughlin V, Tapson V, Rich S, Rubin L, Wasserman K, Oudiz R, Shapiro S, Robbins I M, Channick R, Badesch D, Rayburn B K, Flinchbaugh R, Sigman J, Arneson C, & Jeffs R (2003). Beraprost therapy for pulmonary arterial hypertension. *J Am Coll Cardiol* 41, 2119-2125.
3. Benyahia C, Boukais K, Gomez I, Silverstein A M, Clapp L H, Fabre A, Danel C, Leseche G, Longrois D, & Norel X (2013). A comparative study of PGI2 mimetics used clinically on the vasorelaxation of human pulmonary arteries and veins, role of the DP-receptor. *Prostaglandins & Other Lipid Mediators* 107, 48-55.
4. Bischoff E (2004). Potency, selectivity, and consequences of nonselectivity of PDE inhibition. *Int J Impot Res* 16 Suppl 1, S11-S14.
5. Bley K R, Bhattacharya A, Daniels D V, Gever J, Jahangir A, O'yang C, Smith S, Srinivasan D, Ford A P, & Jett M F (2006). RO1138452 and RO3244794: characterization of structurally distinct, potent and selective IP (prostacyclin) receptor antagonists. *Br J Pharmacol* 147, 335-345.
6. Bubb K J, Trinder S L, Baliga R S, Patel J, Clapp L H, MacAllister R J, & Hobbs A J (2014). Inhibition of phosphodiesterase 2 augments cGMP and cAMP signaling to ameliorate pulmonary hypertension. *Circulation* 130, 496-507.
7. Burgess G, Hoogkamer H, Collings L, & Dingemanse J (2008). Mutual pharmacokinetic interactions between steady-state bosentan and sildenafil. *Eur J Clin Pharmacol* 64, 43-50.
8. Clapp L H, Finney P A, Turcato S, Tran S, Rubin L J, & Tinker A (2002). Differential effects of stable prostacyclin analogues on smooth muscle proliferation and cyclic AMP generation in human pulmonary artery. *Am J Respir Cell Molec Biol* 26, 194-201.
9. Clapp L H & Gurung R (2015). The mechanistic basis of prostacyclin and its stable analogues in pulmonary arterial hypertension: Role of membrane versus nuclear receptors. *Prostaglandins Other Lipid Mediat* 120, 56-71.
10. Davie N, Haleen S J, Upton P D, Polak J M, Yacoub M H, Morrell N W, & Wharton J (2002). ETA and ETB receptors modulate the proliferation of human pulmonary artery smooth muscle cells. *Am J Respir Crit Care Med* 165, 398-405.
11. Davie N J, Schermuly R T, Weissmann N, Grimminger F, & Ghofrani H A (2009). The science of endothelin-1 and endothelin receptor antagonists in the management of pulmonary arterial hypertension: current understanding and future studies. *Eur J Clin Invest* 39 Suppl 2, 38-49.
12. Falcetti E, Hall S M, Phillips P G, Patel J, Morrell N W, Haworth S G, & Clapp L H (2010). Smooth muscle proliferation and role of the prostacyclin (I P) receptor in idiopathic pulmonary arterial hypertension. *Am J Respir Crit Care Med* 182, 1161-1170.
13. Galie N, Barbera J A, Frost A E, Ghofrani H A, Hoeper M M, McLaughlin V V, Peacock A J, Simonneau G, Vachiery J L, Grunig E, Oudiz R J, Vonk-Noordegraaf A, White R J, Blair C, Tadalafil in Pulmonary Arterial Hypertension. *N Engl J Med* 373, 834-844.
14. Grimminger F, Weimann G, Frey R, Voswinckel R, Thamm M, Bolkow D, Weissmann N, Muck W, Unger S, Wensing G, Schermuly R T, & Ghofrani H A (2009). First acute haemodynamic study of soluble guanylate cyclase stimulator riociguat in pulmonary hypertension. *Eur Respir J* 33, 785-792.
15. Hoeper M M, Leuchte H, Halank M, Wilkens H, Meyer F J, Seyfarth H J, Wensel R, Ripken F, Bremer H, Kluge S, Hoeffken G, & Behr J (2006). Combining inhaled iloprost with bosentan in patients with idiopathic pulmonary arterial hypertension. *Eur Respir J* 28, 691-694.
16. Humbert M, Barst R J, Robbins I M, Channick R N, Galie N, Boonstra A, Rubin L J, Horn E M, Manes A, & Simonneau G (2004). Combination of bosentan with epoprostenol in pulmonary arterial hypertension: BREATHE-2. *Eur Respir J* 24, 353-359.
17. Iglarz M, Bossu A, Wanner D, Bortolamiol C, Rey M, Hess P, & Clozel M (2014). Comparison of pharmacological activity of macitentan and bosentan in preclinical models of systemic and pulmonary hypertension. *Life Sci* 118, 333-339.
18. Jabr R I, Wilson A J, Riddervold M H, Jenkins A H, Perrino B A, & Clapp L H (2007). Nuclear translocation of calcineurin Aβ but not calcineurin Aα by platelet-derived growth factor in rat aortic smooth muscle. Am JPhysiol 292, C2213-C2225.
19. Kam Y, Chow K B, & Wise H (2001). Factors affecting prostacyclin receptor agonist efficacy in different cell types. *Cell Signal* 13, 841-847.
20. Knebel S M, Elrick M M, Bowles E A, Zdanovec A K, Stephenson A H, Ellsworth M L, & Sprague R S (2013). Synergistic effects of prostacyclin analogs and phosphodiesterase inhibitors on cyclic adenosine 3',5' monophosphate accumulation and adenosine 3'5' triphosphate release from human erythrocytes. *Exp Biol Med (Maywood)* 238, 1069-1074.
21. Kuwano K, Hashino A, Asaki T, Hamamoto T, Yamada T, Okubo K, & Kuwabara K (2007). 2-[4-[(5,6-diphenylpyrazin-2-yl)(isopropyl)amino]butoxy]-N-(methylsulfonyl)acetamide (NS-304), an orally available and long-acting prostacyclin receptor agonist prodrug. *J Pharmacol Exp Ther* 322, 1181-1188.
22. Lai Y J, Pullamsetti S S, Dony E, Weissmann N, Butrous G, Banat G A, Ghofrani H A, Seeger W, Grimminger F, & Schermuly R T (2008). Role of the prostanoid EP4 receptor in iloprost mediated vasodilatation in pulmonary hypertension. *Am J Respir Crit Care Med* 178, 188-196.
23. Lang M, Kojonazarov B, Tian X, Kalymbetov A, Weissmann N, Grimminger F, Kretschmer A, Stasch J P, Seeger W, Ghofrani H A, & Schermuly R T (2012). The soluble guanylate cyclase stimulator riociguat ameliorates pulmonary hypertension induced by hypoxia and SU5416 in rats. *PLoS One* 7, e43433.
24. Langleben D, Galie N, He J, Huang Y, Humbert M, Keogh A, Rubin L J, Zhou D, Curram J, Davie N, & Ghofrani H A (2015). Use of clinically relevant responder threshold criteria to evaluate the response to treatment in the phase III PATENT-1 study. *J Heart Lung Transplant* 34, 338-347.
25. Lu J, Wang X, Xie X, Han D, Li S, & Li M (2013). Calcineurin/NFAT signaling pathway mediates endothelin-1-induced pulmonary artery smooth muscle cell proliferation by regulating phosphodiesterase-5. *Nan Fang Yi Ke Da Xue Xue Bao* 33, 26-29.
26. McLaughlin V, Channick R N, Ghofrani H A, Lemarie J C, Naeije R, Packer M, Souza R, Tapson V F, Tolson J, Al H H, Meyer G, & Hoeper M M (2015). Bosentan added to sildenafil therapy in patients with pulmonary arterial hypertension. *Eur Respir J* 46, 405-413.
27. McLaughlin V V, Archer S L, Badesch D B, Barst R J, Farber H W, Lindner J R, Mathier M A, McGoon M D, Park M H, Rosenson R S, Rubin L J, Tapson V F, & Varga J (2009). ACCF/AHA 2009 expert consensus document on pulmonary hypertension a report of the American College of Cardiology Foundation Task Force on Expert Consensus Documents and the American Heart Association developed in collaboration with the American College of Chest Physicians; American Thoracic Society, Inc.; and the Pulmonary Hypertension Association. *J Am Coll Cardiol* 53, 1573-1619.
28. Murray F, Patel H H, Suda R Y, Zhang S, Thistlethwaite P A, Yuan J X, & Insel P A (2007). Expression and activity of cAMP phosphodiesterase isoforms in pulmonary artery smooth muscle cells from patients with pulmonary hypertension: role for PDE1. *Am J Physiol Lung Cell Mol Physiol* 292, L294-L303.
29. Orie N N, Ledwozyw A, Williams D J, Whittle B J, & Clapp L H (2013). Differential actions of the prostacyclin analogues treprostinil and iloprost and the selexipag metabolite, MRE-269 (ACT-333679) in rat small pulmonary arteries and veins. *Prostaglandins & Other Lipid Mediators* 106, 1-7.
30. Patel J A, Hall S M, Abraham D J, Nelsen A C, Silverstein A M, & Clapp L H. Comparison of current therapies to inhibit endothelin-induced growth of pulmonary artery smooth muscle cells (PASMCs) derived from patients with pulmonary arterial hypertension. Eur. Respir. J. 44[Suppl. 58], P2355. 2014.
31. Patel J A, Shen L, Hall S M, Norel X, McAnulty R J, Silverstein A M, Whittle B J, & Clapp L H. EP2 receptors play a key role in meditating the anti-proliferative activity of treprostinil in smooth muscle cells derived from the lungs of pulmonary hypertensive patients. Am. J. Respir. Crit Care Med. 191, A5954. 2015.
32. Schermuly R T, Pullamsetti S S, Breitenbach S C, Weissmann N, Ghofrani H A, Grimminger F, Nilius S M, Schror K, Kirchrath J M, Seeger W, & Rose F (2007). Iloprost-induced desensitization of the prostacyclin receptor in isolated rabbit lungs. *Respir Res* 8, 4.
33. Schermuly R T, Stasch J P, Pullamsetti S S, MiddendorffR, Muller D, Schluter K D, Dingendorf A, Hackemack S, Kolosionek E, Kaulen C, Dumitrascu R, Weissmann N, Mittendorf J, Klepetko W, Seeger W, Ghofrani H A, & Grimminger F (2008). Expression and function of soluble guanylate cyclase in pulmonary arterial hypertension. *Eur Respir J* 32, 881-891.
34. Simonneau G, Rubin L J, Galie N, Barst R J, Fleming T R, Frost A E, Engel P J, Kramer M R, Burgess G, Collings L, Cossons N, Sitbon O, & Badesch D B (2008). Addition of sildenafil to long-term intravenous epoprostenol therapy in patients with pulmonary arterial hypertension: a randomized trial. *Ann Intern Med* 149, 521-530.
35. Sitbon O, Channick R, Chin K M, Frey A, Gaine S, Galie N, Ghofrani H A, Hoeper M M, Lang I M, Preiss R, Rubin L J, Di S L, Tapson V, Adzerikho I, Liu J, Moiseeva O, Zeng X, Simonneau G, & McLaughlin V V (2015). Selexipag for the Treatment of Pulmonary Arterial Hypertension. *N Engl J Med* 373, 2522-2533.
36. Skoro-Sajer N & Lang I M (2014). Selexipag for the treatment of pulmonary arterial hypertension. *Expert Opin Pharmacother* 15, 429-436.
37. Syed N I & Jones R L (2015). Assessing the agonist profiles of the prostacyclin analogues treprostinil and naxaprostene, particularly their DP1 activity. *Prostaglandins Leukot Essent Fatty Acids* 95, 19-29.
38. Tapson V F, Jing Z C, Xu K F, Pan L, Feldman J, Kiely D G, Kotlyar E, McSwain C S, Laliberte K, Arneson C, & Rubin L J (2013). Oral treprostinil for the treatment of pulmonary arterial hypertension in patients receiving background endothelin receptor antagonist and phosphodiesterase type 5 inhibitor therapy (the FREEDOM-C2 study): a randomized controlled trial. *Chest* 144, 952-958.
39. Turcato S & Clapp L H. Evidence that vasorelaxation induced by Gs coupled receptors is largely independent of cAMP in guinea-pig aorta. Journal of Molecular and Cellular Cardiology 30, A190. 1998. Ref Type: Abstract
40. Vachiery J L (2011). Prostacyclins in pulmonary arterial hypertension: the need for earlier therapy. *Adv Ther* 28, 251-269.

41. Wang J, Yang K, Xu L, Zhang Y, Lai N, Jiang H, Zhang Y, Zhong N, Ran P, & Lu W (2013). Sildenafil inhibits hypoxia-induced transient receptor potential canonical protein expression in pulmonary arterial smooth muscle via cGMP-PKG-PPARγ axis. *Am J Respir Cell Mol Biol* 49, 231-240.
42. Wharton J, Davie N, Upton P D, Yacoub M H, Polak J M, & Morrell N W (2000). Prostacyclin analogues differentially inhibit growth of distal and proximal human pulmonary artery smooth muscle cells. *Circulation* 102, 3130-3136.
43. Whittle B J, Silverstein A M, Mottola D M, & Clapp L H (2012). Binding and activity of the prostacyclin receptor (IP) agonists, treprostinil and iloprost, at human prostanoid receptors: treprostinil is a potent DP1 and EP2 agonist. *Biochem Pharmacol* 84, 68-75.
44. Wort S J, Woods M, Warner T D, Evans T W, & Mitchell J A (2001). Endogenously released endothelin-1 from human pulmonary artery smooth muscle promotes cellular proliferation: relevance to pathogenesis of pulmonary hypertension and vascular remodeling. *Am J Respir Cell Mol Biol* 25, 104-110.
45. Zamora M A, Dempsey E C, Walchak S J, & Stelzner T J (1993). BQ123, an ETA receptor antagonist, inhibits endothelin-1-mediated proliferation of human pulmonary artery smooth muscle cells. *Am J Respir Cell Mol Biol* 9, 429-433.
46. Zhang S, Patel H H, Murray F, Remillard C V, Schach C, Thistlethwaite P A, Insel P A, & Yuan J X (2007). Pulmonary artery smooth muscle cells from normal subjects and IPAH patients show divergent cAMP-mediated effects on TRPC expression and capacitative Ca2+ entry. *Am J Physiol Lung Cell Mol Physiol* 292, L1202-L1210.

What is claimed is:

1. A method of treating pulmonary arterial hypertension in a human, comprising administering to the human with pulmonary arterial hypertension a therapeutically effective amount of ralinepag, or a pharmaceutically acceptable salt, hydrate, or solvate thereof, in combination with a therapeutically effective amount of riociguat.
2. The method of claim 1, wherein the daily amount of riociguat that is administered to the human is selected from about 0.25 mg, about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, and about 5 mg.
3. The method of claim 1, wherein the daily amount of ralinepag that is administered to the human is selected from about 0.01 mg, about 0.02 mg, about 0.025 mg, about 0.03 mg, about 0.04 mg, about 0.05 mg, about 0.06 mg, about 0.065 mg, about 0.07 mg, about 0.075 mg, about 0.08 mg, about 0.09 mg, about 0.1 mg, about 0.12 mg, about 0.15 mg, about 0.16 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, and about 1.0 mg.
4. The method of claim 1, wherein the pulmonary arterial hypertension (PAH) is selected from a group consisting of: idiopathic PAH; familial PAH; PAH associated with: a collagen vascular disease, a congenital heart disease, portal hypertension, HIV infection, ingestion of a drug or toxin, hereditary hemorrhagic telangiectasia, splenectomy, pulmonary veno-occlusive disease (PVOD), or pulmonary capillary hemangiomatosis (PCH); and PAH with significant venous or capillary involvement.
5. The method of claim 1, wherein the amount of ralinepag is administered once daily.
6. The method of claim 1, wherein the amount of ralinepag is administered twice daily.
7. The method of claim 1, wherein the ralinepag is titrated.
8. The method of claim 1, wherein the amount of riociguat is administered once daily.
9. The method of claim 1, wherein the amount of riociguat is administered twice daily.
10. The method of claim 1, wherein the amount of riociguat is administered three times daily.
11. The method of claim 1, wherein the riociguat is titrated.
12. The method of claim 1, wherein the ralinepag is administered prior to riociguat.
13. The method of claim 1, wherein the ralinepag is administered simultaneously with riociguat.
14. The method of claim 1, wherein the ralinepag is administered subsequent to riociguat.
15. The method of claim 1, wherein the amount of ralinepag that is administered to the human is 0.05 mg once daily.
16. The method of claim 1, wherein the amount of ralinepag that is administered to the human is 0.10 mg once daily.
17. The method of claim 1, wherein the amount of ralinepag that is administered to the human is 0.15 mg once daily.
18. The method of claim 1, wherein the amount of ralinepag that is administered to the human is 0.20 mg once daily.
19. The method of claim 1, wherein the amount of ralinepag that is administered to the human is 0.25 mg once daily.
20. The method of claim 1, wherein the amount of ralinepag that is administered to the human is selected from 0.3 mg, 0.35 mg, 0.4 mg, 0.45 mg, 0.5 mg, 0.55 mg, 0.6 mg, 0.65 mg, 0.7 mg, 0.75 mg, and 0.8 mg once daily.
21. A method of treating pulmonary arterial hypertension in a human, comprising administering to the human with pulmonary arterial hypertension ralinepag in combination with riociguat, wherein: ralinepag is administered to the human once or twice daily;
and riociguat is administered to the human once, twice or three times daily.
22. The method of claim 21, wherein the daily amount of ralinepag that is administered to the human is about 0.05 mg to about 0.8 mg.
23. The method of claim 21, wherein the amount of ralinepag that is administered to the human is about 0.05 mg to about 0.6 mg once daily.
24. The method of claim 21, wherein the amount of riociguat that is administered to the human is 0.25 mg, 0.5 mg, 0.75 mg, 1 mg, 1.25 mg, 1.5 mg, 1.75 mg, 2 mg, 2.25 mg, or 2.5 mg twice daily.
25. The method of claim 21, wherein the amount of riociguat that is administered to the human is 0.5 mg, 1 mg, 1.5 mg, 2 mg, or 2.5 mg three times daily.
26. A method of treating pulmonary arterial hypertension in a human, comprising administering to the human with pulmonary arterial hypertension ralinepag in combination with a soluble guanylate cyclase (sGC) stimulator.
27. A method of treating a pulmonary disease in a human in need of treatment with a selective prostacyclin (IP) receptor agonist, comprising administering to the human in need thereof ralinepag in combination with a soluble guanylate cyclase (sGC) stimulator.

28. A method of delaying disease progression in a human and/or reducing a risk of hospitalization for a disease or condition in a human, comprising administering to the human in need thereof ralinepag in combination with a soluble guanylate cyclase (sGC) stimulator, wherein the disease or condition is a pulmonary disease.

29. The method of claim 28, wherein the pulmonary disease is associated with abnormal cell proliferation.

30. A method of improving the treatment of pulmonary arterial hypertension in a human comprising administering ralinepag to the human with pulmonary arterial hypertension in combination with a soluble guanylate cyclase (sGC) stimulator, wherein improving the treatment of pulmonary arterial hypertension in the human comprises a numerical improvement in the six-minute walk test.

31. A method of treating pulmonary arterial hypertension in a human comprising administering ralinepag to the human with pulmonary arterial hypertension in combination with a soluble guanylate cyclase (sGC) stimulator, wherein the co-administration of the soluble guanylate cyclase (sGC) stimulator with ralinepag comprises a reduction in the optimized monotherapy dose of ralinepag in the human.

32. The method of claim 30, wherein the numerical improvement in the six-minute walk test is an increase of at least 40 meters measured by the six-minute walk test.

* * * * *